(12) United States Patent
Tang et al.

(10) Patent No.: US 9,938,538 B2
(45) Date of Patent: Apr. 10, 2018

(54) FERTILITY GENE AND USE THEREOF

(71) Applicants: SHENZHEN INSTITUTE OF MOLECULAR CROP DESIGN, Guangdong (CN); HUNAN WANGHUA AGRICULTURAL BIOTECHNOLOGY CO., LTD., Hunan (CN); SHENZHEN XINGWANG BIOSEED CO., LTD., Guangdong (CN); XINGWANG INVESTMENT CO., LTD., Beijing (CN)

(72) Inventors: Xiaoyan Tang, Guangdong (CN); Zhufeng Chen, Guangdong (CN); Gang Xie, Guangdong (CN); Na Wang, Guangdong (CN); Jiawei Lu, Guangdong (CN); Zaoxia Li, Guangdong (CN)

(73) Assignees: SHENZHEN INSTITUTE OF MOLECULAR CROP DESIGN, Shenzhen, Guangdong (CN); HUNAN WANGHUA AGRICULTURAL BIOTECHNOLOGY CO.,LTD., Hunan (CN); SHENZHEN XINGWANG BIOSEED CO., LTD., Guangdong (CN); XINGWANG INVESTMENT CO., LTD., Beijing (CN)

( * ) Notice: Subject to any disclaimer, the term of this patent is extended or adjusted under 35 U.S.C. 154(b) by 176 days.

(21) Appl. No.: 14/439,565

(22) PCT Filed: Nov. 7, 2013

(86) PCT No.: PCT/CN2013/086657
§ 371 (c)(1),
(2) Date: Apr. 29, 2015

(87) PCT Pub. No.: WO2014/071849
PCT Pub. Date: May 15, 2014

(65) Prior Publication Data
US 2015/0353958 A1    Dec. 10, 2015

(30) Foreign Application Priority Data
Nov. 9, 2012  (CN) .......................... 2012 1 0445558

(51) Int. Cl.
| | | |
|---|---|---|
| A01H 1/00 | (2006.01) |
| A01H 1/06 | (2006.01) |
| C12N 15/82 | (2006.01) |
| C12N 15/113 | (2010.01) |
| A01H 5/00 | (2006.01) |
| C12N 15/00 | (2006.01) |

(52) U.S. Cl.
CPC ........ C12N 15/8289 (2013.01); C12N 15/113 (2013.01); C12N 15/8218 (2013.01); C12N 15/8231 (2013.01); C12N 2310/11 (2013.01)

(58) Field of Classification Search
None
See application file for complete search history.

(56) References Cited

U.S. PATENT DOCUMENTS

2006/0123505 A1* 6/2006 Kikuchi ............... C07K 14/415
                                                           800/278

FOREIGN PATENT DOCUMENTS

CN           102726285         10/2012

OTHER PUBLICATIONS

Yu, J., GenBank (EAY79265.1)—Hypothetical Protein Os1_34381 [Oryza sativa Indica Group]. Feb. 2, 2011.
Tanaka, T., GenBank—NM_001071642.1 [Oryza sativa japonica Group Os10g0524500 (Os10g0524500) mRNA, complete cds. Aug. 6, 2010.
Tanaka, T., GenBank—NP_001065107.1 [Oryza sativa japonica Group 0s10g0524500 (0s10g0524500) mRNA, complete cds. Aug. 6, 2010.
Kato et al., "Isolation of Anther-Specific Gene Promoters Suitable for Transgene Expression in Rice,." Jun. 1, 2010, Plant Molecular Biology Reporter, ISSN:1572-9818.
International Search Report and Written Opinion issued in International Patent Application No. PCT/CN2013/086657, dated Feb. 20, 2014.

* cited by examiner

*Primary Examiner* — Phoenix Bui
(74) *Attorney, Agent, or Firm* — Andrews Kurth Kenyon LLP; Michael Ye

(57) ABSTRACT

The present disclosure relates to a fertility gene and the use thereof, and relates to the biotechnology field, particularly to a method of plant hybrid breeding including creation of a sterile line and preparation of hybrid seeds, more particularly to a fertility gene FL2, a mutant thereof and use thereof in hybrid breeding.

4 Claims, 12 Drawing Sheets

Mutant　　　　　　　Wild-type

Double exposed stigmas　Single exposed stigma

|         |   | *          20          *          40          *          60           |     |
|---------|---|------------------------------------------------------------------------|-----|
| HHZ     | : | ATGGCAGCACTTGGCCGCGCGAGCTCGTCGGCGCCGGTGCTTGCCGCCGCCGCCG                 | 60  |
| Mutant  | : | ATGGCAGCACTTGGCCGCGCGAGCTCGTCGGCGCCGGTGCTTGCCGCCGCCGCCG                 | 60  |
| Nip     | : | ATGGCAGCACTTGGCCGCGCGAGCTCGTCGGCGCCGGTGCTTGCCGCCGCCGCCG-----            | 55  |
|         |   | ATGGCAGCACTTGGCCGCGCGAGCTCGTCGGCGCCGGTGCTTGCCGCCGCCGCCGccgcc            |     |

|         |   | *          80          *          100         *          120          |     |
|---------|---|------------------------------------------------------------------------|-----|
| HHZ     | : | CCGTGCTCGTCTCGCTCTGCCTCGCCGCGCTCTCGGAAGAGCAAGAGCAACTGGAGAAC             | 120 |
| Mutant  | : | CCGTGCTCCTCTCGCTCTGCCTCGCCGCGCTCTCGGAAGAGCAAGAGCAACTGGAGAAC             | 120 |
| Nip     | : | -CCGTGCTCCTCTCGCTCTGCCTCGCCGCGCTCTCGGAAGAGCAAGAGCAACTGGAGAAC            | 114 |
|         |   | gCCGTGCTCCTCTCGCTCTGCCTCGCCGCGCTCTCGGAAGAGCAAGAGCAACTGGAGAAC            |     |

|         |   | *          140         *          160         *          180          |     |
|---------|---|------------------------------------------------------------------------|-----|
| HHZ     | : | CTGCGGTTCGTGCGGCACGCGCAGGACGCGCCGCTGGTGTCGAGCTACAACTACATCGTC           | 180 |
| Mutant  | : | CTGCGGTTCGTGCGGCACGCGCAGGACGCGCCGCTGGTGTCGAGCTACAACTACATCGTC           | 180 |
| Nip     | : | CTGCGGTTCGTGCGGCACGCGCAGGACGCGCCGCTGGTGTCGAGCTACAACTACATCGTC           | 174 |
|         |   | CTGCGGTTCGTGCGGCACGCGCAGGACGCGCCGCTGGTGTCGAGCTACAACTACATCGTC           |     |

|         |   | *          200         *          220         *          240          |     |
|---------|---|------------------------------------------------------------------------|-----|
| HHZ     | : | ATCGGCGGCGGCACGGCGGGGTGCCCGCTGGCGGCGACGCTGTCGGAGCACTCGCGCGTG           | 240 |
| Mutant  | : | ATCGGCGGCGGCACGGCGGGGTGCCCGCTGGCGGCGACGCTGTCGGAGCACTCGCGCGTG           | 240 |
| Nip     | : | ATCGGCGGCGGCACGGCGGGGTGCCCGCTGGCGGCGACGCTGTCGGAGCACTCGCGCGTG           | 234 |
|         |   | ATCGGCGGCGGCACGGCGGGGTGCCCGCTGGCGGCGACGCTGTCGGAGCACTCGCGCGTG           |     |

|         |   | *          260         *          280         *          300          |     |
|---------|---|------------------------------------------------------------------------|-----|
| HHZ     | : | CTGCTGCTGGAGCGCGGCGGCCTGCCGTACGCCAACATGTCGAGCGAGCAGCACTTCACG           | 300 |
| Mutant  | : | CTGCTGCTGGAGCGCGGCGGCCTGCCGTACGCCAACATGTCGAGCGAGCAGCACTTCACG           | 300 |
| Nip     | : | CTGCTGCTGGAGCGCGGCGGCCTGCCGTACGCCAACATGTCGAGCGAGCAGCACTTCACG           | 294 |
|         |   | CTGCTGCTGGAGCGCGGCGGCCTGCCGTACGCCAACATGTCGAGCGAGCAGCACTTCACG           |     |

|         |   | *          320         *          340         *          360          |     |
|---------|---|------------------------------------------------------------------------|-----|
| HHZ     | : | GACGCGCTGGCCGACACGTCGCCGGCGTCGCCGGCGCAGCGGTTCATCTCGGAGGACGGC           | 360 |
| Mutant  | : | GACGCGCTGGCCGACACGTCGCCGGCGTCGCCGGCGCAGCGGTTCATCTCGGAGGACGGC           | 360 |
| Nip     | : | GACGCGCTGGCCGACACGTCGCCGGCGTCGCCGGCGCAGCGGTTCATCTCGGAGGACGGC           | 354 |
|         |   | GACGCGCTGGCCGACACGTCGCCGGCGTCGCCGGCGCAGCGGTTCATCTCGGAGGACGGC           |     |

|         |   | *          380         *          400         *          420          |     |
|---------|---|------------------------------------------------------------------------|-----|
| HHZ     | : | GTGGTGAACGCCCGGGCGCGGGTGCTCGGCGGCGGGAGCTGCCTCAACGCCGGGTTCTAC           | 420 |
| Mutant  | : | GTGGTGAACGCCCGGGCGCGGGTGCTCGGCGGCGGGAGCTGCCTCAACGCCGGGTTCTAC           | 420 |
| Nip     | : | GTGGTGAACGCCCGGGCGCGGGTGCTCGGCGGCGGGAGCTGCCTCAACGCCGGGTTCTAC           | 414 |
|         |   | GTGGTGAACGCCCGGGCGCGGGTGCTCGGCGGCGGGAGCTGCCTCAACGCCGGGTTCTAC           |     |

|         |   | *          440         *          460         *          480          |     |
|---------|---|------------------------------------------------------------------------|-----|
| HHZ     | : | ACGCGGGCGAGCAACGAGTACGTGCGCGCCCCCGGGTGGGACGCGCGGCTGGTGAACTCG           | 480 |
| Mutant  | : | ACGCGGGCGAGCAACGAGTACGTGCGCGCCCCCGGGTGGGACGCGCGGCTGGTGAACTCG           | 480 |
| Nip     | : | ACGCGGGCGAGCAACGAGTACGTGCGCGCCTCCGGGTGGGACGCGCGGCTGGTGAACTCG           | 474 |
|         |   | ACGCGGGCGAGCAACGAGTACGTGCGCGCCgCCGGGTGGGACGCGCGGCTGGTGAACTCG           |     |

|         |   | *          500         *          520         *          540          |     |
|---------|---|------------------------------------------------------------------------|-----|
| HHZ     | : | TCGTACCGGTGGGTGGAGCGCTCGCTGGTGTTCCGCCCCGACGTGCCGCCGTGGCAGGCG           | 540 |
| Mutant  | : | TCGTACCGGTGGGTGGAGCGCTCGCTGGTGTTCCGCCCCGACGTGCCGCCGTGGCAGGCG           | 540 |
| Nip     | : | TCGTACCGGTGGGTGGAGCGCTCGCTGGTGTTCCGCCCCGACGTGCCGCCGTGGCAGGCG           | 534 |
|         |   | TCGTACCGGTGGGTGGAGCGCTCGCTGGTGTTCCGCCCCGACGTGCCGCCGTGGCAGGCG           |     |

|         |   | *          560         *          580         *          600          |     |
|---------|---|------------------------------------------------------------------------|-----|
| HHZ     | : | GCGCTCCGCGACGCGCTGCTCGAGGTCGGCGTCACGCCCGACAACGGCTTCACCTTCGAC           | 600 |
| Mutant  | : | GCGCTCCGCGACGCGCTGCTCGAGGTCGGCGTCACGCCCGACAACGGCTTCACCTTCGAC           | 600 |
| Nip     | : | GCGCTCCGCGACGCGCTGCTCGAGGTCGGCGTCACGCCCGACAACGGCTTCACCTTCGAC           | 594 |
|         |   | GCGCTCCGCGACGCGCTGCTCGAGGTCGGCGTCACGCCCGACAACGGCTTCACCTTCGAC           |     |

|         |   | *          620         *          640         *          660          |     |
|---------|---|------------------------------------------------------------------------|-----|
| HHZ     | : | CACGTCACCGGCACCAAGATCGGCGGCACCATCTTCGACAACTCCGGCCAGCGCCACACC           | 660 |
| Mutant  | : | CACGTCACCGGCACCAAGATCGGCGGCACCATCTTCGACAACTCCGGCCAGCGCCACACC           | 660 |
| Nip     | : | CACGTCACCGGCACCAAGATCGGCGGCACCATCTTCGACAACTCCGGCCAGCGCCACACC           | 654 |
|         |   | CACGTCACCGGCACCAAGATCGGCGGCACCATCTTCGACAACTCCGGCCAGCGCCACACC           |     |

Fig. 6A

```
             *         680         *         700         *         720
HHZ     : GCCGCCGACTTCCTCCGCCACGCCCGCCCCCGCGGCCCTCACCGTCCTCCTCTACGCCACC : 720
Mutant  : GCCGCCGACTTCCTCCGCCACGCCCGCCCCCGCGGCCCTCACCGTCCTCCTCTACGCCACC : 720
Nip     : GCCGCCGACTTCCTCCGCCACGCCCGCCCCCGCGGCCTCACCGTCCTCCTCTACGCCACC  : 714
          GCCGCCGACTTCCTCCGCCACGCCCGCCCCCGCGGCCTCACCGTCCTCCTCTACGCCACC

*         740         *         760         *         780
HHZ     : GTCTCCCGTATCCTCTTCAAAAGCCAAGACGGGGTGCCGTACCCGGTGGCGTACGGGGTG : 780
Mutant  : GTCTCCCGTATCCTCTTCAAAAGCCAAGACGGGGTGCCGTACCCGGTGGCGTACGGGGTG : 780
Nip     : GTCTCCCGTATCCTCTTCAAAAGCCAAGACGGGGTGCCGTACCCGGTGGCGTACGGGGTG : 774
          GTCTCCCGTATCCTCTTCAAAAGCCAAGACGGGGTGCCGTACCCGGTGGCGTACGGGGTG

*         800         *         820         *         840
HHZ     : GTGTTCTCGGACCCGCTGGGGGTGCAGCACCGGGTGTACCTCCGCGACGGCGACAAGAAC : 840
Mutant  : GTGTTCTCGGACCCGCTGGGGGTGCAGCACCGGGTGTACCTCCGCGACGGCGACAAGAAC : 840
Nip     : GTGTTCTCGGACCCGCTGGGGGTGCAGCACCGGGTGTACCTCCGCGACGGCGACAAGAAC : 834
          GTGTTCTCGGACCCGCTGGGGGTGCAGCACCGGGTGTACCTCCGCGACGGCGACAAGAAC

*         860         *         880         *         900
HHZ     : GAGGTGATCGTGTCGGCGGGGACGCTGGGGAGCCCCGAGCTGCTGATCCTGAGCGGCGTC : 900
Mutant  : GAGGTGATCGTGTCGGCGGGGACGCTGGGGAGCCCCGAGCTGCTGATGCTGAGCGGCGTC : 900
Nip     : GAGGTGATCGTGTCGGCGGGGACGCTGGGGAGCCCGCAGCTGCTGATGCTGAGCGGCGTC : 894
          GAGGTGATCGTGTCGGCGGGGACGCTGGGGAGCCCGCAGCTGCTGATGCTGAGCGGCGTC

*         920         *         940         *         960
HHZ     : GGGCCGCAGGCGCACCTGGAGGCGCACGGCATCGAGGTGATCGTGGACCAACCCATGGTC : 960
Mutant  : GGGCCGCAGGCGCACCTGGAGGCGCACGGCATCGAGGTGATCGTGGACCAACCCATGGTC : 960
Nip     : GGGCCGCAGGCGCACCTGGAGGCGCACGGCATCGAGGTGATCGTGGACCAACCCATGGTC : 954
          GGGCCGCAGGCGCACCTGGAGGCGCACGGCATCGAGGTGATCGTGGACCAACCCATGGTC

*         980         *        1000         *        1020
HHZ     : GGGCAGGGCGTCGCCGACAACCCGATGAACTCGGTGTTCATCCCGTCGCCGGTGCCGGTG : 1020
Mutant  : GGGCAGGGCGTCGCCGACAACCCGATGAACTCGGTGTTCATCCCGTCGCCGGTGCCGGTG : 1020
Nip     : GGGCAGGGCGTCGCCGACAACCCGATGAACTCGGTGTTCATCCCGTCGCCGGTGCCGGTG : 1014
          GGGCAGGGCGTCGCCGACAACCCGATGAACTCGGTGTTCATCCCGTCGCCGGTGCCGGTG

*        1040         *        1060         *        1080
HHZ     : GAGCTCTCCCTGGTGCAGGTCGTCGGCATCACCCGCTCCGGCAGCTTCATCGAGGGGGTG : 1080
Mutant  : GAGCTCTCCCTGGTGCAGGTCGTCGGCATCACCCGCTCCGGCAGCTTCATCGAGGGGGTG : 1080
Nip     : GAGCTCTCCCTGGTGCAGGTCGTCGGCATCACCCGCTCCGGCAGCTTCATCGAGGGGGTG : 1074
          GAGCTCTCCCTGGTGCAGGTCGTCGGCATCACCCGCTCCGGCAGCTTCATCGAGGGGGTG

*        1100         *        1120         *        1140
HHZ     : AGCGGGTCGGAGTTCGGCATGCCGGTGTCGGACGGCGCGCTCCGGTGGGCGCGCAGCTTC : 1140
Mutant  : AGCGGGTCGGAGTTCGGCATGCCGGTGTCGGACGGCGCGCTCCGGTGGGCGCGCAGCTTC : 1140
Nip     : AGCGGGTCGGAGTTCGGCATGCCGGTGTCGGACGGCGCGCTCCGGTGGGCGCGCAGCTTC : 1134
          AGCGGGTCGGAGTTCGGCATGCCGGTGTCGGACGGCGCGCTCCGGTGGGCGCGCAGCTTC

*        1160         *        1180         *        1200
HHZ     : GGGATGCTGTCGCCGCAGACGGGGCAGCTCGGCACGCTGCCGCCGAAGCAGAGGACGCCG : 1200
Mutant  : GGGATGCTGTCGCCGCAGACGGGGCAGCTCGGCACGCTGCCGCCGAAGCAGAGGACGCCG : 1200
Nip     : GGGATGCTGTCGCCGCAGACGGGGCAGCTCGGCACGCTGCCGCCGAAGCAGAGGACGCCG : 1194
          GGGATGCTGTCGCCGCAGACGGGGCAGCTCGGCACGCTGCCGCCGAAGCAGAGGACGCCG

*        1220         *        1240         *        1260
HHZ     : GAGGCGCTGCAGCGGGCGGCGGAGGCGATGATGCGGCTGGACAGGAGGGCGTTCCGGGGA : 1260
Mutant  : GAGGCGCTGCAGCGGGCGGCGGAGGCGATGATGCGGCTGGACAGGAGGGCGTTCCGGGGA : 1260
Nip     : GAGGCGCTGCAGCGGGCGGCGGAGGCGATGATGCGGCTGGACAGGAGGGCGTTCCGGGGA : 1254
          GAGGCGCTGCAGCGGGCGGCGGAGGCGATGATGCGGCTGGACAGGAGGGCGTTCCGGGGA

*        1280         *        1300         *        1320
HHZ     : GGCTTCATCCTGGAGAAGATCCTCGGGCCGGTGTCCTCCGGCCACGTCGAGCTGCGAACC : 1320
Mutant  : GGCTTCATCCTGGAGAAGATCCTCGGGCCGGTGTCCTCCGGCCACGTCGAGCTGCGAACC : 1320
Nip     : GGCTTCATCCTGGAGAAGATCCTCGGGCCGGTGTCCTCCGGCCACGTCGAGCTGCGAACC : 1314
          GGCTTCATCCTGGAGAAGATCCTCGGGCCGGTGTCCTCCGGCCACGTCGAGCTGCGAACC
```

Fig. 6B

```
              *         1340         *         1360         *         1380
HHZ     : ACCGACCCGAGGGCGAACCCGTCGGTGACGTTCAACTACTTCCGCGAGGCGGAGGATCTG : 1380
Mutant  : ACCGACCCGAGGGCGAACCCGTCGGTGACGTTCAACTACTTCCGCGAGGCGGAGGATCTG : 1380
Nip     : ACCGACCCGAGGGCGAACCCGTCGGTGACGTTCAACTACTTCCGCGAGGCAGAGGATCTG : 1374
          ACCGACCCGAGGGCGAACCCGTCGGTGACGTTCAACTACTTCCGCGAGGCgGAGGATCTG

*         1400         *         1420         *         1440
HHZ     : GAGCGGTGCGTCCATGGCATCGAGACGATCGAGCGGGTGATCCAGTCGCGGGCCTTCTCC : 1440
Mutant  : GAGCGGTGCGTCCATGGCATCGAGACGATCGAGCGGGTGATCCAGTCGCGGGCCTTCTCC : 1440
Nip     : GAGCGGTGCGTCCATGGCATCGAGACGATCGAGCGGGTGATCCAGTCGCGGGCCTTCTCC : 1434
          GAGCGGTGCGTCCATGGCATCGAGACGATCGAGCGGGTGATCCAGTCGCGGGCCTTCTCC

*         1460         *         1480         *         1500
HHZ     : AACTTCACCTACGCCAACGCCTCCGTCGAGTCCATCTTCACCGATTCCGCCAACTTCCCC : 1500
Mutant  : AACTTCACCTACGCCAACGCCTCCGTCGAGTCCATCTTCACCGATTCCGCCAACTTCCCC : 1500
Nip     : AACTTCACCTACGCCAACGCCTCCGTCGAGTCCATCTTCACCGATTCCGCCAACTTCCCC : 1494
          AACTTCACCTACGCCAACGCCTCCGTCGAGTCCATCTTCACCGATTCCGCCAACTTCCCC

*         1520         *         1540         *         1560
HHZ     : GTCAACCTGCTGCCGCGCCATGTCAACGACTCGCGCTCGCCGGAGCAGTACTGCATGGAC : 1560
Mutant  : GTCAACCTGCTGCCGCGCCATGTCAACGACTCGCGCTCGCCGGAGCAGTACTGCATGGAC : 1560
Nip     : GTCAACCTGCTGCCGCGCCATGTCAACGACTCGCGCTCGCCGGAGCAGTACTGCATGGAC : 1554
          GTCAACCTGCTGCCGCGCCATGTCAACGACTCGCGCTCGCCGGAGCAGTACTGCATGGAC

*         1580         *         1600         *         1620
HHZ     : ACCGTCATGACCATCTGGCACTACCACGGCGGCTGCCATGTCGGCGCCGTCGTCGACGAC : 1620
Mutant  : ACCGTCATGACCATCTGGCACTACCACGGCGGCTGCCATGTCGGCGCCGTCGTCGACGAC : 1620
Nip     : ACCGTCATGACCATCTGGCACTACCACGGCGGCTGCCATGTCGGCGCCGTCGTCGACGAC : 1614
          ACCGTCATGACCATCTGGCACTACCACGGCGGCTGCCATGTCGGCGCCGTCGTCGACGAC

*         1640         *         1660         *         1680
HHZ     : GATTACCGGGTGTTCGGGGTGCAGGGGCTCAGGGTGATCGACAGCTCCACCTTCAAGTAC : 1680
Mutant  : GATTACCGGGTGTTCGGGGTGCAGGGGCTCAGGGTGATCGACAGCTCCACCTTCAAGTAC : 1680
Nip     : GATTACCGGGTGTTCGGGGTGCAGGGGCTCAGGGTGATCGACAGCTCCACCTTCAAGTAC : 1674
          GATTACCGGGTGTTCGGGGTGCAGGGGCTCAGGGTGATCGACAGCTCCACCTTCAAGTAC

*         1700         *         1720         *         1740
HHZ     : TCCCCCGCCACCAACCCTCAGGCCACCGTCATGATGCTCGGCAGGTATATGGGTGTGAAG : 1740
Mutant  : TCCCCCGACACCAACCCTCAGGCCACCGTCATGATGCTCGGCAGGTATATGGGTGTGAAG : 1740
Nip     : TCCCCCGGCACCAACCCTCAGGCCACCGTCATGATGCTCGGCAGGTATATGGGTGTGAAG : 1734
          TCCCCCGgCACCAACCCTCAGGCCACCGTCATGATGCTCGGCAGGTATATGGGTGTGAAG

*         1760
HHZ     : ATTCAGTCCGAGAGATGGAAGAAATGA : 1767
Mutant  : ATTCAGTCCGAGAGATGGAAGAAATGA : 1767
Nip     : ATTCAGTCCGAGAGATGGAAGAAATGA : 1761
          ATTCAGTCCGAGAGATGGAAGAAATGA
```

Fig. 6C

Fig. 7 root steam leaf flower

Fig. 14

SEQUENCE LISTING

<160> NUMBER OF SEQ ID NOS: 43

<210> SEQ ID NO 1
<211> LENGTH: 1767
<212> TYPE: DNA
<213> ORGANISM: Oryza sativa

<400> SEQUENCE: 1
atggcagcac ttggccgcgc gagctcgtcg gcgccggtgc ttgccgccgc cgccgccgcc    60

```
gccgtgctcc tctcgctctg cctcgccgcg ctctcggaag agcaagagca actggagaac    120
ctgcggttcg tgcggcacgc gcaggacgcg ccgctggtgt cgagctacaa ctacatcgtc    180
atcggcggcg gcacggcggg gtgcccgctg gcggcgacgc tgtcggagca ctcgcgcgtg    240
ctgctgctag agcgcggcgg cctgccgtac gccaacatgt cgagcgagca gcacttcacg    300
gacgcgctgg ccgacacgtc gccggcgtcg ccggcgcagc ggttcatctc ggaggacggc    360
gtggtgaacg cccgggcgcg ggtgctcggc ggcgggagct gcctcaacgc cgggttctac    420
acgcgggcga gcaacgagta cgtgcgcgcc gccgggtggg acgcgcggct ggtgaactcg    480
tcgtaccggt gggtggagcg ctcgctggtg ttccgcccg acgtgccgcc gtggcaggcg    540
gcgctccgcg acgcgctgct cgaggtcggc gtcacgcccg acaacggctt caccttcgac    600
cacgtcaccg gcaccaagat cggcggcacc atcttcgaca actccggcca cgccacacc     660
gccgccgact tcctccgcca cgcccgcccc cgcggcctca ccgtcctcct ctacgccacc    720
gtctcccgta tcctcttcaa aagccaagac ggggtgccgt accggtggc gtacggggtg    780
gtgttctcgg acccgctggg ggtgcagcac cgggtgtacc tccgcgacgg cgacaagaac    840
gaggtgatcg tgtcggcggg gacgctgggg agcccgcagc tgctgatgct gagcggcgtc    900
gggccgcagg cgcacctgga ggcgcacggc atcgaggtga tcgtggacca acccatggtc    960
gggcagggcg tcgccgacaa cccgatgaac tcggtgttca tcccgtcgcc ggtgccggtg   1020
gagctctccc tggtgcaggt cgtcggcatc accccgctccg gcagcttcat cgaggggctg   1080
agcgggtcgg agttcggcat gccggtgtcg gacggcgcgc tccggtgggc gcgcagcttc   1140
gggatgctgt cgccgcagac ggggcagctc ggcacgctgc cgccgaagca gaggacgccg   1200
gaggcgctgc agcgggcggc ggaggcgatg atgcggctgg acaggagggc gttccgggga   1260
ggcttcatcc tggagaagat cctcgggccg gtgtcctccg ccacgtcga gctgcgaacc   1320
accgacccga gggcgaaccc gtcggtgacg ttcaactact ccgcgaggc ggaggatctg   1380
gagcggtgcg tccatggcat cgagacgatc gagcgggtga tccagtcgcg ggccttctcc   1440
aacttcacct acgccaacgc ctccgtcgag tccatcttca ccgattccgc caacttcccc   1500
gtcaacctgc tgccgcgcca tgtcaacgac tcgcgctcgc cggagcagta ctgcatggac   1560
accgtcatga ccatctggca ctaccacgg ggctgccatg tcggcgccgt cgtcgacgac   1620
gattaccggg tgttcggggt gcaggggctc agggtgatcg acagctccac cttcaagtac   1680
tcccccggca ccaaccctca ggccaccgtc atgatgctcg caggtatat gggtgtgaag   1740
attcagtccg agagatggaa gaaatga                                       1767
```

<210> SEQ ID NO 2
<211> LENGTH: 588
<212> TYPE: PRT
<213> ORGANISM: Oryza sativa

<400> SEQUENCE: 2

Met Ala Ala Leu Gly Arg Ala Ser Ser Ser Ala Pro Val Leu Ala Ala
1               5                   10                  15

Ala Ala Ala Ala Ala Val Leu Leu Ser Leu Cys Leu Ala Ala Leu Ser
            20                  25                  30

Glu Glu Gln Glu Gln Leu Glu Asn Leu Arg Phe Val Arg His Ala Gln
        35                  40                  45

Asp Ala Pro Leu Val Ser Ser Tyr Asn Tyr Ile Val Ile Gly Gly Gly
    50                  55                  60

-continued

Thr Ala Gly Cys Pro Leu Ala Thr Leu Ser Glu His Ser Arg Val
 65                  70                  75                  80

Leu Leu Leu Glu Arg Gly Gly Leu Pro Tyr Ala Asn Met Ser Ser Glu
                 85                  90                  95

Gln His Phe Thr Asp Ala Leu Ala Asp Thr Ser Pro Ala Ser Pro Ala
                100                 105                 110

Gln Arg Phe Ile Ser Glu Asp Gly Val Val Asn Ala Arg Ala Arg Val
                115                 120                 125

Leu Gly Gly Gly Ser Cys Leu Asn Ala Gly Phe Tyr Thr Arg Ala Ser
    130                 135                 140

Asn Glu Tyr Val Arg Ala Ala Gly Trp Asp Ala Arg Leu Val Asn Ser
145                 150                 155                 160

Ser Tyr Arg Trp Val Glu Arg Ser Leu Val Phe Arg Pro Asp Val Pro
                165                 170                 175

Pro Trp Gln Ala Ala Leu Arg Asp Ala Leu Leu Glu Val Gly Val Thr
                180                 185                 190

Pro Asp Asn Gly Phe Thr Phe Asp His Val Thr Gly Thr Lys Ile Gly
                195                 200                 205

Gly Thr Ile Phe Asp Asn Ser Gly Gln Arg His Thr Ala Ala Asp Phe
    210                 215                 220

Leu Arg His Ala Arg Pro Arg Gly Leu Thr Val Leu Leu Tyr Ala Thr
225                 230                 235                 240

Val Ser Arg Ile Leu Phe Lys Ser Gln Asp Gly Val Pro Tyr Pro Val
                245                 250                 255

Ala Tyr Gly Val Val Phe Ser Asp Pro Leu Gly Val Gln His Arg Val
                260                 265                 270

Tyr Leu Arg Asp Gly Asp Lys Asn Glu Val Ile Val Ser Ala Gly Thr
                275                 280                 285

Leu Gly Ser Pro Gln Leu Leu Met Leu Ser Gly Val Gly Pro Gln Ala
    290                 295                 300

His Leu Glu Ala His Gly Ile Glu Val Ile Val Asp Gln Pro Met Val
305                 310                 315                 320

Gly Gln Gly Val Ala Asp Asn Pro Met Asn Ser Val Phe Ile Pro Ser
                325                 330                 335

Pro Val Pro Val Glu Leu Ser Leu Val Gln Val Val Gly Ile Thr Arg
                340                 345                 350

Ser Gly Ser Phe Ile Glu Gly Val Ser Gly Ser Glu Phe Gly Met Pro
    355                 360                 365

Val Ser Asp Gly Ala Leu Arg Trp Ala Arg Ser Phe Gly Met Leu Ser
    370                 375                 380

Pro Gln Thr Gly Gln Leu Gly Thr Leu Pro Pro Lys Gln Arg Thr Pro
385                 390                 395                 400

Glu Ala Leu Gln Arg Ala Ala Glu Ala Met Met Arg Leu Asp Arg Arg
                405                 410                 415

Ala Phe Arg Gly Gly Phe Ile Leu Glu Lys Ile Leu Gly Pro Val Ser
                420                 425                 430

Ser Gly His Val Glu Leu Arg Thr Thr Asp Pro Arg Ala Asn Pro Ser
    435                 440                 445

Val Thr Phe Asn Tyr Phe Arg Glu Ala Glu Asp Leu Glu Arg Cys Val
    450                 455                 460

His Gly Ile Glu Thr Ile Glu Arg Val Ile Gln Ser Arg Ala Phe Ser
465                 470                 475                 480

Asn Phe Thr Tyr Ala Asn Ala Ser Val Glu Ser Ile Phe Thr Asp Ser

```
                    485                 490                 495
Ala Asn Phe Pro Val Asn Leu Leu Pro Arg His Val Asn Asp Ser Arg
                500                 505                 510

Ser Pro Glu Gln Tyr Cys Met Asp Thr Val Met Thr Ile Trp His Tyr
            515                 520                 525

His Gly Gly Cys His Val Gly Ala Val Val Asp Asp Asp Tyr Arg Val
        530                 535                 540

Phe Gly Val Gln Gly Leu Arg Val Ile Asp Ser Ser Thr Phe Lys Tyr
545                 550                 555                 560

Ser Pro Gly Thr Asn Pro Gln Ala Thr Val Met Met Leu Gly Arg Tyr
                565                 570                 575

Met Gly Val Lys Ile Gln Ser Glu Arg Trp Lys Lys
            580                 585

<210> SEQ ID NO 3
<211> LENGTH: 2520
<212> TYPE: DNA
<213> ORGANISM: Oryza sativa

<400> SEQUENCE: 3
```

| | | | | | |
|---|---|---|---|---|---|
| ggatttcgag | gatcaagctc | cagatctcga | gcaaggcaag | ccacctttga | acatcttgag | 60 |
| cctatatttg | aaatttaatt | atgttgcttg | aaaaatatta | tgcattgata | ggaccgcact | 120 |
| taatctgttg | acccgtctgc | aaggcagatt | ggcggaccta | cctaatttgt | tgcatttgat | 180 |
| ccttcctttg | ttaattgtta | tatcatgtcc | ccttgtaacc | atctagttgc | gtctcgatat | 240 |
| tcgtgcaccc | tgtgcgagta | tcgacggacg | ccttcaaact | taaaatctga | ataacaactt | 300 |
| gggtaaaact | tgggttttac | aaaagacttg | gaaaacccga | cacctgggtc | ggtgcttgcg | 360 |
| aactaaatga | atttccaaaa | ccgcggaccg | gggaacgtac | cgggtgtacg | gtttcccgct | 420 |
| cttgcactta | aggaccgttt | ccttggaatt | tcatctaaac | ataagacaag | tacgaccaca | 480 |
| tgggtggaat | gggacacccc | tggctgagta | actagcttat | caggggagcc | ttgatgccga | 540 |
| gagacatgtg | gattcgccgg | ggtggtgtcg | gggaggaccc | ctgggcttcc | tggcacagca | 600 |
| tggtctggga | cctaacctgt | tgttggtctg | gaccccctct | cgtcagcata | tggtaaacct | 660 |
| gtgtcggctt | tcgaaatgcc | ttgtcatgaa | agcttggagg | tctcccgacg | tggctgatcc | 720 |
| ccacgggctg | ggtgatccgg | gttagtaatg | tcgtgtgggt | aaagtgtacc | ccctctgcag | 780 |
| aggttaacaa | actgtttgaa | cagccgtgcc | cacggtcatg | ggcggatgtg | aggtgattcc | 840 |
| tagtgtagtt | ttgtttgact | actgcttgtg | aaattgctgt | tgtggaaagg | ggttcgatgt | 900 |
| ttgaaaaatc | tgcagctgat | aggatcagct | aggcccgggt | ggccgtttga | aagttgttgg | 960 |
| cccgggtggc | cgttgaaaag | ccgttggccg | ggtgccaacc | ttgattcatt | tctaaagact | 1020 |
| gatacattgc | acatactccg | accggacgag | acgcactgtc | tcatccgtgt | cgttgagaag | 1080 |
| cactcactta | gttgttttta | gaaaagagtt | caaataaaat | caattgcaaa | acaacagtc | 1140 |
| ttttcttgaa | gcctgcatta | aacacttatt | tcccatggct | tgctgagtac | tcctgtactc | 1200 |
| acccttgctc | tatataaata | atccccccc | agttgctgaa | gaagatgaag | cggaacctgc | 1260 |
| tgatgaggag | ttcttccagg | agcaagccgg | ctacgatgag | ttttagggtt | tcggcctagt | 1320 |
| tcccaagtca | cgcctgtgtt | gtttggtcca | agtcctggct | tccgtttccc | ttttgtaatg | 1380 |
| cagttgtgag | ctcgggatct | gtccgcagcc | caacataact | gtacctctac | tctataataa | 1440 |
| agagacctct | attgctgtga | tattccgtct | tcctgcgata | ccagcactgt | ttcctgggac | 1500 |
| tggtatcgat | taacaggtta | atttggagcg | tcacgggcta | attccggtcg | gtactagttc | 1560 |

```
ggggcgtgac aaaaacacaa aaaaaagaaa ccaaccgtct aaaaacttac aactttacca    1620
ttcggcaata caactgcaat gggccaagaa gttaatttaa agttaagagc aaattcattt    1680
ggaccacctt tgttacaga tgcttcactt tggaccacat accacccatc tctcttctcg     1740
agcatgaaca atctcgatta cattggctcc tactcatcaa taaactctca catatatatg    1800
taaaaccatt catcggtata tgacaagtta tatatggata aaagagttga ggatgatcca    1860
aaatgtcaca aaggtaagaa taataaccgg tataaagtga aacatcgat aaacatcgct     1920 aataaaagtt cgtctatagt aaaatttact ctaaaattaa atcacctaat attttaatat    1980
ttttttgtac aaatggaccg tttcaatggg gctttatcag atttagttga gatgcataca    2040
tggtaagcac cgtcataatc ttgcccaaga gctgacccaa ctcattaaaa ttacgcttct    2100
tttacgactt aataaatcaa gaagaaacca ttgaaatcca gcctgccccg actgtctcgt    2160
aacagaaaaa taactaagca acgactaaat tatgatttta aaatggcaaa aatatcaaag    2220
cacgttcgaa acaatcgcaa gattggcaag taaaactctcc tgcttgcttg ctcacaacca   2280
catcagatca ttgatcaatg tttcatcagc tcatcacttc tgcatgcatg ttatattctt    2340
ctcagggctc ctccacaatt tacaaagctg ctcgaagatc ttctttgcag tgcaaagcaa    2400
tctgcaagat tattcaagac atctactctt gatctaccat tgagctaact ccggatatat    2460
aaacagaccg aacgtttcgt cccaggggaa tgtgaaagtt agcgaatttg cccggcgaaa    2520

<210> SEQ ID NO 4
<211> LENGTH: 5040
<212> TYPE: DNA
<213> ORGANISM: Oryza sativa

<400> SEQUENCE: 4
ggatttcgag gatcaagctc cagatctcga gcaaggcaag ccacctttga acatcttgag     60
cctatatttg aaatttaatt atgttgcttg aaaaatatta tgcattgata ggaccgcact    120
taatctgttg acccgtctgc aaggcagatt ggcggaccta cctaatttgt tgcatttgat    180
ccttcctttg ttaattgtta tatcatgtcc ccttgtaacc atctagttgc gtctcgatat    240
tcgtgcaccc tgtgcgagta tcgacggacg ccttcaaact taaaatctga ataacaactt    300 gggtaaaaact tgggttttac aaaagacttg gaaaacccga cacctgggtc ggtgcttgcg    360
aactaaatga atttccaaaa ccgcggaccg gggaacgtac cgggtgtacg gtttcccgct    420
cttgcactta aggaccgttt ccttggaatt tcatctaaac ataagacaag tacgaccaca     480
tgggtggaat gggacacccc tggctgagta actagcttat caggggagcc ttgatgccga    540
gagacatgtg gattcgccgg ggtggtgtcg gggaggaccc ctgggcttcc tggcacagca    600
tggtctggga cctaacctgt tgttggtctg gacccctct cgtcagcata tggtaaacct     660
gtgtcggctt tcgaaatgcc ttgtcatgaa agcttggagg tctcccgacg tggctgatcc    720
ccacgggctg ggtgatccgg gttagtaatg tcgtgtgggt aaagtgtacc ccctctgcag    780
aggttaacaa actgtttgaa cagccgtgcc cacggtcatg ggcggatgtg aggtgattcc    840
tagtgtagtt tgtttgact actgcttgtg aaattgctgt tgtggaaagg ggttcgatgt     900
ttgaaaaatc tgcagctgat aggatcagct aggcccgggt ggccgtttga agttgttgg     960 cccgggtggc cgttgaaaag ccgttggccg ggtgccaacc ttgattcatt tctaaagact    1020
gatacattgc acatactccg accggacgag acgcactgtc tcatccgtgt cgttgagaag    1080
cactcactta gttgttttta gaaaagagtt caaataaaat caattgcaaa acaacagtc     1140
```

-continued

```
ttttcttgaa gcctgcatta aacacttatt tcccatggct tgctgagtac tcctgtactc    1200
acccttgctc tatataaata atccccccccc agttgctgaa gaagatgaag cggaacctgc    1260
tgatgaggag ttcttccagg agcaagccgg ctacgatgag ttttagggtt tcggcctagt    1320
tcccaagtca cgcctgtgtt gtttggtcca agtcctggct tccgtttccc ttttgtaatg    1380
cagttgtgag ctcgggatct gtccgcagcc aacataact gtacctctac tctataataa    1440
agagacctct attgctgtga tattccgtct tcctgcgata ccagcactgt ttcctgggac    1500
tggtatcgat taacaggtta atttggagcg tcacgggcta attccggtcg gtactagttc    1560
ggggcgtgac aaaaacacaa aaaaaagaaa ccaaccgtct taaaacttac aactttacca    1620
ttcggcaata caactgcaat gggccaagaa gttaatttaa agttaagagc aaattcattt    1680
ggaccacctt tgttacaga tgcttcactt tggaccacat accacccatc tctcttctcg    1740
agcatgaaca atctcgatta cattggctcc tactcatcaa taaactctca catatatatg    1800
taaaaccatt catcggtata tgacaagtta tatatggata aaagagttga ggatgatcca    1860
aaatgtcaca aaggtaagaa taataaccgg tataaagtga gaacatcgat aaacatcgct    1920
aataaaagtt cgtctatagt aaaatttact ctaaaattaa atcacctaat attttaatat    1980
ttttttgtac aaatggaccg tttcaatggg gctttatcag atttagttga gatgcataca    2040
tggtaagcac cgtcataatc ttgcccaaga gctgacccaa ctcattaaaa ttacgcttct    2100
tttacgactt aataaatcaa gaagaaacca ttgaaatcca gcctgccccg actgtctcgt    2160
aacagaaaaa taactaagca acgactaaat tatgatttta aaatggcaaa aatatcaaag    2220
cacgttcgaa acaatcgcaa gattggcaag taaaactctcc tgcttgcttg ctcacaacca    2280
catcagatca ttgatcaatg tttcatcagc tcatcacttc tgcatgcatg ttatattctt    2340
ctcagggctc ctccacaatt tacaaagctg ctcgaagatc ttctttgcag tgcaaagcaa    2400
tctgcaagat tattcaagac atctactctt gatctaccat tgagctaact ccggatatat    2460
aaacagaccg aacgtttcgt cccaggggaa tgtgaaagtt agcgaatttg cccggcgaaa    2520
atggcagcac ttggccgcgc gagctcgtcg gcgccggtgc ttgccgccgc cgccgccgcc    2580
gccgtgctcc tctcgctctg cctcgccgcg ctctcggaag agcaaggtgc gtaaacgttg    2640
cgttgtatct ttgcgttgat gcgtgttgcg tcgtcgtcgt gttcatggcg tgcgatggcg    2700
ttgtgcagag caactggaga acctgcggtt cgtgcggcac gcgcaggacg cgccgctggt    2760
gtcgagctac aactacatcg tcatcggcgg cggcacggcg gggtgccgc tggcggcgac    2820 gctgtcggag cactcgcgcg tgctgctgct ggagcgcggc ggcctgccgt acgccaacat    2880
gtcgagcgag cagcacttca cggacgcgct ggccgacacg tcgccggcgt cgccggcgca    2940
gcggttcatc tcggaggacg gcgtggtgaa cgcccgggcg cgggtgctcg gcggcgggag    3000
ctgcctcaac gccgggttct acacgcgggc gagcaacgag tacgtgcgcg ccgccgggtg    3060
ggacgcgcgg ctggtgaact cgtcgtaccg gtgggtggag cgctcgctgg tgttccgccc    3120
cgacgtgccg ccgtggcagg cggcgctccg cgacgcgctg ctcgaggtcg gcgtcacgcc    3180
cgacaacggc ttcaccttcg accacgtcac cggcaccaag atcggcggca ccatcttcga    3240
caactccggc cagcgccaca ccgccgccga cttcctccgc cacgcccgcc ccgcggcct    3300 caccgtcctc ctctacgcca ccgtctcccg tatcctcttc aaaagccaag gtacacagct    3360
acgatgaaaa tggaaaatgt gctgtgcgcc gaagaagctt gacctcacga cggcgagctt    3420
ttgccatggc gtgcagacgg ggtgccgtac ccggtggcgt acggggtggt gttctcggac    3480
ccgctggggg tgcagcaccg ggtgtacctc cgcgacggcg acaagaacga ggtgatcgtg    3540
```

```
tcggcgggga cgctggggag cccgcagctg ctgatgctga gcggcgtcgg gccgcaggcg    3600
cacctggagg cgcacggcat cgaggtgatc gtggaccaac ccatggtcgg gcagggcgtc    3660
gccgacaacc cgatgaactc ggtgttcatc ccgtcgccgg tgccggtgga gctctccctg    3720
gtgcaggtcg tcggcatcac ccgctccggc agcttcatcg aggggtgag cgggtcggag     3780 ttcggcatgc cggtgtcgga cggcgcgctc cggtgggcgc gcagcttcgg gatgctgtcg    3840
ccgcagacgg ggcagctcgg cacgctgccg ccgaagcaga ggacgccgga ggcgctgcag    3900
cgggcggcgg aggcgatgat gcggctggac aggagggcgt tccggggagg cttcatcctg    3960
gagaagatcc tcgggccggt gtcctccggc cacgtcgagc tgcgaaccac cgacccgagg    4020
gcgaacccgt cggtgacgtt caactacttc gcgaggcgg aggatctgga gcggtgcgtc     4080
catggcatcg agacgatcga gcgggtgatc cagtcgcggg ccttctccaa cttcacctac    4140
gccaacgcct ccgtcgagtc catcttcacc gattccgcca acttccccgt caacctgctg    4200
ccgcgccatg tcaacgactc gcgctcgccg agcagtact gcatggacac cgtcatgacc      4260
atctggcact accacggcgg ctgccatgtc ggcgccgtcg tcgacgacga ttaccgggtg    4320
ttcggggtgc aggggctcag ggtgatcgac agctccacct tcaagtactc ccccggcacc    4380
aaccctcagg ccaccgtcat gatgctcggc aggtaactgg catcattta gctcatgaaa     4440 gtgcattgcc atgagtaaca acacactaac agtatagttt tcaatatgga cactgggcag    4500
gtatatgggt gtgaagattc agtccgagag atggaagaaa tgatgaacaa agataatttt    4560
cgtttcagga gcaaaaaaat gcatgtaatt caaggaaaag aaaatgttca actgtctta     4620 gagtttagag tagattttat ttgcacccac ttaatttta ctcttctcta gacataggtt     4680
cagtatctgc ttgttgatta tgtaaccttg aagaagcatt gcaaaacaa agcggaaact     4740 tatgttacca agggcatgac gaagaaataa atggattaga tttcattgac acttagaaaa    4800
tggaaccagc aaatcaaggc tgaaaataat tacactagaa acttattta atggctttac     4860 atgtcgctac atacttaaat caatcaaagt tgctaccaaa gccatgttcc ctaaacagag    4920
ggttccgggc tctcaaacat tcttaatctt ctatacattg ataaaagta tacataaaaa     4980 gaaaacctat taagatggaa atgttgaatt ctcttaagaa aggcataaaa aatgcagggt    5040
```

<210> SEQ ID NO 5
<211> LENGTH: 1761
<212> TYPE: DNA
<213> ORGANISM: Oryza sativa

<400> SEQUENCE: 5

```
atggcagcac ttggccgcgc gagctcgtcg gcgccggtgc ttgccgccgc cgccgccgtg     60
ctcctctcgc tctgcctcgc cgcgctctcg gaagagcaag agcaactgga gaacctgcgg    120
ttcgtgcggc acgcgcagga cgcgccgctg gtgtcgagct acaactacat cgtcatcggc    180
ggcggcacgg cggggtgccc gctggcggcg acgctgtcgg agcactcgcg cgtgctgctg    240
ctggagcgcg gcggcctgcc gtacgccaac atgtcgagcg agcagcactt cacggacgcg    300
ctggccgaca cgtcgccggc gtcgccggcg cagcggttca tctcggagga cggcgtggtg    360
aacgcccggg cgcgggtgct cggcggcggg agctgcctca cgccgggtt ctacacgcgg     420 gcgagcaacg agtacgtgcg cgcctccggg tgggacgcgc ggctggtgaa ctcgtcgtac    480
cggtgggtgg agcgctcgct ggtgttccgc cccgacgtgc cgccgtggca ggcggcgctc    540
cgcgacgcgc tgctcgaggt cggcgtcacg cccgacaacg gcttcaccct cgaccacgtc    600
```

```
accggcacca agatcggcgg caccatcttc gacaactccg gccagcgcca caccgccgcc    660
gacttcctcc gccacgcccg ccccgcggc ctcaccgtcc tcctctacgc caccgtctcc    720
cgtatcctct tcaaaagcca agacggggtg ccgtacccgg tggcgtacgg ggtggtgttc    780
tcggacccgc tggggtgca gcaccgggtg tacctccgcg acggcgacaa gaacgaggtg    840
atcgtgtcgg cggggacgct ggggagcccg cagctgctga tgctgagcgg cgtcgggccg    900
caggcgcacc tggaggcgca cggcatcgag gtgatcgtgg accaacccat ggtcgggcag    960
ggcgtcgccg acaacccgat gaactcggtg ttcatcccgt cgccggtgcc ggtggagctc   1020
tccctggtgc aggtcgtcgg catcaccgc tccggcagct tcatcgaggg ggtgagcggg   1080
tcggagttcg gcatgccggt gtcggacggc gcgctccggt gggcgcgcag cttcgggatg   1140
ctgtcgccgc agacggggca gctcggcacg ctgccgccga gcagaggac gccggaggcg   1200
ctgcagcggg cggcggaggc gatgatgcgg ctggacagga gggcgttccg gggaggcttc   1260
atcctggaga gatcctcgg gccggtgtcc tccggccacg tcgagctgcg aaccaccgac   1320
ccgagggcga acccgtcggt gacgttcaac tacttccgcg aggcagagga tctggagcgg   1380
tgcgtccatg gcatcgagac gatcgagcgg gtgatccagt cgcgggcctt ctccaacttc   1440
acctacgcca acgcctccgt cgagtccatc ttcaccgatt ccgccaactt ccccgtcaac   1500
ctgctgccgc gccatgtcaa cgactcgcgc tcgccggagc agtactgcat ggacaccgtc   1560
atgaccatct ggcactacca cggcggctgc catgtcggcg ccgtcgtcga cgacgattac   1620
cgggtgttcg gggtgcaggg gctcaggggtg atcgacagct ccaccttcaa gtactcccc   1680
ggcaccaacc ctcaggccac cgtcatgatg ctcggcaggt atatgggtgt gaagattcag   1740
tccgagagat ggaagaaatg a                                            1761
```

<210> SEQ ID NO 6
<211> LENGTH: 586
<212> TYPE: PRT
<213> ORGANISM: Oryza sativa

<400> SEQUENCE: 6

```
Met Ala Ala Leu Gly Arg Ala Ser Ser Ala Pro Val Leu Ala Ala
1               5                   10                  15

Ala Ala Ala Val Leu Leu Ser Leu Cys Leu Ala Ala Leu Ser Glu Glu
            20                  25                  30

Gln Glu Gln Leu Glu Asn Leu Arg Phe Val Arg His Ala Gln Asp Ala
        35                  40                  45

Pro Leu Val Ser Ser Tyr Asn Tyr Ile Val Ile Gly Gly Gly Thr Ala
    50                  55                  60

Gly Cys Pro Leu Ala Ala Thr Leu Ser Glu His Ser Arg Val Leu Leu
65                  70                  75                  80

Leu Glu Arg Gly Gly Leu Pro Tyr Ala Asn Met Ser Ser Glu Gln His
                85                  90                  95

Phe Thr Asp Ala Leu Ala Asp Thr Ser Pro Ala Ser Pro Ala Gln Arg
            100                 105                 110

Phe Ile Ser Glu Asp Gly Val Val Asn Ala Arg Ala Arg Val Leu Gly
        115                 120                 125

Gly Gly Ser Cys Leu Asn Ala Gly Phe Tyr Thr Arg Ala Ser Asn Glu
    130                 135                 140

Tyr Val Arg Ala Ser Gly Trp Asp Ala Arg Leu Val Asn Ser Ser Tyr
145                 150                 155                 160

Arg Trp Val Glu Arg Ser Leu Val Phe Arg Pro Asp Val Pro Pro Trp
```

-continued

```
                165                 170                 175
Gln Ala Ala Leu Arg Asp Ala Leu Leu Glu Val Gly Val Thr Pro Asp
                180                 185                 190

Asn Gly Phe Thr Phe Asp His Val Thr Gly Thr Lys Ile Gly Gly Thr
                195                 200                 205

Ile Phe Asp Asn Ser Gly Gln Arg His Thr Ala Ala Asp Phe Leu Arg
210                 215                 220

His Ala Arg Pro Arg Gly Leu Thr Val Leu Leu Tyr Ala Thr Val Ser
225                 230                 235                 240

Arg Ile Leu Phe Lys Ser Gln Asp Gly Val Pro Tyr Pro Val Ala Tyr
                245                 250                 255

Gly Val Val Phe Ser Asp Pro Leu Gly Val Gln His Arg Val Tyr Leu
                260                 265                 270

Arg Asp Gly Asp Lys Asn Glu Val Ile Val Ser Ala Gly Thr Leu Gly
                275                 280                 285

Ser Pro Gln Leu Leu Met Leu Ser Gly Val Gly Pro Gln Ala His Leu
                290                 295                 300

Glu Ala His Gly Ile Glu Val Ile Val Asp Gln Pro Met Val Gly Gln
305                 310                 315                 320

Gly Val Ala Asp Asn Pro Met Asn Ser Val Phe Ile Pro Ser Pro Val
                325                 330                 335

Pro Val Glu Leu Ser Leu Val Gln Val Val Gly Ile Thr Arg Ser Gly
                340                 345                 350

Ser Phe Ile Glu Gly Val Ser Gly Ser Glu Phe Gly Met Pro Val Ser
                355                 360                 365

Asp Gly Ala Leu Arg Trp Ala Arg Ser Phe Gly Met Leu Ser Pro Gln
                370                 375                 380

Thr Gly Gln Leu Gly Thr Leu Pro Pro Lys Gln Arg Thr Pro Glu Ala
385                 390                 395                 400

Leu Gln Arg Ala Ala Glu Ala Met Met Arg Leu Asp Arg Arg Ala Phe
                405                 410                 415

Arg Gly Gly Phe Ile Leu Glu Lys Ile Leu Gly Pro Val Ser Ser Gly
                420                 425                 430

His Val Glu Leu Arg Thr Thr Asp Pro Arg Ala Asn Pro Ser Val Thr
                435                 440                 445

Phe Asn Tyr Phe Arg Glu Ala Glu Asp Leu Glu Arg Cys Val His Gly
                450                 455                 460

Ile Glu Thr Ile Glu Arg Val Ile Gln Ser Arg Ala Phe Ser Asn Phe
465                 470                 475                 480

Thr Tyr Ala Asn Ala Ser Val Glu Ser Ile Phe Thr Asp Ser Ala Asn
                485                 490                 495

Phe Pro Val Asn Leu Leu Pro Arg His Val Asn Asp Ser Arg Ser Pro
                500                 505                 510

Glu Gln Tyr Cys Met Asp Thr Val Met Thr Ile Trp His Tyr His Gly
                515                 520                 525

Gly Cys His Val Gly Ala Val Asp Asp Tyr Arg Val Phe Gly
                530                 535                 540

Val Gln Gly Leu Arg Val Ile Asp Ser Ser Thr Phe Lys Tyr Ser Pro
545                 550                 555                 560

Gly Thr Asn Pro Gln Ala Thr Val Met Met Leu Gly Arg Tyr Met Gly
                565                 570                 575

Val Lys Ile Gln Ser Glu Arg Trp Lys Lys
                580                 585
```

<210> SEQ ID NO 7
<211> LENGTH: 1767
<212> TYPE: DNA
<213> ORGANISM: Oryza sativa

<400> SEQUENCE: 7

| | | |
|---|---|---|
| atggcagcac ttggccgcgc gagctcgtcg gcgccggtgc ttgccgccgc cgccgccgcc | 60 |
| gccgtgctcc tctcgctctg cctcgccgcg ctctcggaag agcaagagca actggagaac | 120 |
| ctgcggttcg tgcggcacgc gcaggacgcg ccgctggtgt cgagctacaa ctacatcgtc | 180 |
| atcgccggcg gcacggcggg cgtgcccgct gcggcgacgc tgtcggagca ctcgcgcgtg | 240 |
| ctgctgctgg agcgcggcgg cctgccgtac gccaacatgt cgagcgagca gcacttcacg | 300 |
| gacgcgctgg ccgacacgtc gccggcgtcg cggcgcagcg ggttcatctc ggaggacggc | 360 |
| gtggtgaacg cccgggcgcg ggtgctcggc ggcgggagct gcctcaacgc cgggttctac | 420 |
| acgcgggcga gcaacgagta cgtgcgcgcc gccgggtggg acgcgcggct ggtgaactcg | 480 |
| tcgtaccggt gggtggagcg ctcgctggtg ttccgccccg acgtgccgcc gtggcaggcg | 540 |
| gcgctccgcg acgcgctgct cgaggtcggc gtcacgcccg acaacggctt caccttcgac | 600 |
| cacgtcaccg gcaccaagat cggcggcacc atcttcgaca actccggcca gcgccacacc | 660 |
| gccgccgact cctccgcca cgccgcccc gcggcctca ccgtcctcct ctacgccacc | 720 |
| gtctcccgta tcctcttcaa aagccaagac ggggtgccgt acccggtggc gtacggggtg | 780 |
| gtgttctcgg accgctgggg ggtgcagcac cgggtgtacc tccgcgacgg cgacaagaac | 840 |
| gaggtgatcg tgtcggcggg gacgctgggg agcccgcagc tgctgatgct gagcggcgtc | 900 |
| gggccgcagg cgcacctgga ggcgcacggc atcgaggtga tcgtggacca acccatggtc | 960 |
| gggcagggcg tcgccgacaa cccgatgaac tcggtgttca tcccgtcgcc ggtgccggtg | 1020 |
| gagctctccc tggtgcaggt cgtcggcatc acccgctccg gcagcttcat cgaggggggtg | 1080 |
| agcgggtcgg agttcggcat gccggtgtcg gacggcgcgc tccggtgggc gcgcagcttc | 1140 |
| gggatgctgt cgccgcagac ggggcagctc ggcacgctgc cgccgaagca gaggacgccg | 1200 |
| gaggcgctgc agcgggcggc ggaggcgatg atgcggctgg acaggagggc gttccgggga | 1260 |
| ggcttcatcc tggagaagat cctcgggccg gtgtcctccg ccacgtcga gctgcgaacc | 1320 |
| accgaccccga gggcgaaccc gtcggtgacg ttcaactact ccgcgaggc ggaggatctg | 1380 |
| gagcggtgcg tccatggcat cgagacgatc gagcgggtga tccagtcgcg ggccttctcc | 1440 |
| aacttcacct acgccaacgc ctccgtcgag tccatcttca ccgattccgc caacttcccc | 1500 |
| gtcaacctgc tgccgcgcca tgtcaacgac tcgcgctcgc cggagcagta ctgcatggac | 1560 |
| accgtcatga ccatctggca ctaccacggc ggctgccatg tcggcgccgt cgtcgacgac | 1620 |
| gattaccggg tgttcggggt gcaggggctc agggtgatcg acagctccac cttcaagtac | 1680 |
| tcccccgaca ccaaccctca ggccaccgtc atgatgctcg gcaggtatat gggtgtgaag | 1740 |
| attcagtccg agagatggaa gaaatga | 1767 |

<210> SEQ ID NO 8
<211> LENGTH: 588
<212> TYPE: PRT
<213> ORGANISM: Oryza sativa

<400> SEQUENCE: 8

Met Ala Ala Leu Gly Arg Ala Ser Ser Ser Ala Pro Val Leu Ala Ala
1               5                   10                  15

-continued

```
Ala Ala Ala Ala Ala Val Leu Leu Ser Leu Cys Leu Ala Ala Leu Ser
                20                  25                  30
Glu Glu Gln Glu Gln Leu Glu Asn Leu Arg Phe Val Arg His Ala Gln
         35                  40                  45
Asp Ala Pro Leu Val Ser Ser Tyr Asn Tyr Ile Val Ile Gly Gly Gly
 50                  55                  60
Thr Ala Gly Cys Pro Leu Ala Ala Thr Leu Ser Glu His Ser Arg Val
 65                  70                  75                  80
Leu Leu Leu Glu Arg Gly Gly Leu Pro Tyr Ala Asn Met Ser Ser Glu
                 85                  90                  95
Gln His Phe Thr Asp Ala Leu Ala Asp Thr Ser Pro Ala Ser Pro Ala
            100                 105                 110
Gln Arg Phe Ile Ser Glu Asp Gly Val Val Asn Ala Arg Ala Arg Val
            115                 120                 125
Leu Gly Gly Gly Ser Cys Leu Asn Ala Gly Phe Tyr Thr Arg Ala Ser
130                 135                 140
Asn Glu Tyr Val Arg Ala Ala Gly Trp Asp Ala Arg Leu Val Asn Ser
145                 150                 155                 160
Ser Tyr Arg Trp Val Glu Arg Ser Leu Val Phe Arg Pro Asp Val Pro
                165                 170                 175
Pro Trp Gln Ala Ala Leu Arg Asp Ala Leu Leu Glu Val Gly Val Thr
            180                 185                 190
Pro Asp Asn Gly Phe Thr Phe Asp His Val Thr Gly Thr Lys Ile Gly
            195                 200                 205
Gly Thr Ile Phe Asp Asn Ser Gly Gln Arg His Thr Ala Ala Asp Phe
        210                 215                 220
Leu Arg His Ala Arg Pro Arg Gly Leu Thr Val Leu Leu Tyr Ala Thr
225                 230                 235                 240
Val Ser Arg Ile Leu Phe Lys Ser Gln Asp Gly Val Pro Tyr Pro Val
                245                 250                 255
Ala Tyr Gly Val Val Phe Ser Asp Pro Leu Gly Val Gln His Arg Val
            260                 265                 270
Tyr Leu Arg Asp Gly Asp Lys Asn Glu Val Ile Val Ser Ala Gly Thr
        275                 280                 285
Leu Gly Ser Pro Gln Leu Leu Met Leu Ser Gly Val Gly Pro Gln Ala
        290                 295                 300
His Leu Glu Ala His Gly Ile Glu Val Ile Val Asp Gln Pro Met Val
305                 310                 315                 320
Gly Gln Gly Val Ala Asp Asn Pro Met Asn Ser Val Phe Ile Pro Ser
                325                 330                 335
Pro Val Pro Val Glu Leu Ser Leu Val Gln Val Gly Ile Thr Arg
            340                 345                 350
Ser Gly Ser Phe Ile Glu Gly Val Ser Gly Ser Glu Phe Gly Met Pro
        355                 360                 365
Val Ser Asp Gly Ala Leu Arg Trp Ala Arg Ser Phe Gly Met Leu Ser
        370                 375                 380
Pro Gln Thr Gly Gln Leu Gly Thr Leu Pro Pro Lys Gln Arg Thr Pro
385                 390                 395                 400
Glu Ala Leu Gln Arg Ala Ala Glu Ala Met Met Arg Leu Asp Arg Arg
                405                 410                 415
Ala Phe Arg Gly Gly Phe Ile Leu Glu Lys Ile Leu Gly Pro Val Ser
            420                 425                 430
```

Ser Gly His Val Glu Leu Arg Thr Thr Asp Pro Arg Ala Asn Pro Ser
                435                 440                 445

Val Thr Phe Asn Tyr Phe Arg Glu Ala Glu Asp Leu Glu Arg Cys Val
        450                 455                 460

His Gly Ile Glu Thr Ile Glu Arg Val Ile Gln Ser Arg Ala Phe Ser
465                 470                 475                 480

Asn Phe Thr Tyr Ala Asn Ala Ser Val Glu Ser Ile Phe Thr Asp Ser
                485                 490                 495

Ala Asn Phe Pro Val Asn Leu Leu Pro Arg His Val Asn Asp Ser Arg
            500                 505                 510

Ser Pro Glu Gln Tyr Cys Met Asp Thr Val Met Thr Ile Trp His Tyr
        515                 520                 525

His Gly Gly Cys His Val Gly Ala Val Val Asp Asp Asp Tyr Arg Val
530                 535                 540

Phe Gly Val Gln Gly Leu Arg Val Ile Asp Ser Ser Thr Phe Lys Tyr
545                 550                 555                 560

Ser Pro Asp Thr Asn Pro Gln Ala Thr Val Met Met Leu Gly Arg Tyr
                565                 570                 575

Met Gly Val Lys Ile Gln Ser Glu Arg Trp Lys Lys
            580                 585

<210> SEQ ID NO 9
<211> LENGTH: 949
<212> TYPE: DNA
<213> ORGANISM: Oryza sativa

<400> SEQUENCE: 9
aaaacacaaa aaaagaaac caaccgtctt aaaacttaca actttaccat tcggcaatac        60
aactgcaatg ggccaagaag ttaatttaaa gttaagagca aattcatttg gaccaccttt       120
tgttacagat gcttcacttt ggaccacata ccacccatct ctcttctcga gcatgaacaa       180
tctcgattac attggctcct actcatcaat aaactctcac atatatatgt aaaaccattc       240
atcggtatat gacaagttat atatggataa agagttgag gatgatccaa atgtcacaa         300 aggtaagaat aataaccggt ataaagtgag aacatcgata acatcgcta ataaaagttc        360 gtctatagta aaatttactc taaaattaaa tcacctaata ttttaatatt ttttgtaca        420 aatggaccgt tcaatggggg ctttatcaga tttagttgag atgcatacat ggtaagcacc      480
gtcataatct tgcccaagag ctgacccaac tcattaaaat tacgcttctt ttacgactta       540
ataaatcaag aagaaccat tgaaatccag cctgccccga ctgtctcgta acagaaaaat        600
aactaagcaa cgactaaatt atgattttaa aatggcaaaa atatcaaagc acgttcgaaa      660
caatcgcaag attggcaagt aaactctcct gcttgcttgc tcacaaccac atcagatcat      720
tgatcaatgt ttcatcagct catcacttct gcatgcatgt tatattcttc tcagggctcc     780
tccacaattt acaaagctgc tcgaagatct tctttgcagt gcaaagcaat ctgcaagatt     840
attcaagaca tctactcttg atctaccatt gagctaactc cggatatata aacagaccga     900
acgtttcgtc ccaggggaat gtgaaagtta gcgaatttgc ccggcgaaa                  949

<210> SEQ ID NO 10
<211> LENGTH: 2285
<212> TYPE: DNA
<213> ORGANISM: Hordeum vulgare

<400> SEQUENCE: 10
acgatgaacc aagcaggccc ttagaaaaaa tatagtgcac gcgcaaaagc gtctcaagat        60

```
tggccagtaa acccctcgcat ttgatatact ccttccgtct aaaaacaaag ctcatcactt    120
ttgcatttcg caaccaatgc actgcatttg atataaccat tcccttcta tagtaacaca      180 attttatggg ctcctcgcgg ctgttctttg cactgtaatt atttaacaca tctaccctcg    240
atctacccgc ttgctaactc caggtttata aaccaagcga acttttcgcg tccctgaagc    300
gtaaaggatg ctgagctcgc cggcgcaaat ggcacttggc cgcgcgagat cgccggcgct    360
ggtgctagtc gccgccgtcc ttggctcgct ctgcatcgtc gcactctcgg aggatggtgc    420
gtatgctcac ctgcatggtt tttctggggg gtttggacat cggctacgtg cgtgtgtgtt    480
ctgtcatgat cgttggacat tgtgatgacc aaaatggtgt gccgtgcgtg tgtgcagagc    540
aactggagaa cctgcggttc gtgcagcacg cgcaggacgc gccgctggtg tcgcacttca    600
actacatcgt ggtcggcggc ggcacgtccg ggtgcccgct ggcggcgacg ctgtcggagc    660
actcgcgggt gctcctgctg gagcgcgggg gcctccccta ccgcaacatg tcgaaccagg    720
agcacttcac ggacgcgctg gccgacacgt cgctggcgtc cccggcgcag cggttcatct    780
cgacggacgg cgtggtgaac gcgcgggcgc gggtgctggg cggcgggagc tgcctcaacg    840
ccgggttcta cacgcgggcc agcaacgagt acgtgcgcac ggccgggtgg gacgccaggc    900
tggtgaactc gtcgtaccgg tgggtggagc gcgcgctggt gttccggccc gacgtgccgc    960
cgtggcaggc cgcgctccgg gacgcgctgc tggaggccgg cgtcaccccg gataacggat   1020
tcaccttcga ccacgtgacg gggaccaaga tcggcggcac catcttcgac aacaacgggc   1080
agcggcacac cgccgccgac ttcctccggc acgcccggcc gcgggggctc accgtggtgc   1140
tctacgccac ggtgtcgcgg atcctgttca ggagccagga gggggtgccg tacccggtgg   1200 cgtacgggt ggtgttcgcg gacccgctgg gggtgcagca ccgggtgtac ctccgggacg    1260
gggccaagaa cgaggtgatc ctgtcggcgg ggacgctggg gagcccgcag ctgctgatgc   1320
tgagcggcgt cggcccgcag gcgcacctgg aggcgcacgg catccaggtg ctggtggacc   1380
agcccatggt cgggcagggc gtggccgaca acccatgaa ctcggtcttc atcccgtcgc     1440
ccgtgcccgt ggggctctcc ctggtgcagg tggtcgggat caccaagtcc ggcagcttca   1500
tcgagggcgt gagcggctcc gagttcggca tcccggtgtc ggacggcgcc cgccgcctcg   1560
ccaacttcgg cctcttctcg ccccagaccg ggcagctcgg cacgctgccg ccgggccaga   1620
ggacgccgga ggcgctgcag cgggcggcgg aggcgatgag gcggctggac cggcgggcgt   1680
tccggggcgg cttcatcctg gagaagatcc tggggccggt gtcgacgggg cacatcgagc   1740
tgcgcaccac cgaccgcgc gccaacccgg ccgtcacctt caactacttc caggaggcgg    1800
aggacctgga gcggtgcgtg cggggatcc agaccatcga gcggtgatc cagtcgcgcg     1860 cattctccaa cttcacctac gccaacacca ccgtcgagtc catcttcacc gactcggcca   1920
acttccccgt caaccttctg ccgcggcacg tcaacgactc ccgctcgccg gagcagtact   1980
gcagggagac cgtcatgacc atctggcact accacgccgg ctgccacgtc ggagccgtcg   2040
tcgacgacaa ctaccgggtg ttcggggtgg gggggctcag ggtcatcgac agctccacct   2100
tcaggtactc ccccggcacc aaccccgcagg ccaccgtcat gatgctcggc aggtaaacac   2160
cagacccttg caattatact gatctgaatg aatgaactcg actaacacga acgttataaa    2220
tctggtatgt acaggtatat gggcataaag attcaggccg agagatggag gaaatgatat    2280
ttcag                                                                2285
```

<210> SEQ ID NO 11

<211> LENGTH: 1767
<212> TYPE: DNA
<213> ORGANISM: Hordeum vulgare

<400> SEQUENCE: 11

```
atgctgagct cgccggcgca aatggcactt ggccgcgcga gatcgccggc gctggtgcta      60
gtcgccgccg tccttggctc gctctgcatc gtcgcactct cggaggatga gcaactggag     120
aacctgcgt tcgtgcagca cgcgcaggac gcgccgctgg tgtcgcactt caactacatc     180
gtggtcggcg gcggcacgtc cgggtgcccg ctggcggcga cgctgtcgga gcactcgcgg     240
gtgctcctgc tggagcgcgg gggcctcccc taccgcaaca tgtcgaacca ggagcacttc     300
acggacgcgc tggccgacac gtcgctggcg tccccggcgc agcggttcat ctcgacggac     360
ggcgtggtga cgcgcgggc gcgggtgctg gcggcggga gctgcctcaa cgccgggttc     420
tacacgcggg ccagcaacga gtacgtgcgc acggccgggt gggacgccag gctggtgaac     480
tcgtcgtacc ggtgggtgga gcgcgcgctg gtgttccggc ccgacgtgcc gccgtggcag     540
gccgcgctcc gggacgcgct gctggaggcc ggcgtcaccc cggacaacgg attcaccttc     600
gaccacgtga cggggaccaa gatcggcggc accatcttcg acaacaacgg gcagcggcac     660
accgccgccg acttcctccg gcacgcccgg ccgcgggggc tcaccgtggt gctctacgcc     720
acggtgtcgc ggatcctgtt caggagccag gaggggtgc cgtacccggt ggcgtacggg     780
gtggtgttcg cggacccgct gggggtgcag caccgggtgt acctccggga cggggccaag     840
aacgaggtga tcctgtcggc ggggacgctg gggagcccgc agctgctgat gctgagcggc     900
gtcggcccgc aggcgcacct ggaggcgcac ggcatccagg tgctggtgga ccagcccatg     960
gtcgggcagg gcgtggccga caaccccatg aactcggtct tcatcccgtc gcccgtgccc    1020
gtggggctct ccctggtgca ggtggtcggg atcaccaagt ccggcagctt catcgagggc    1080
gtgagcggct ccgagttcgg catcccggtg tcggacggcg cccgccgcct cgccaacttc    1140
ggcctcttct cgccccagac cgggcagctc ggcacgctgc cgccgggcca gaggacgccg    1200
gaggcgctgc agcgggcggc ggaggcgatg aggcggctgg accggcgggc gttccggggc    1260
ggcttcatcc tggagaagat cctggggccg gtgtcgacgg gcacatcga gctgcgcacc    1320
accgacccgc gcgccaaccc ggccgtcacc ttcaactact ccaggaggc ggaggacctg    1380
gagcggtgcg tgcgggggat ccagaccatc gagcgggtga tccagtcgcg cgcattctcc    1440
aacttcacct acgccaacac caccgtcgag tccatcttca ccgactcggc caacttcccc    1500
gtcaacctgc tgccgcggca cgtcaacgac tcccgctcgc cggagcagta ctgcagggag    1560
accgtcatga ccatctggca ctaccacggc ggctgccacg tcggagccgt cgtcgacgac    1620
aactaccggg tgttcggggt gggggggctc agggtcatcg acagctccac cttcaggtac    1680
tccccccggca ccaacccgca ggccaccgtc atgatgctcg gcaggtatat gggcataaag    1740
attcaggccg agagatggag gaaatga                                         1767
```

<210> SEQ ID NO 12
<211> LENGTH: 588
<212> TYPE: PRT
<213> ORGANISM: Hordeum vulgare

<400> SEQUENCE: 12

```
Met Leu Ser Ser Pro Ala Gln Met Ala Leu Gly Arg Ala Arg Ser Pro
1               5                   10                  15

Ala Leu Val Leu Val Ala Ala Val Leu Gly Ser Leu Cys Ile Val Ala
            20                  25                  30
```

```
Leu Ser Glu Asp Glu Gln Leu Glu Asn Leu Arg Phe Val Gln His Ala
        35                  40                  45
Gln Asp Ala Pro Leu Val Ser His Phe Asn Tyr Ile Val Val Gly Gly
    50                  55                  60
Gly Thr Ser Gly Cys Pro Leu Ala Ala Thr Leu Ser Glu His Ser Arg
65                  70                  75                  80
Val Leu Leu Leu Glu Arg Gly Gly Leu Pro Tyr Arg Asn Met Ser Asn
                85                  90                  95
Gln Glu His Phe Thr Asp Ala Leu Ala Asp Thr Ser Leu Ala Ser Pro
                100                 105                 110
Ala Gln Arg Phe Ile Ser Thr Asp Gly Val Val Asn Ala Arg Ala Arg
            115                 120                 125
Val Leu Gly Gly Gly Ser Cys Leu Asn Ala Gly Phe Tyr Thr Arg Ala
        130                 135                 140
Ser Asn Glu Tyr Val Arg Thr Ala Gly Trp Asp Ala Arg Leu Val Asn
145                 150                 155                 160
Ser Ser Tyr Arg Trp Val Glu Arg Ala Leu Val Phe Arg Pro Asp Val
                165                 170                 175
Pro Pro Trp Gln Ala Ala Leu Arg Asp Ala Leu Leu Glu Ala Gly Val
                180                 185                 190
Thr Pro Asp Asn Gly Phe Thr Phe Asp His Val Thr Gly Thr Lys Ile
            195                 200                 205
Gly Gly Thr Ile Phe Asp Asn Asn Gly Gln Arg His Thr Ala Ala Asp
        210                 215                 220
Phe Leu Arg His Ala Arg Pro Arg Gly Leu Thr Val Val Leu Tyr Ala
225                 230                 235                 240
Thr Val Ser Arg Ile Leu Phe Arg Ser Gln Glu Gly Val Pro Tyr Pro
                245                 250                 255
Val Ala Tyr Gly Val Val Phe Ala Asp Pro Leu Gly Val Gln His Arg
                260                 265                 270
Val Tyr Leu Arg Asp Gly Ala Lys Asn Glu Val Ile Leu Ser Ala Gly
            275                 280                 285
Thr Leu Gly Ser Pro Gln Leu Leu Met Leu Ser Gly Val Gly Pro Gln
        290                 295                 300
Ala His Leu Glu Ala His Gly Ile Gln Val Leu Val Asp Gln Pro Met
305                 310                 315                 320
Val Gly Gln Gly Val Ala Asp Asn Pro Met Asn Ser Val Phe Ile Pro
                325                 330                 335
Ser Pro Val Pro Val Gly Leu Ser Leu Val Gln Val Val Gly Ile Thr
                340                 345                 350
Lys Ser Gly Ser Phe Ile Glu Gly Val Ser Gly Ser Glu Phe Gly Ile
            355                 360                 365
Pro Val Ser Asp Gly Ala Arg Arg Leu Ala Asn Phe Gly Leu Phe Ser
        370                 375                 380
Pro Gln Thr Gly Gln Leu Gly Thr Leu Pro Pro Gly Gln Arg Thr Pro
385                 390                 395                 400
Glu Ala Leu Gln Arg Ala Ala Glu Ala Met Arg Arg Leu Asp Arg Arg
                405                 410                 415
Ala Phe Arg Gly Gly Phe Ile Leu Glu Lys Ile Leu Gly Pro Val Ser
                420                 425                 430
Thr Gly His Ile Glu Leu Arg Thr Thr Asp Pro Arg Ala Asn Pro Ala
            435                 440                 445
```

Val Thr Phe Asn Tyr Phe Gln Glu Ala Glu Asp Leu Glu Arg Cys Val
            450                 455                 460

Arg Gly Ile Gln Thr Ile Glu Arg Val Ile Gln Ser Arg Ala Phe Ser
465                 470                 475                 480

Asn Phe Thr Tyr Ala Asn Thr Thr Val Glu Ser Ile Phe Thr Asp Ser
                485                 490                 495

Ala Asn Phe Pro Val Asn Leu Leu Pro Arg His Val Asn Asp Ser Arg
            500                 505                 510

Ser Pro Glu Gln Tyr Cys Arg Glu Thr Val Met Thr Ile Trp His Tyr
        515                 520                 525

His Gly Gly Cys His Val Gly Ala Val Val Asp Asp Asn Tyr Arg Val
530                 535                 540

Phe Gly Val Gly Gly Leu Arg Val Ile Asp Ser Ser Thr Phe Arg Tyr
545                 550                 555                 560

Ser Pro Gly Thr Asn Pro Gln Ala Thr Val Met Met Leu Gly Arg Tyr
                565                 570                 575

Met Gly Ile Lys Ile Gln Ala Glu Arg Trp Arg Lys
            580                 585

<210> SEQ ID NO 13
<211> LENGTH: 1964
<212> TYPE: DNA
<213> ORGANISM: Sorghum bicolor

<400> SEQUENCE: 13

```
atggcgcctg ggcttgcgag ctcggccgcg ctgggggttt tggccatcgt tcttggctcc      60
tcgtgcctcg tcgcgctctc ggaggatggt tcgtgccgtg ccggactgca tgccgtgaat     120
atggtcatgc gtttttgttt tcttttggat tttctgcact tctgcaaacg tctgaatcgg     180
tgcatggtca tatgtatgtg cagagccact ggagaacctg cggttcgttc gccacgcgca     240
ggacgcgccg ctggtgtcgc aatacaacta catcgtcatc ggcggcggca cggcgggctg     300
cccgctggcg gcgacgctgt cggagcactc ccgcgtgctg ctcctggagc gcggaggcct     360
cccctaccgc aacatgtcca accagcagca cttcacggag cgctggcgg acacgtcccc     420
ggcgtcgccc gcgcagcggt tcatctccga ggacggcgtg gtgaacgcgc gggcgcgggt     480
gctgggcggc gggagctgcc tcaacgccgg cttctacacg cgggccagca cgactacgt     540
gcgcgccgcc gggtgggaca cccgcctcgt caactcctcg taccactggg tggagcgcgc     600
gctcgtgttc cgcccggacg tgccccatg gcaggccgcg ctccgcgacg cgctgctgga     660
ggccggcgtc accccgaca acggcttcac cttcgaccac gtcccgggca ccaagatcgg     720
cggcaccatc ttcgacagca gcgggcagcg gcacaccgcc gccgacttcc tccgccacgc     780
gcggcccagg ggcctcaccg tgttcctcta cgctaccgtc tcgaggatcc tcttcaggca     840
gcaagagggc gtgccgtacc cggtggcgta cggcgtggtg ttcacggacc cgctgggcgt     900
gcagcaccgg gtgtacctcc gcgacggcgg caagaacgag gtgatcctgt ccgcggggac     960
gctggggagc ccgcagctgc tgatgctgag cggcgtcgga ccgcaggcgc acctggaggc    1020
gcacggcatc caggtgctgg tcgaccagcc catggtcggg cagggcgtgg ccgacaaccc    1080
catgaactcg gtgttcatcc cgtcgccggt gccgtcacg ctctcgctcg tgcaggtcgt    1140
cgggatcacc cggttcggca gcttcatcga gggcgtcagc ggctccgagt tcggcatccc    1200
cgtctccgac ggcgcccgcc gcctagctcg caacttcggc ctcttctctc tcaggtgtg    1260
gtcggtcggt ccggtcggtg cttcgttcca tactgacagc aacatagccg ccggaaatga    1320
```

```
aatgtactga ctactgacgg atcatcttgc ggcagaccgg gcagctgggc acgctgccgc   1380
cgaagcagag aacccggag gctctggagc gggcggcgga ggcgatgcgg cggctggaca    1440
ggcgggcgtt ccggggcggc ttcatcctgg agaagatcct gggcccggtg tcgtcgggc    1500 acatcgagct gcggtccgcc gacccgcgcg cgaaccggc ggtgacgttc aactacttcc    1560
aggagtcgga ggacctggag cggtgcgtgc acggcatcca cgatcgag cgggtgatcc     1620 agtcccgggc cttcgccaac ttcacctacg ccaacgcgtc cgtggagtcc atcttcaccg   1680
actccgccaa cttccccgtc aacctcctgc cgcggcacgt caacgactcc cggacgcccg   1740
agcagtactg cagggacacc gtcatgacca tctggcacta ccacggcgga tgccaggtcg   1800
gcgccgtcgt cgacgacgat taccgggtgt tcggcgtgca gcggctcagg gtgatcgaca   1860
gctccacgtt caagtactcc ccgggggacca acccgcaggc caccgtcatg atgctcggaa   1920
ggtatatggg ggtgaaaatt caggcccaga gatggaggaa atga                    1964
```

<210> SEQ ID NO 14
<211> LENGTH: 1749
<212> TYPE: DNA
<213> ORGANISM: Sorghum bicolor

<400> SEQUENCE: 14

```
atggcgcctg ggcttgcgag ctcggccgcg ctggggggttt tggccatcgt tcttggctcc   60
tcgtgcctcg tcgcgctctc ggaggatgag ccactggaga acctgcggtt cgttcgccac   120
gcgcaggacg cgccgctggt gtcgcaatac aactacatcg tcatcggcgg cggcacggcg   180
ggctgcccgc tggcggcgac gctgtcggag cactcccgcg tgctgctcct ggagcgcgga   240
ggcctcccct accgcaacat gtccaaccag cagcacttca cggaggcgct ggcggacacg   300
tccccggcgt cgcccgcgca gcggttcatc tccgaggacg cgtggtgaa cgcgcggggcg   360 cgggtgctgg gcggcgggag ctgcctcaac gccggcttct acacgcgggc cagcaacgac   420
tacgtgcgcg ccgccgggtg ggacacccgc ctcgtcaact cctcgtacca ctgggtggag   480
cgcgcgctcg tgttccgccc ggacgtgccc ccatggcagg ccgcgctccg cgacgcgctg   540
ctggaggccg gcgtcacccc cgacaacggc ttcaccttcg accacgtccc gggcaccaag   600
atcggcggca ccatcttcga cagcagcggg cagcggcaca ccgccgccga cttcctccgc   660
cacgcgcggc ccaggggcct caccgtgttc ctctacgcta ccgtctcgag gatcctcttc   720
aggcagcaag agggcgtgcc gtaccccggtg gcgtacggcg tggtgttcac ggacccgctg   780
ggcgtgcagc accgggtgta cctccgcgac ggcggcaaga acgaggtgat cctgtccgcg   840
gggacgctgg ggagcccgca gctgctgatg ctgagcggcg tcggaccgca ggcgcacctg   900
gaggcgcacg gcatccaggt gctggtcgac cagcccatgg tcgggcaggg cgtgccgac   960 aaccccatga actcggtgtt catcccgtcg ccggtgcccg tcacgctctc gctcgtgcag   1020
gtcgtcggga tcaccggtt cggcagcttc atcgagggcg tcagcggctc cgagttcggc   1080
atccccgtct ccgacggcgc ccgccgccta gctcgcaact tcggcctctt ctctcctcag   1140
accgggcagc tgggcacgct gccgccgaag cagagaaccc cggaggctct ggagcgggcg   1200
gcggaggcga tgcggcggct ggacaggcgg gcgttccggg gcggcttcat cctggagaag   1260
atcctgggcc cggtgtcgtc ggggcacatc gagctgcggt ccgccgaccc gcgcgcgaac   1320
ccggccgtga cgttcaacta cttccaggag tcggaggacc tggagcggtg cgtgcacggc   1380
atccagacga tcgagcgggt gatccagtcc cgggccttcg ccaacttcac ctacgccaac   1440
gcgtccgtgg agtccatctt caccgactcc gccaacttcc ccgtcaacct cctgccgcgg   1500
```

```
cacgtcaacg actcccggac gcccgagcag tactgcaggg acaccgtcat gaccatctgg    1560
cactaccacg gcggatgcca ggtcggcgcc gtcgtcgacg acgattaccg ggtgttcggc    1620
gtgcagcggc tcagggtgat cgacagctcc acgttcaagt actccccggg gaccaacccg    1680
caggccaccg tcatgatgct cggaaggtat atgggggtga aaattcaggc ccagagatgg    1740
aggaaatga                                                            1749
```

<210> SEQ ID NO 15
<211> LENGTH: 582
<212> TYPE: PRT
<213> ORGANISM: Sorghum bicolor

<400> SEQUENCE: 15

```
Met Ala Pro Gly Leu Ala Ser Ser Ala Ala Leu Gly Val Leu Ala Ile
1               5                   10                  15

Val Leu Gly Ser Ser Cys Leu Val Ala Leu Ser Glu Asp Glu Pro Leu
            20                  25                  30

Glu Asn Leu Arg Phe Val Arg His Ala Gln Asp Ala Pro Leu Val Ser
        35                  40                  45

Gln Tyr Asn Tyr Ile Val Ile Gly Gly Gly Thr Ala Gly Cys Pro Leu
    50                  55                  60

Ala Ala Thr Leu Ser Glu His Ser Arg Val Leu Leu Leu Glu Arg Gly
65                  70                  75                  80

Gly Leu Pro Tyr Arg Asn Met Ser Asn Gln Gln His Phe Thr Glu Ala
                85                  90                  95

Leu Ala Asp Thr Ser Pro Ala Ser Pro Ala Gln Arg Phe Ile Ser Glu
            100                 105                 110

Asp Gly Val Val Asn Ala Arg Ala Arg Val Leu Gly Gly Gly Ser Cys
        115                 120                 125

Leu Asn Ala Gly Phe Tyr Thr Arg Ala Ser Asn Asp Tyr Val Arg Ala
    130                 135                 140

Ala Gly Trp Asp Thr Arg Leu Val Asn Ser Ser Tyr His Trp Val Glu
145                 150                 155                 160

Arg Ala Leu Val Phe Arg Pro Asp Val Pro Trp Gln Ala Ala Leu
                165                 170                 175

Arg Asp Ala Leu Leu Glu Ala Gly Val Thr Pro Asp Asn Gly Phe Thr
            180                 185                 190

Phe Asp His Val Pro Gly Thr Lys Ile Gly Gly Thr Ile Phe Asp Ser
        195                 200                 205

Ser Gly Gln Arg His Thr Ala Ala Asp Phe Leu Arg His Ala Arg Pro
    210                 215                 220

Arg Gly Leu Thr Val Phe Leu Tyr Ala Thr Val Ser Arg Ile Leu Phe
225                 230                 235                 240

Arg Gln Gln Glu Gly Val Pro Tyr Pro Val Ala Tyr Gly Val Phe
                245                 250                 255

Thr Asp Pro Leu Gly Val Gln His Arg Val Tyr Leu Arg Asp Gly Gly
            260                 265                 270

Lys Asn Glu Val Ile Leu Ser Ala Gly Thr Leu Gly Ser Pro Gln Leu
        275                 280                 285

Leu Met Leu Ser Gly Val Gly Pro Gln Ala His Leu Glu Ala His Gly
    290                 295                 300

Ile Gln Val Leu Val Asp Gln Pro Met Val Gly Gln Gly Val Ala Asp
305                 310                 315                 320
```

```
Asn Pro Met Asn Ser Val Phe Ile Pro Ser Pro Val Pro Val Thr Leu
                325                 330                 335
Ser Leu Val Gln Val Val Gly Ile Thr Arg Phe Gly Ser Phe Ile Glu
            340                 345                 350
Gly Val Ser Gly Ser Glu Phe Gly Ile Pro Val Ser Asp Gly Ala Arg
        355                 360                 365
Arg Leu Ala Arg Asn Phe Gly Leu Phe Ser Pro Gln Thr Gly Gln Leu
    370                 375                 380
Gly Thr Leu Pro Pro Lys Gln Arg Thr Pro Glu Ala Leu Glu Arg Ala
385                 390                 395                 400
Ala Glu Ala Met Arg Arg Leu Asp Arg Arg Ala Phe Arg Gly Gly Phe
                405                 410                 415
Ile Leu Glu Lys Ile Leu Gly Pro Val Ser Ser Gly His Ile Glu Leu
            420                 425                 430
Arg Ser Ala Asp Pro Arg Ala Asn Pro Ala Val Thr Phe Asn Tyr Phe
        435                 440                 445
Gln Glu Ser Glu Asp Leu Glu Arg Cys Val His Gly Ile Gln Thr Ile
    450                 455                 460
Glu Arg Val Ile Gln Ser Arg Ala Phe Ala Asn Phe Thr Tyr Ala Asn
465                 470                 475                 480
Ala Ser Val Glu Ser Ile Phe Thr Asp Ser Ala Asn Phe Pro Val Asn
                485                 490                 495
Leu Leu Pro Arg His Val Asn Asp Ser Arg Thr Pro Glu Gln Tyr Cys
            500                 505                 510
Arg Asp Thr Val Met Thr Ile Trp His Tyr His Gly Gly Cys Gln Val
        515                 520                 525
Gly Ala Val Val Asp Asp Asp Tyr Arg Val Phe Gly Val Gln Arg Leu
    530                 535                 540
Arg Val Ile Asp Ser Ser Thr Phe Lys Tyr Ser Pro Gly Thr Asn Pro
545                 550                 555                 560
Gln Ala Thr Val Met Met Leu Gly Arg Tyr Met Gly Val Lys Ile Gln
                565                 570                 575
Ala Gln Arg Trp Arg Lys
            580

<210> SEQ ID NO 16
<211> LENGTH: 2585
<212> TYPE: DNA
<213> ORGANISM: Zea mays

<400> SEQUENCE: 16
ctcacagcaa attcgtctca cgcatattcg tcatccagct ccgtttaaaa tgcgtgctca      60
ttatccctca agcatgcata tactatatat gatgcagatc atatatgacc tttatacaat     120
tatcaccacc tcgattcctc gcggcacatc tttgcaccgc agaacgaccg tgcagtattt     180
tatacaaaca tctactctcg atctacccat gagctaactc caatatata agcgagccga      240 acttttctcc tatctgagca ctgctgctgc tgaaaatggc gcctgggctt gcgaactggg     300
tcgcgctggt tctgaccgtc ctccttggtc tctcgtgcct cgtcgtcgcg ctctcggagg     360
atggtttgtg ccggacttgt cacgcgctct ttggtatttc tgcagttctg caaacgtgtg     420
aattggcatg gacatgtgca gaaacactgg acaagctgcg gttcgtgcgc cacgcacagg     480
acgcgcccct ggtgtcgcag tacaactaca tcgtgatcgg cggcggcacg gcgggtgcc      540 cgctggcggc gacgctgtcg gagcactcgc gcgtgctgct cctggagcgc ggggcctcc      600
```

| | |
|---|---|
| cgtcccgcaa catgtccgac cagcagcact tcacggacgc gctggcggac acgtccccgg | 660 |
| cgtcgcccgc gcagcggttc gtgtccgagg acggcgtggt gaacgcgcgg gcccgggtgc | 720 |
| tgggcggggg cagctgcctc aacgccgggt tctacacgcg ggccagcacc gactacgtgc | 780 |
| gcgccgccgc ctgggacgcc cgcctcgtca actcgtccta ccgctgggtg gagcgcgcgc | 840 |
| tcgtgttccg ccccgccgtg cccccgtggc aggccgcgct ccgcgacgcg ctgctcgagg | 900 |
| ccggcgtcac gcccgacaac ggcttcacct tcgaccacgt cacgggcacc aagatcgggg | 960 |
| gcaccatctt cgacagcagc ggccagcgcc acaccgccgc cgacttcctc cgccacgcgc | 1020 |
| gccccagggg gctcaccgtg ttcctctacg ctaccgtctc caggatcctc ttcagacagc | 1080 |
| aaggtacgta cgtgcgtgca cggcttccgc atttttttt cgacagtgcg ggctggcacg | 1140 |
| atcgcgctct gaagcggaga atcgtgcgct gtcgacagag ggcgtgccgt acccggtggc | 1200 |
| gtacggtgtg gtgttcacgg acccgctcgg ggtgcagcac cgggtgtacc tccgggacgg | 1260 |
| cgccaagaac gaggtgatcc tgtcggcggg gacgctgggg agcccgcagc tgctgatgct | 1320 |
| gagcggcgtc ggcccgcagg cgcacctgga ggcgcacggg gtccaggtgc tggtggacca | 1380 |
| gcccatggtc gggcagggcg tggctgacaa cccgatgaac tcggtgttca tcccgtcgcc | 1440 |
| ggtgcccgtc acgctgtcgc tcgtgcaggt cgtcgggatc acccggtccg gcagcttcat | 1500 |
| cgagggcgtg agcggctccg agttcggcat ccccgtctcc gagggcgccc gtcgcctggc | 1560 |
| tcgcagcttc ggcctcttct ctcccgcagac ggggcagctg gcacgttgc cgccgaagca | 1620 |
| gagaacccca gaggccctgg agcgcgcggc ggaggcgatg cggcggctgg acaggcgggc | 1680 |
| gttccggggc ggattcatcc tggagaagat cctgggcccc gtctcctcgg ccacgtcga | 1740 |
| gctgcggtcc gccgacccgc gcgcgaaccc ggcggtgacg ttcaactact ccaggagtc | 1800 |
| ggaggacctg cagcggtgcg tgcgcggcat ccagacgatc gagcgcgtga tccagtcccg | 1860 |
| ggccttcgcc aacttcacct acgccaacgc ttccacggag tccatcttca ccgactccgc | 1920 |
| caacttcccc gtcaacctcc tgccgcggca cgtcaacgac tcccggacgc ccgagcagta | 1980 |
| ctgcagggac accgtcatga ccatctggca ttaccacggc gggtgccagg tcggcgccgt | 2040 |
| cgtggacgac gattaccggg tgttcggcgt gcagcgactg agggtgatcg acagctccac | 2100 |
| gttcaagtac tcccccggca ccaacccgca ggccaccgtc atgatgctcg aaggtatat | 2160 |
| gggtgtgaaa attcaggccg agagatggag gaaatgatcg agatttcaag tttcagcatg | 2220 |
| gtctagggac taggcctcta gctgtgataa tgaatatcaa tcaacacatc tgtaactggg | 2280 |
| taactgctct agcctctaga gtaggtttta tttttctcta gatatttttt taatctcctc | 2340 |
| tagacatact cctagcttcc gcatgttgtt ggttccattt caccacaccc ctagatgcat | 2400 |
| tgttcagcat ttcgcgggaa taatgagaat tatgctgaaa aggcatgatc gctcctcctg | 2460 |
| cctattctac agaaaattaa ataaagaacc gccatttcat caaataaacc aaaggccgtg | 2520 |
| ttctgtggat tggaagggat cgaggaagat taaatcgttt ctatttaatt ttcccttaat | 2580 |
| tttaa | 2585 |

```
<210> SEQ ID NO 17
<211> LENGTH: 2242
<212> TYPE: DNA
<213> ORGANISM: Zea mays

<400> SEQUENCE: 17
```

| | |
|---|---|
| atggcgcctg ggcttgcgaa ctgggtcgcg ctggttcgcg ctggtctga ccgtcctcct | 60 |
| tggtctctcg tgcctcgtcg tcgcgctctc ggaggatggt ttgtgatggt ttgtgccgga | 120 |

```
cttgtcacgc gctctttggt atttctgcag ttctgcaaac gtgtgaattg gcatgaattg      180
gcatggacat gtgcagaaac actggacaag ctgcggttcg tgcgccacgc acaggacgcg      240
cccctacgcg ccccctggtgt cgcagtacaa ctacatcgtg atcggcggcg gcacggcggg     300
gtgcccgctg gcggccgctg gcggcgacgc tgtcggagca ctcgcgcgtg ctgctcctgg      360
agcgcggggg cctcccgtcc cgcaacgtcc cgcaacatgt ccgaccagca gcacttcacg      420
gacgcgctgg cggacacgtc cccggcgtcg cccgccgtcg cccgcgcagc ggttcgtgtc      480
cgaggacggc gtggtgaacg cgcgggcccg ggtgctgggc ggggggtgggc gggggcagct     540
gcctcaacgc cgggttctac acgcgggcca gcaccgacta cgtgcgcgcc gccgggcgcc     600
gccggctggg acgcccgcct cgtcaactcg tcctaccgct gggtggagcg cgcgctcgtg      660
ttccgtcgtg ttccgccccg ccgtgccccc gtggcaggcc gcgctccgcg acgcgctgct      720
cgaggccggc gtcacccggc gtcacgcccg acaacggctt caccttcgac cacgtcacgg      780
gcaccaagat cggggggcacc atcttgcacc atcttcgaca gcagcggcca gcgccacacc     840
gccgccgact tcctccgcca cgcgcgcccc aggggggcccc aggggggctca ccgtgttcct    900
ctacgctacc gtctccagga tcctcttcag acagcaaggt acgtaaaggt acgtacgtgc      960
gtgcacggct tccgcatttt ttttttcgaca gtgcgggctg gcacgatcgc gctctatcgc     1020
gctctgaagc ggagaatcgt gcgctgtcga cagagggcgt gccgtacccg gtggcgtacg     1080
gtgtggtacg gtgtggtgtt cacggacccg ctcggggtgc agcaccgggt gtacctccgg     1140
gacggcgcca agaaccgcca agaacgaggt gatcctgtcg gcggggacgc tggggagccc     1200
gcagctgctg atgctgagcg gcgtcgagcg gcgtcggccc gcaggcgcac ctggaggcgc     1260
acggcgtcca ggtgctggtg gaccagccca tggtcgccca tggtcgggca gggcgtggct     1320
gacaacccga tgaactcggt gttcatcccg tcgccggtgc ccgtcggtgc ccgtcacgct     1380
gtcgctcgtg caggtcgtcg ggatcacccg gtccggcagc ttcatcgagg gcgtgcgagg     1440
gcgtgagcgg ctccgagttc ggcatccccg tctccgaggg cgcccgtcgc ctggctcgca     1500
gcttctcgca gcttcggcct cttctctccg cagacggggc agctgggcac gttgccgccg     1560
aagcagagaa ccccagagaa ccccagaggc cctggagcgc gcggcggagg cgatgcggcg     1620
gctggacagg cgggcgttcc ggggcgttcc ggggcggatt catcctggag aagatcctgg     1680
gccccgtctc ctcgggccac gtcgagctgc ggtccgctgc ggtccgccga cccgcgcgcg     1740
aacccggcgg tgacgttcaa ctacttccag gagtcggagg acctgggagg acctgcagcg     1800
gtgcgtgcgc ggcatccaga cgatcgagcg cgtgatccag tcccgggcct cgccggcct      1860
tcgccaactt cacctacgcc aacgcttcca cggagtccat cttcaccgac tccgccaact     1920
tccccccaact tccccgtcaa cctcctgccg cggcacgtca acgactcccg gacgcccgag     1980
cagtactgca gggacctgca gggacaccgt catgaccatc tggcattacc acggcgggtg     2040
ccaggtcggc gccgtcgtgg acgaccgtgg acgacgatta ccgggtgttc ggcgtgcagc     2100
gactgagggt gatcgacagc tccacgttca gtacgttca agtactcccc cggcaccaac      2160
ccgcaggcca ccgtcatgat gctcggaagg tatatgggtg tgaaagggtg tgaaaattca     2220
ggccgagaga tggaggaaat ga                                              2242
```

<210> SEQ ID NO 18
<211> LENGTH: 672
<212> TYPE: PRT
<213> ORGANISM: Zea mays

```
<400> SEQUENCE: 18

Met Ala Pro Gly Leu Ala Asn Trp Val Ala Leu Val Leu Thr Val Leu
1               5                   10                  15

Leu Gly Leu Ser Cys Leu Val Val Ala Leu Ser Glu Asp Glu Thr Leu
            20                  25                  30

Asp Lys Leu Arg Phe Val Arg His Ala Gln Asp Ala Pro Leu Val Ser
        35                  40                  45

Gln Tyr Asn Tyr Ile Val Ile Gly Gly Gly Thr Ala Gly Cys Pro Leu
    50                  55                  60

Ala Ala Thr Leu Ser Glu Gly Cys Pro Leu Ala Ala Thr Leu Ser Glu
65              70                  75                  80

His Ser Arg Val Leu Leu Glu Arg Gly Gly Leu Pro Ser Arg Asn
                85                  90                  95

Met Ser Asp Gln Gln His Phe Thr Asp Ala Leu Ala Asp Thr Ser Pro
            100                 105                 110

Ala Ser Pro Ala Gln Arg Phe Val Ser Glu Asp Gly Val Val Asn Ala
        115                 120                 125

Arg Ala Arg Val Leu Gly Gly Gly Ser Cys Leu Asn Arg Val Leu Gly
130                 135                 140

Gly Gly Ser Cys Leu Asn Ala Gly Phe Tyr Thr Arg Ala Ser Thr Asp
145                 150                 155                 160

Tyr Val Arg Ala Ala Gly Trp Asp Ala Arg Leu Val Asn Ser Ser Tyr
                165                 170                 175

Arg Trp Val Glu Arg Ala Leu Val Phe Arg Pro Ala Val Pro Pro Trp
            180                 185                 190

Gln Ala Ala Leu Arg Asp Ala Leu Leu Glu Ala Gly Val Thr Pro Asp
        195                 200                 205

Asn Gly Leu Glu Ala Gly Val Thr Pro Asp Asn Gly Phe Thr Phe Asp
    210                 215                 220

His Val Thr Gly Thr Lys Ile Gly Gly Thr Ile Phe Asp Ser Ser Gly
225                 230                 235                 240

Gln Arg His Thr Ala Ala Asp Phe Leu Arg His Ala Arg Pro Arg Gly
                245                 250                 255

Leu Thr Val Phe Leu Tyr Ala Thr Val Ser Arg Ile Leu Phe Arg Gln
            260                 265                 270

Gln Glu Gly Val Pro Tyr Pro Val Arg Gln Gln Glu Gly Val Pro Tyr
        275                 280                 285

Pro Val Ala Tyr Gly Val Val Phe Thr Asp Pro Leu Gly Val Gln His
    290                 295                 300

Arg Val Tyr Leu Arg Asp Gly Ala Lys Asn Glu Val Ile Leu Ser Ala
305                 310                 315                 320

Gly Thr Leu Gly Ser Pro Gln Leu Leu Met Leu Ser Gly Val Gly Pro
                325                 330                 335

Gln Ala His Leu Glu Ala His Gly Val Gln Val Leu Val Asp Glu Ala
            340                 345                 350

His Gly Val Gln Val Leu Val Asp Gln Pro Met Val Gly Gln Gly Val
        355                 360                 365

Ala Asp Asn Pro Met Asn Ser Val Phe Ile Pro Ser Pro Val Pro Val
    370                 375                 380

Thr Leu Ser Leu Val Gln Val Gly Ile Thr Arg Ser Gly Ser Phe
385                 390                 395                 400

Ile Glu Gly Val Ser Gly Ser Glu Phe Gly Ile Pro Val Ser Glu Gly
                405                 410                 415
```

Ala Arg Arg Leu Ile Pro Val Ser Glu Gly Ala Arg Arg Leu Ala Arg
            420                 425                 430

Ser Phe Gly Leu Phe Ser Pro Gln Thr Gly Gln Leu Gly Thr Leu Pro
        435                 440                 445

Pro Lys Gln Arg Thr Pro Glu Ala Leu Glu Arg Ala Ala Glu Ala Met
    450                 455                 460

Arg Arg Leu Asp Arg Arg Ala Phe Arg Gly Phe Ile Leu Glu Lys
465                 470                 475                 480

Ile Leu Gly Pro Val Ser Ser Gly His Val Ile Leu Gly Pro Val Ser
                    485                 490                 495

Ser Gly His Val Glu Leu Arg Ser Ala Asp Pro Arg Ala Asn Pro Ala
            500                 505                 510

Val Thr Phe Asn Tyr Phe Gln Glu Ser Glu Asp Leu Gln Arg Cys Val
        515                 520                 525

Arg Gly Ile Gln Thr Ile Glu Arg Val Ile Gln Ser Arg Ala Phe Ala
    530                 535                 540

Asn Phe Thr Tyr Ala Asn Ala Ser Thr Glu Ser Ile Phe Thr Asp Ser
545                 550                 555                 560

Ala Ser Thr Glu Ser Ile Phe Thr Asp Ser Ala Asn Phe Pro Val Asn
                    565                 570                 575

Leu Leu Pro Arg His Val Asn Asp Ser Arg Thr Pro Glu Gln Tyr Cys
            580                 585                 590

Arg Asp Thr Val Met Thr Ile Trp His Tyr His Gly Gly Cys Gln Val
        595                 600                 605

Gly Ala Val Val Asp Asp Tyr Arg Val Phe Gly Val Gln Arg Leu
    610                 615                 620

Arg Val Ile Asp Ser Ser Val Gln Arg Leu Arg Val Ile Asp Ser Ser
625                 630                 635                 640

Thr Phe Lys Tyr Ser Pro Gly Thr Asn Pro Gln Ala Thr Val Met Met
                    645                 650                 655

Leu Gly Arg Tyr Met Gly Val Lys Ile Gln Ala Glu Arg Trp Arg Lys
            660                 665                 670

<210> SEQ ID NO 19
<211> LENGTH: 1959
<212> TYPE: DNA
<213> ORGANISM: Setaria italica

<400> SEQUENCE: 19
tttgccggcg aaaatggcgc tggggcttgc gagctcggcg gcgctggttc tagccaccat      60
cctgggctcc ttgtgcctcg tcgcactctc agaggatgag caactcgaga acctgcggtt     120
cgtgcggcgc gcacaggacg cgcccctggt gtcgcactac aactacatca tcatcggcgg     180
cggcacggcg ggttgcccac tggcggcgac gctgtcggag cactcccgcg tgctgctcct     240
ggagcgcggt ggcctccccct accgcaacat gtccaaccag cagcacttca cggacgcgct     300
ggcggacacg tccccggcgt cgccggcgca gcggttcatc tccgaggacg cgtggtgaa      360 cgcccgggcg cgggtgctgg cggtggcag ctgcctcaac gccgggttct acacgcgcgc     420
cagcaacgac tacgtgcacg ccgccgggtg ggacgcgcgc ctcgtcaact cgtcctaccg     480
ctgggtggag cgcgcgctgg tgttccgccc cgacgttccg ccgtggcagg cggcgctccg     540

```
cgacgcgctg ctcgaggccg gcgtcacgcc cgacaacggg ttcaccttcg accacgtcac    600
ggggaccaag atcggggggca ccatcttcga cagcagcggg cagcggcaca ccgccgccga    660
cttcctccgc cacgcgcgcc ccggggggcct caccgtgctc ctctacgcca ccgtctcgag    720
gatcctcttc aggcagcagg aggggcgcc gtacccggtg gcgtacggcg tggtgttcag    780
cgacccgctg ggggtgcagc accgggtgta cctccaggac ggcggcaaga acgaggtgat    840
cctatcggcg gggacgctgg ggagcccgca gctgctgatg ctgagcggcg tcgggccgca    900
ggcgcacctg gaggcgcacg gcgtccaggt gctagtggac cagcccatgg tcgggcaggg    960
cgtggccgac aatcccatga actcggtgtt catcccgtcg cccgtgcccg tcgcgctctc   1020
gctcgtgcag gtcgtgggga tcacccgcac cggcagcttc atcgagggcg tcagcggctc   1080
cgagttcggc atcccagtct ccgagggcgt ccgccgcctc gctcgcaact tcggcctctt   1140
ctctcctcag accgggcagc tcggcacgct gccgccgaag cagaggacgc cggaggcgct   1200
gcagcgcgcg gcggaggcga tgcggcggct ggacaggcgg gcgttccggg gcggcttcat   1260
cctggagaag atcctgggggc ccgtgtcgtc gggccacatc gagctgcgct ccaccgaccc   1320
gcgcgcgaac ccggcggtga cgttcaacta cttccaggag aaggaggacc tggaccggtg   1380
cgtgcatggc atcgagacga tcgagcgggt catccagtcc cgggccttcg ccaatttcac   1440
ctacgccaac gcctccgtcg agtccatctt caccgactcc gccaacttcc ccgtcaacct   1500
gctgccgcgc cacgccaacg actcccggac gccggagcag tactgcaggg acaccgtcat   1560
gaccatctgg cactaccacg gcggctgcca ggtcggcgcc gtcgtcgacg atgactaccg   1620
ggtgttcggc gtgcagcggc tcagggtcat cgacagctcc accttcaagt actccccagg   1680
caccaacccg caggccaccg tcatgatgct cggaaggtat atgggtgtga aaatccaggc   1740
agagagatgg aggaaatgat caagaagagc aaatgatttc tgtatcgggg tacctgacta   1800
tctgctttag agtagttta ttttattttt ctctttactc ttctctagag atagttctag   1860
tttccggttg ttgattccaa atccttcaca ccctrgagat gcatagctca gcatttcgca   1920
agaacagtga aaaattatgc tgcattggca tgatggaaa                          1959
```

<210> SEQ ID NO 20
<211> LENGTH: 581
<212> TYPE: PRT
<213> ORGANISM: Setaria italica

<400> SEQUENCE: 20

Met Ala Leu Gly Leu Ala Ser Ser Ala Ala Leu Val Leu Ala Thr Ile
1               5                   10                  15

Leu Gly Ser Leu Cys Leu Val Ala Leu Ser Glu Asp Glu Gln Leu Glu
            20                  25                  30

Asn Leu Arg Phe Val Arg Arg Ala Gln Asp Ala Pro Leu Val Ser His
        35                  40                  45

Tyr Asn Tyr Ile Ile Ile Gly Gly Gly Thr Ala Gly Cys Pro Leu Ala
    50                  55                  60

Ala Thr Leu Ser Glu His Ser Arg Val Leu Leu Leu Glu Arg Gly Gly
65                  70                  75                  80

Leu Pro Tyr Arg Asn Met Ser Asn Gln Gln His Phe Thr Asp Ala Leu
                85                  90                  95

```
Ala Asp Thr Ser Pro Ala Ser Pro Ala Gln Arg Phe Ile Ser Glu Asp
            100                 105                 110

Gly Val Val Asn Ala Arg Ala Arg Val Leu Gly Gly Ser Cys Leu
        115                 120                 125

Asn Ala Gly Phe Tyr Thr Arg Ala Ser Asn Asp Tyr Val His Ala Ala
        130                 135                 140

Gly Trp Asp Ala Arg Leu Val Asn Ser Ser Tyr Arg Trp Val Glu Arg
145                 150                 155                 160

Ala Leu Val Phe Arg Pro Asp Val Pro Pro Trp Gln Ala Ala Leu Arg
                165                 170                 175

Asp Ala Leu Leu Glu Ala Gly Val Thr Pro Asp Asn Gly Phe Thr Phe
            180                 185                 190

Asp His Val Thr Gly Thr Lys Ile Gly Gly Thr Ile Phe Asp Ser Ser
        195                 200                 205

Gly Gln Arg His Thr Ala Ala Asp Phe Leu Arg His Ala Arg Pro Gly
    210                 215                 220

Gly Leu Thr Val Leu Leu Tyr Ala Thr Val Ser Arg Ile Leu Phe Arg
225                 230                 235                 240

Gln Gln Glu Gly Ala Pro Tyr Pro Val Ala Tyr Gly Val Phe Ser
                245                 250                 255

Asp Pro Leu Gly Val Gln His Arg Val Tyr Leu Gln Asp Gly Gly Lys
            260                 265                 270

Asn Glu Val Ile Leu Ser Ala Gly Thr Leu Gly Ser Pro Gln Leu Leu
        275                 280                 285

Met Leu Ser Gly Val Gly Pro Gln Ala His Leu Glu Ala His Gly Val
    290                 295                 300

Gln Val Leu Val Asp Gln Pro Met Val Gly Gln Gly Val Ala Asp Asn
305                 310                 315                 320

Pro Met Asn Ser Val Phe Ile Pro Ser Pro Val Pro Val Ala Leu Ser
                325                 330                 335

Leu Val Gln Val Val Gly Ile Thr Arg Thr Gly Ser Phe Ile Glu Gly
            340                 345                 350

Val Ser Gly Ser Glu Phe Gly Ile Pro Val Ser Glu Gly Val Arg Arg
        355                 360                 365

Leu Ala Arg Asn Phe Gly Leu Phe Ser Pro Gln Thr Gly Gln Leu Gly
    370                 375                 380

Thr Leu Pro Pro Lys Gln Arg Thr Pro Glu Ala Leu Gln Arg Ala Ala
385                 390                 395                 400

Glu Ala Met Arg Arg Leu Asp Arg Arg Ala Phe Arg Gly Phe Ile
                405                 410                 415

Leu Glu Lys Ile Leu Gly Pro Val Ser Ser Gly His Ile Glu Leu Arg
            420                 425                 430

Ser Thr Asp Pro Arg Ala Asn Pro Ala Val Thr Phe Asn Tyr Phe Gln
        435                 440                 445

Glu Lys Glu Asp Leu Asp Arg Cys Val His Gly Ile Glu Thr Ile Glu
    450                 455                 460

Arg Val Ile Gln Ser Arg Ala Phe Ala Asn Phe Thr Tyr Ala Asn Ala
465                 470                 475                 480

Ser Val Glu Ser Ile Phe Thr Asp Ser Ala Asn Phe Pro Val Asn Leu
                485                 490                 495

Leu Pro Arg His Ala Asn Asp Ser Arg Thr Pro Glu Gln Tyr Cys Arg
            500                 505                 510
```

Asp Thr Val Met Thr Ile Trp His Tyr His Gly Gly Cys Gln Val Gly
          515                 520                 525

Ala Val Val Asp Asp Tyr Arg Val Phe Gly Val Gln Arg Leu Arg
          530                 535                 540

Val Ile Asp Ser Ser Thr Phe Lys Tyr Ser Pro Gly Thr Asn Pro Gln
545                 550                 555                 560

Ala Thr Val Met Met Leu Gly Arg Tyr Met Gly Val Lys Ile Gln Ala
          565                 570                 575

Glu Arg Trp Arg Lys
          580

<210> SEQ ID NO 21
<211> LENGTH: 2000
<212> TYPE: DNA
<213> ORGANISM: Brachypodium distachyon

<400> SEQUENCE: 21

| | | | | | |
|---|---|---|---|---|---|
| atggcacttt | gccgcgcgat | ctcggcggcg | ctggtgctcg | ccgccgccgt | cttactcggc | 60 |
| tcgctctgcc | ccgtcgccct | ctcggaggac | ggtgcgtaca | tatattctgc | cttccgtgtt | 120 |
| tcttaagttg | tcacgactca | cgattaacgt | gtctcattcg | tgcgtgcaga | gcgactggag | 180 |
| aacctgcggt | tcgtgcagca | cgcatcggac | gcgccgctgg | tgtcgcactt | caactacatc | 240 |
| atcgtgggcg | ggggcacgtc | ggggtgcccg | ctggcggcga | cgctgtcgga | gcactcgcgg | 300 |
| gtgctcctcc | tggagcgggg | cgggctgccg | cacgccaaca | tgtcgagcca | ggagcacttc | 360 |
| acggacgcgc | tggcggacac | gtccccggcg | tccccggcgc | agcggttcgt | ttcggaagac | 420 |
| ggggtggtga | acgcccgcgc | cagggtgctt | ggcggaggga | gctgcctcaa | cgcgggcttc | 480 |
| tacacgcgcg | ccagcaacga | gtacgtcgcg | accgccgggt | gggaccccag | gctggtgaac | 540 |
| tcgtcctacc | gctgggtgga | gcgcgcgctc | gtgttccggc | caggcgtgcc | gccgtggcag | 600 |
| gcggctctgc | gggacgcgct | gctcgaggcc | ggcgtcacgc | cggataacgg | cttcacgttt | 660 |
| gatcatgtca | cggggaccaa | gatcggggc | accatcttcg | acggcaacgg | ccagcggcac | 720 |
| acggccgccg | acttcctacg | gcacgccagg | cccagggggcc | tcaccgtcgt | gctctacgcc | 780 |
| accgtgtcac | ggatcctctt | cagaagccaa | ggtactcttt | catgatccta | atttcatgtc | 840 |
| gaactacgca | gaaagaagta | agaacgactt | atttttgtgc | cgtgacacta | ctgtagaggg | 900 |
| cgttccgtac | ccggtggcgt | acggggtggt | gttcggggac | ccgctggggg | tgcagcaccg | 960 |
| ggtgtacctc | cgtgacgggg | ccaagaacga | ggtgatcctg | gcggccggga | cgctggggag | 1020 |
| cccgcagctg | ctgatgctga | gcggcgtggg | cccgcaggcg | cacctggagg | cccacggcat | 1080 |
| ccaggccctg | gtcgaccagc | ccatggtcgg | gcagggcgtc | gccgacaacc | ccatgaactc | 1140 |
| ggtgttcatc | ccgtcgccgg | tgcccgtggg | cctctccctg | gtgcaggtcg | tcggcatcac | 1200 |
| caagtccggc | agcttcatcg | agggcgtcag | cggctcggag | ttcggcatcc | cggtctccga | 1260 |
| cagcgcccgc | cgcctcgccg | ccagcttcgg | cctcttctct | cctcagaccg | ggcagctcgg | 1320 |
| cacgctgccg | cccaagcaga | ggacgcccga | ggcgctgcag | cgcgcggcgg | acgccatgcg | 1380 |
| gcggctcgac | cggcgcgcgt | tccggggcgg | cttcatcctg | gagaagatcc | tcgggccggt | 1440 |
| ctccacgggg | cacgtcgagc | tccggaccac | ggacccgagg | gccaacccgg | cggtgctgtt | 1500 |
| caactacttc | caggaggcgg | aggacctgga | gcggtgcgtg | cgggggatcc | agacgatcga | 1560 |

```
gcgtgtgatc gcgtcgcgtg ccttttcgaa cttcacctac tccaacgcct ccgtggagtc    1620
catcttcagc gactcggcga acttccccgt gaacctgctg ccgcggcacg ccaacgactc    1680
caggtcgccc gagcagtact gcagggagac cgtcatgacc atctggcact accacggcgg    1740
ctgccatgtc ggcgccgtcg tcgacgacga ttaccgggtg tttggggtaa gggggctcag    1800
ggtcatcgac agctccacct tcaggtactc ccccggcacc aacccgcagg ccaccgtcat    1860
gatgctcggc aggtaaactc gtcgaagtct gaaatgatta gttgtgttga tctgaatgac    1920
cttgagtaaa aacactagtg ttctgaatct gcacaggtat atgggagtga agattcaggc    1980
cgagagatgg aggaagtgat                                                2000

<210> SEQ ID NO 22
<211> LENGTH: 1752
<212> TYPE: DNA
<213> ORGANISM: Brachypodium distachyon

<400> SEQUENCE: 22
atggcacttt gccgcgcgat ctcggcggcg ctggtgctcg ccgccgccgt cttactcggc      60
tcgctctgcc ccgtcgccct ctcggaggac gagcgactgg agaacctgcg gttcgtgcag     120
cacgcatcgg acgcgccgct ggtgtcgcac ttcaactaca tcatcgtggg cgggggcacg     180
tcggggtgcc cgctggcggc gacgctgtcg gagcactcgc gggtgctcct cctggagcgg     240
ggcgggctgc cgcacgccaa catgtcgagc caggagcact tcacggacgc gctggcggac     300
acgtccccgg cgtccccggc gcagcggttc gtttcggaag acggggtggt gaacgcccgc     360
gccagggtgc ttggcggagg gagctgcctc aacgcgggct tctacacgcg cgccagcaac     420
gagtacgtgc gcaccgccgg gtgggacccc aggctggtga actcgtccta ccgctgggtg     480
gagcgcgcgc tcgtgttccg gccaggcgtg ccgccgtggc aggcggctct gcgggacgcg     540
ctgctcgagg ccggcgtcac gccggataac ggcttcacgt ttgatcatgt cacggggacc     600
aagatcgggg gcaccatctt cgacggcaac ggccagcggc acacggccgc cgacttccta     660
cggcacgcca ggcccagggg cctcaccgtc gtgctctacg ccaccgtgtc acggatcctc     720
ttcagaagcc aagagggcgt tccgtacccg gtggcgtacg gggtggtgtt cggggacccg     780
ctgggggtgc agcaccgggt gtacctccgt gacggggcca agaacgaggt gatcctggcg     840
gccgggacgc tggggagccc gcagctgctg atgctgagcg gcgtgggccc gcaggcgcac     900
ctggaggccc acggcatcca ggccctggtc gaccagccca tggtcgggca gggcgtcgcc     960
gacaaccccc tgaactcggt gttcatcccg tcgccggtgc ccgtgggcct ctccctggtg    1020
caggtcgtcg gcatcaccaa gtccggcagc ttcatcgagg gcgtcagcgg ctcggagttc    1080
ggcatcccgg tctccgacag cgccgccgc ctcgccgcca gcttcggcct cttctctcct    1140
cagaccgggc agctcggcac gctgccgccc aagcaggagga cgcccgaggc gctgcagcgc    1200
gcggcggacg ccatgcggcg gctcgaccgg cgcgcgttcc gggcggcttc atcctggag    1260 aagatcctcg gccggtctc cacggggcac gtcgagctcc ggaccacgga cccgagggcc    1320
aacccggcgg tgctgttcaa ctacttccag gaggcggagg acctggagcg gtgcgtgcgg    1380
gggatccaga cgatcgagcg tgtgatcgcg tcgcgtgcct tttcgaactt cacctactcc    1440
aacgcctccg tggagtccat cttcagcgac tcggcgaact tccccgtgaa cctgctgccg    1500
cggcacgcca acgactccag gtcgcccgag cagtactgca gggagaccgt catgaccatc    1560
```

```
tggcactacc acggcggctg ccatgtcggc gccgtcgtcg acgacgatta ccgggtgttt    1620
ggggtaaggg ggctcagggt catcgacagc tccaccttca ggtactcccc cggcaccaac    1680
ccgcaggcca ccgtcatgat gctcggcagg tatatgggag tgaagattca ggccgagaga    1740
tggaggaagt ga                                                        1752

<210> SEQ ID NO 23
<211> LENGTH: 583
<212> TYPE: PRT
<213> ORGANISM: Brachypodium distachyon

<400> SEQUENCE: 23

Met Ala Leu Cys Arg Ala Ile Ser Ala Ala Leu Val Leu Ala Ala
1               5                   10                  15

Val Leu Leu Gly Ser Leu Cys Pro Val Ala Leu Ser Glu Asp Glu Arg
            20                  25                  30

Leu Glu Asn Leu Arg Phe Val Gln His Ala Ser Asp Ala Pro Leu Val
        35                  40                  45

Ser His Phe Asn Tyr Ile Ile Val Gly Gly Gly Thr Ser Gly Cys Pro
    50                  55                  60

Leu Ala Ala Thr Leu Ser Glu His Ser Arg Val Leu Leu Leu Glu Arg
65                  70                  75                  80

Gly Gly Leu Pro His Ala Asn Met Ser Ser Gln Glu His Phe Thr Asp
                85                  90                  95

Ala Leu Ala Asp Thr Ser Pro Ala Ser Pro Ala Gln Arg Phe Val Ser
            100                 105                 110

Glu Asp Gly Val Val Asn Ala Arg Ala Arg Val Leu Gly Gly Gly Ser
        115                 120                 125

Cys Leu Asn Ala Gly Phe Tyr Thr Arg Ala Ser Asn Glu Tyr Val Arg
    130                 135                 140

Thr Ala Gly Trp Asp Pro Arg Leu Val Asn Ser Ser Tyr Arg Trp Val
145                 150                 155                 160

Glu Arg Ala Leu Val Phe Arg Pro Gly Val Pro Pro Trp Gln Ala Ala
                165                 170                 175

Leu Arg Asp Ala Leu Leu Glu Ala Gly Val Thr Pro Asp Asn Gly Phe
            180                 185                 190

Thr Phe Asp His Val Thr Gly Thr Lys Ile Gly Gly Thr Ile Phe Asp
        195                 200                 205

Gly Asn Gly Gln Arg His Thr Ala Ala Asp Phe Leu Arg His Ala Arg
    210                 215                 220

Pro Arg Gly Leu Thr Val Val Leu Tyr Ala Thr Val Ser Arg Ile Leu
225                 230                 235                 240

Phe Arg Ser Gln Glu Gly Val Pro Tyr Pro Val Ala Tyr Gly Val Val
                245                 250                 255

Phe Gly Asp Pro Leu Gly Val Gln His Arg Val Tyr Leu Arg Asp Gly
            260                 265                 270

Ala Lys Asn Glu Val Ile Leu Ala Ala Gly Thr Leu Gly Ser Pro Gln
        275                 280                 285

Leu Leu Met Leu Ser Gly Val Gly Pro Gln Ala His Leu Glu Ala His
    290                 295                 300

Gly Ile Gln Ala Leu Val Asp Gln Pro Met Val Gly Gln Gly Val Ala
305                 310                 315                 320

Asp Asn Pro Met Asn Ser Val Phe Ile Pro Ser Pro Val Pro Val Gly
                325                 330                 335
```

```
Leu Ser Leu Val Gln Val Val Gly Ile Thr Lys Ser Gly Ser Phe Ile
            340                 345                 350

Glu Gly Val Ser Gly Ser Glu Phe Gly Ile Pro Val Ser Asp Ser Ala
            355                 360                 365

Arg Arg Leu Ala Ala Ser Phe Gly Leu Phe Ser Pro Gln Thr Gly Gln
    370                 375                 380

Leu Gly Thr Leu Pro Pro Lys Gln Arg Thr Pro Glu Ala Leu Gln Arg
385                 390                 395                 400

Ala Ala Asp Ala Met Arg Arg Leu Asp Arg Arg Ala Phe Arg Gly Gly
                405                 410                 415

Phe Ile Leu Glu Lys Ile Leu Gly Pro Val Ser Thr Gly His Val Glu
            420                 425                 430

Leu Arg Thr Thr Asp Pro Arg Ala Asn Pro Ala Val Leu Phe Asn Tyr
                435                 440                 445

Phe Gln Glu Ala Glu Asp Leu Glu Arg Cys Val Arg Gly Ile Gln Thr
    450                 455                 460

Ile Glu Arg Val Ile Ala Ser Arg Ala Phe Ser Asn Phe Thr Tyr Ser
465                 470                 475                 480

Asn Ala Ser Val Glu Ser Ile Phe Ser Asp Ser Ala Asn Phe Pro Val
                485                 490                 495

Asn Leu Leu Pro Arg His Ala Asn Asp Ser Arg Ser Pro Glu Gln Tyr
            500                 505                 510

Cys Arg Glu Thr Val Met Thr Ile Trp His Tyr His Gly Gly Cys His
    515                 520                 525

Val Gly Ala Val Val Asp Asp Asp Tyr Arg Val Phe Gly Val Arg Gly
530                 535                 540

Leu Arg Val Ile Asp Ser Ser Thr Phe Arg Tyr Ser Pro Gly Thr Asn
545                 550                 555                 560

Pro Gln Ala Thr Val Met Met Leu Gly Arg Tyr Met Gly Val Lys Ile
                565                 570                 575

Gln Ala Glu Arg Trp Arg Lys
            580

<210> SEQ ID NO 24
<211> LENGTH: 678
<212> TYPE: DNA
<213> ORGANISM: Artificial Sequence
<220> FEATURE:
<223> OTHER INFORMATION: Synthetic

<400> SEQUENCE: 24
atggcctcct ccgagaacgt gatcaccgag ttcatgcgct tcaaggtgcg catggagggc      60
accgtgaacg ccacgagtt cgagatcgag ggcgagggcg agggccgccc ctacgagggc     120
cacaacaccg tgaagctgaa ggtgaccaag ggcggccccc tgcccttcgc ctgggacatc     180 ctgtccccc agttccagta cggctccaag gtgtacgtga agcaccccgc cgacatcccc     240
gactacaaga agctgtcctt ccccgagggc ttcaagtggg agcgcgtgat gaacttcgag     300
gacggcggcg tggccaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccgcg acggcgtgct gaagggcgag     480
acccacaagg ccctgaagct gaaggacggc ggccactacc tggtggagtt caagtccatc     540
tacatggcca agaagcccgt gcagctgccc ggctactact acgtggacgc caagctggac     600
```

| | |
|---|---|
| atcacctccc acaacgagga ctacaccatc gtggagcagt acgagcgcac cgagggccgc | 660 |
| caccacctgt tcctgtag | 678 |

<210> SEQ ID NO 25
<211> LENGTH: 812
<212> TYPE: DNA
<213> ORGANISM: Hordeum vulgare

<400> SEQUENCE: 25

| | |
|---|---|
| aaccgtctct tcgtgagaat aaccgtggcc taaaaataag ccgatgagga taaataaaat | 60 |
| gtggtggtac agtacttcaa gaggtttact catcaagagg atgcttttcc gatgagctct | 120 |
| agtagtacat cggacctcac atacctccat tgtggtgaaa tattttgtgc tcatttagtg | 180 |
| atgggtaaat tttgtttatg tcactctagg ttttgacatt tcagttttgc cactcttagg | 240 |
| ttttgacaaa taatttccat tccgcggcaa aagcaaaaca atttttatttt acttttacca | 300 |
| ctcttagctt tcacaatgta tcacaaatgc cactctagaa attctgtttta tgccacagaa | 360 |
| tgtgaaaaaa aacactcact tatttgaagc caaggtgttc atggcatgga aatgtgacat | 420 |
| aaagtaacgt tcgtgtataa gaaaaaattg tactcctcgt aacaagagac ggaaacatca | 480 |
| tgagacaatc gcgtttggaa ggctttgcat cacctttgga tgatgcgcat gaatggagtc | 540 |
| gtctgcttgc tagccttcgc ctaccgccca ctgagtccgg gcggcaacta ccatcggcga | 600 |
| acgacccagc tgacctctac cgaccggact tgaatgcgct accttcgtca gcgacgatgg | 660 |
| ccgcgtacgc tggcgacgtg cccccgcatg catggcggca catggcgagc tcagaccgtg | 720 |
| cgtggctggc tacaaatacg taccccgtga gtgccctagc tagaaactta cacctgcaac | 780 |
| tgcgagagcg agcgtgtgag tgtagccgag ta | 812 |

<210> SEQ ID NO 26
<211> LENGTH: 349
<212> TYPE: DNA
<213> ORGANISM: Solanum tuberosum

<400> SEQUENCE: 26

| | |
|---|---|
| ttcgaacgcg taggtaccac atggttaacc tagacttgtc catcttctgg attggccaac | 60 |
| ttaattaatg tatgaaataa aaggatgcac acatagtgac atgctaatca ctataatgtg | 120 |
| ggcatcaaag ttgtgtgtta tgtgtaatta ctagttatct gaataaaaga gaaagagatc | 180 |
| atccatattt cttatcctaa atgaatgtca cgtgtcttta taattctttg atgaaccaga | 240 |
| tgcatttcat taaccaaatc catatacata taaatattaa tcatatataa ttaatatcaa | 300 |
| ttgggttagc aaaacaaatc tagtctaggt gtgttttgcg aatgcggcc | 349 |

<210> SEQ ID NO 27
<211> LENGTH: 2023
<212> TYPE: DNA
<213> ORGANISM: Oryza sativa Indica

<400> SEQUENCE: 27

| | |
|---|---|
| atggcagcac ttggccgcgc gagctcgtcg gcgccggtgc ttgccgccgc cgccgccgcc | 60 |
| gccgtgctcc tctcgctctg cctcgccgcg ctctcggaag agcaaggtgc gtaaacgttg | 120 |
| cgttgtatct ttgcgttgat gcgtgttgcg tcgtcgtcgt gttcatggcg tgcgatggcg | 180 |
| ttgtgcagag caactggaga acctgcggtt cgtgcggcac gcgcaggacg cgccgctggt | 240 |
| gtcgagctac aactacatcg tcatcggcgg cggcacggcg gggtgcccgc tggcggcgac | 300 |
| gctgtcggag cactcgcgcg tgctgctgct ggagcgcggc ggcctgccgt acgccaacat | 360 |

```
gtcgagcgag cagcacttca cggacgcgct ggccgacacg tcgccggcgt cgccggcgca    420
gcggttcatc tcggaggacg gcgtggtgaa cgcccgggcg cgggtgctcg gcggcgggag    480
ctgcctcaac gccgggttct acacgcgggc gagcaacgag tacgtgcgcg ccgccgggtg    540
ggacgcgcgg ctggtgaact cgtcgtaccg gtgggtggag cgctcgctgg tgttccgccc    600
cgacgtgccg ccgtggcagg cggcgctccg cgacgcgctg ctcgaggtcg gcgtcacgcc    660
cgacaacggc ttcaccttcg accacgtcac cggcaccaag atcggcggca ccatcttcga    720
caactccggc cagcgccaca ccgccgccga cttcctccgc cacgcccgcc ccgcggcct     780
caccgtcctc ctctacgcca ccgtctcccg tatcctcttc aaaagccaag gtacacagct    840
acgatgaaaa tggaaaatgt gctgtgcgcc gaagaagctt gacctcacga cggcgagctt    900
tgccatggc gtgcagacgg ggtgccgtac ccggtggcgt acggggtggt gttctcggac     960
ccgctggggg tgcagcaccg ggtgtacctc cgcgacggcg acaagaacga ggtgatcgtg   1020
tcggcgggga cgctggggag cccgcagctg ctgatgctga cggcgtcgg gccgcaggcg    1080
cacctggagg cgcacggcat cgaggtgatc gtggaccaac ccatggtcgg gcagggcgtc   1140
gccgacaacc cgatgaactc ggtgttcatc ccgtcgccgg tgccggtgga gctctccctg   1200
gtgcaggtcg tcggcatcac ccgctccggc agcttcatcg aggggggtgag cgggtcggag   1260
ttcggcatgc cggtgtcgga cggcgcgctc cggtgggcgc gcagcttcgg gatgctgtcg   1320
ccgcagacgg ggcagctcgg cacgctgccg ccgaagcaga ggacgccgga ggcgctgcag   1380
cgggcggcgg aggcgatgat gcggctggac aggagggcgt tccggggagg cttcatcctg   1440
gagaagatcc tcgggccggt gtcctccggc cacgtcgagc tgcgaaccac cgacccgagg   1500
gcgaacccgt cggtgacgtt caactacttc cgcgaggcgg aggatctgga gcggtgcgtc   1560
catggcatcg agacgatcga gcgggtgatc cagtcgcggg ccttctccaa cttcacctac   1620
gccaacgcct ccgtcgagtc catcttcacc gattccgcca acttcccgt caacctgctg   1680
ccgcgccatg tcaacgactc gcgctcgccg gagcagtact gcatggacac cgtcatgacc   1740
atctggcact accacggcgg ctgccatgtc ggcgccgtcg tcgacgacga ttaccgggtg   1800
ttcggggtgc aggggctcag ggtgatcgac agctccacct tcaagtactc ccccggcacc   1860
aaccctcagg ccaccgtcat gatgctcggc aggtaactgg catcatttta gctcatgaaa   1920
gtgcattgcc atgagtaaca acacactaac agtatagttt tcaatatgga cactgggcag   1980
gtatatgggt gtgaagattc agtccgagag atggaagaaa tga                     2023
```

<210> SEQ ID NO 28
<211> LENGTH: 497
<212> TYPE: DNA
<213> ORGANISM: Oryza sativa Indica

<400> SEQUENCE: 28

```
tgaacaaaag ataatttcgt ttcaggagca aaaaaatgca tgtaattcaa ggaaaagaaa     60
atgttcaact gtctttagag tttagagtag atttttatttg cacccactta attttttactc   120
ttctctagac ataggttcag tatctgcttg ttgattatgt aaccttgaag aagcattgca    180
aaaacaaagc ggaaacttat gttaccaagg gcatgacgaa gaaataaatg gattagattt    240
cattgacact tagaaaatgg aaccagcaaa tcaaggctga aataattac actagaaact     300
tattttaatg gctttacatg tcgctacata cttaaatcaa tcaaagttgc taccaaagcc    360
atgttcccta aacagagggt tccgggctct caaacattct taatcttcta tacattgata   420
```

```
aaaagtatac ataaaaagaa aacctattaa gatggaaatg ttgaattctc ttaagaaagg      480
cataaaaaat gcagggt                                                    497

<210> SEQ ID NO 29
<211> LENGTH: 1488
<212> TYPE: DNA
<213> ORGANISM: Zea mays

<400> SEQUENCE: 29
atggcggcga caatggcagt gacgacgatg gtgacgagga gcaaggagag ctggtcgtca       60
ttgcaggtcc cggcggtggc attcccttgg aagccacgag gtggcaagac cggcggcctc      120
gagttccctc gccgggcgat gttcgccagc gtcggcctca acgtgtgccc gggcgtcccg      180
gcggggcgcg acccgcggga gcccgatccc aaggtcgtcc gggcggcctg cggcctggtc      240
caggcacaag tcctcttcca ggggtttaac tgggagtcgt gcaagcagca gggaggctgg      300
tacaacaggc tcaaggccca ggtcgacgac atcgccaagg ccggcgtcac gcacgtctgg      360
ctgcctccac cctcgcactc cgtctcgcca caaggctaca tgccaggccg cctatacgac      420
ctggacgcgt ccaagtacgg cacggcggcg gagctcaagt ccctgatagc ggcgttccac      480
ggcaggggcg tgcagtgcgt ggcggacatc gtcatcaacc accggtgcgc ggaaaagaag      540
gacgcgcgcg gcgtgtactg catcttcgag ggcgggactc ccgacgaccg cctggactgg      600 ggcccccggga tgatctgcag cgacgacacg cagtactcgg acgggacggg gcaccgcgac      660
acgggcgagg ggttcgcggc ggcgcccgac atcgaccacc tcaacccgcg cgtgcagcgg      720
gagctctccg cctggctcaa ctggctcagg tccgacgccg tggggttcga cggctggcgc      780
ctcgacttcg ccaagggcta ctcgccggcc gtcgccagaa tgtacgtgga gcacggggg      840 ccgccgagct tcgtcgtcgc ggagatatgg aactcgctga gctacagcgg ggacggcaag      900
ccggcgccca accaggacca gtgccggcag gagctgctgg actggacgcg ggccgtcggc      960
gggcccgcca tggcgttcga cttccccacc aaggcctgc tgcaggcggg cgtgcagggg     1020
gagctgtggc ggctgcgcga cagctccggc aacgcggccg gcctgatcgg gtgggcgccc     1080
gagaaggccg tcaccttcgt cgacaaccat gacaccgggt cgacgcagaa gctctggccg     1140
ttcccatccg acaaggtcat gcagggctac gcctacatcc tcacccatcc aggagtcccc     1200
tgcattttct acgaccacat gttcgactgg aacctgaagc aggagatatc cacgctgtct     1260
gccatcaggg cgcggaacgg catccgcgcc gggagcaagc tgcggatcct cgtggcggac     1320
gcggacgcgt acgtggccgt cgtcgacgag aaggtcatgg tgaagatcgg gacaaggtac     1380
ggcgtgagca gcgtggtccc gtcggatttc cacccggcgg cgcacggcaa ggactactgc     1440
gtctgggaga aagcgagcct ccgcgtcccg gcggggcgcc acctctag                  1488

<210> SEQ ID NO 30
<211> LENGTH: 2737
<212> TYPE: DNA
<213> ORGANISM: Zea mays

<400> SEQUENCE: 30
tgcaccggac actgtctggt ggcataccag acagtccggt gtgccagatc agggcaccct       60
tcggttcctt tgctcctttg cttttgaacc ctaactttga tcgtttattg gtttgtgttg      120
aacctttatg cacctgtgga atatataatc tagaacaaac tagttagtcc aatcatttgt      180
gttgggcatt caaccaccaa aattatttat aggaaaaggt taaacctat ttcccttca       240 atctcccct ttttggtgat tgatgccaac acaaaccaaa gaaatatat aagtgcagaa      300
```

```
ttgaactagt ttgcataagg taagtgcata ggttacttag aattaaatca atttatactt    360
ttacttgata tgcatggttg ctttcttttta ttttaacatt ttggaccaca tttgcaccac    420
ttgtttttgtt ttttgcaaat cttttttggaa attcttttttc aaagtctttt gcaaatagtc    480
aaaggtatat gaataagatt gtaagaagca ttttcaagat ttgaaatttc tccccctgtt    540
tcaaatgctt ttcctttgac taaacaaaac tcccctgaa taaaattctc ctcttagctt    600
tcaagagggt tttaaataga tatcaattgg aaatatattt agatgctaat tttgaaaata    660
taccaattga aaatcaacat accaatttga aattaaacat accaatttaa aaaatttcaa    720
aaagtggtgg tgcggtcctt ttgctttggg cttaatattt ctccccctttt ggcattaatc    780
gccaaaaacg gagactttgt gagccattta tactttctcc ccattggtaa atgaaatatg    840
agtgaaagat tataccaaat ttggacagtg atgcggagtg acggcgaagg ataaacgata    900
ccgttagagt ggagtggaag ccttgtcttc gccgaagact ccatttccct ttcaatctac    960
gacttagcat agaaatacac ttgaaaacac attagtcgta gccacgaaag agatatgatc   1020
aaaggtatac aaatgagcta tgtgtgtaat gtttcaatca aagtttcgag aatcaagaat   1080
atttagctca ttcctaagtt tgctaaaggt tttatcatct aatggtttgg taaagatatc   1140
gactaattgt tctttggtgc taacataagc aatctcgata tcaccccttt gttggtgatc   1200
cctcaaaaag tgataccgaa tgtctatgtg cttagtgcgg ctgtgttcaa cgggattatc   1260
cgccatgcag atagcactct cattgtcaca taggagaggg actttgctca atttgtagcc   1320
atagtcccta aggttttgcc tcatccaaag taattgcaca caacaatgtc ctgcggcaat   1380
atacttggct tcggcggtag aaagagctat tgagttttgt ttctttgaag tccaagacac   1440
cagggatctc cctagaaact gacaagtccc tgatgtgctc ttcctatcaa ttttacaccc   1500
tgcccaatcg gcatctgaat atcctattaa atcaaaggtg gatcccttgg ggtaccaaag   1560
accaaattta ggagtgtaaa ctaaatatct catgattctt ttcacggccc taaggtgaac   1620
ttccttagga tcggcttgga atcttgcaca catgcatata gaaagcatac tatctggtcg   1680
agatgcacat aaatagagta aagatcctat catcgaccgg tataccttttt ggtctacgga   1740
tttacctccc gtgtcgaggt cgagatgccc attagttccc atgggtgtcc tgatgggctt   1800
ggcatccttc attccaaact tgttgagtat gtcttgaatg tactttgttt ggctgatgaa   1860
ggtgccatct tggagttgct tgacttgaaa tcctagaaaa tatttcaact tccccatcat   1920
agacatctcg aatttcggaa tcatgatcct actaaactct tcacaagtag atttgttagt   1980
agacccaaat ataatatcat caacataaat ttggcataca aacaaaactt ttgaaatggt   2040
tttagtaaag agagtaggat cggctttact gactctgaag ccattagtga taagaaaatc   2100
tcttaggcat tcataccatg ctgttggggc ttgcttgagc ccataaagcg cctttgagag   2160
tttataaaca tggttagggt actcactatc ttcaaagccg agaggttgct caacatagac   2220
ctattcaccc catttgatca cttttttggt ccttcaggat ctaatagtta tgtataattt   2280
agagtctctt gttttaatggc cagatatttc taattaatct aagaatttat gatatttttt   2340
aattttttat catgtctgat gagaattaac ataaaggctc aattgggtcc tgaattaata   2400
atagagtgaa aattaatcca gaggctctat tagaaccttc aattagtaat accaagatat   2460
atataagata gtagagtata gtttaaatgt tggcattgtt cattctttct tttgttattt   2520
aatttatgct ttccacggtg gttagtggtt acttctgaag ggtccaaata atgcatgaag   2580
agtttgagga caagaagtct gccctaaaaa tagcgatgca aaggcatggt gtccaagcca   2640
```

```
tacatatagc gcactaattt tatcagcaga acaatggtat ttataggtcc tagtgcccag    2700
gcaacaagag acacgaataa agcatcgatc acgacac                            2737

<210> SEQ ID NO 31
<211> LENGTH: 225
<212> TYPE: DNA
<213> ORGANISM: Zea mays

<400> SEQUENCE: 31
atggcggcga caatggcagt gacgacgatg gtgacgagga gcaaggagag ctggtcgtca      60
ttgcaggtcc cggcggtggc attcccttgg aagccacgag gtggcaagac cggcggcctc     120
gagttccctc gccgggcgat gttcgccagc gtcggcctca acgtgtgccc gggcgtcccg     180
gcggggcgcg acccgcggga gcccgatccc aaggtcgtcc gggcg                     225

<210> SEQ ID NO 32
<211> LENGTH: 348
<212> TYPE: DNA
<213> ORGANISM: Zea mays

<400> SEQUENCE: 32
gatctgacaa agcagcatta gtccgttgat cggtggaaga ccactcgtca gtgttgagtt      60
gaatgtttga tcaataaaat acggcaatgc tgtaagggtt gttttttatg ccattgataa     120
tacactgtac tgttcagttg ttgaactcta tttcttagcc atgccaagtg cttttcttat     180
tttgaataac attacagcaa aaagttgaaa gacaaaaaaa aaaaccccg aacagagtgc      240 tttgggtccc aagctacttt agactgtgtt cggcgttccc cctaaatttc tccccctata     300
tctcactcac ttgtcacatc agcgttctct ttcccctata tctccacg                  348

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
gcctcaccgt cctcctctac                                                  20

<210> SEQ ID NO 34
<211> LENGTH: 18
<212> TYPE: DNA
<213> ORGANISM: Artificial Sequence
<220> FEATURE:
<223> OTHER INFORMATION: synthetic

<400> SEQUENCE: 34
cgggtccgag aacaccac                                                    18

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
gctatgtacg tcgccatcca                                                  20

<210> SEQ ID NO 36
<211> LENGTH: 21
```

```
<212> TYPE: DNA
<213> ORGANISM: Artificial Sequence
<220> FEATURE:
<223> OTHER INFORMATION: synthetic

<400> SEQUENCE: 36
ggacagtgtg gctgacacca t                                            21

<210> SEQ ID NO 37
<211> LENGTH: 25
<212> TYPE: DNA
<213> ORGANISM: Artificial Sequence
<220> FEATURE:
<223> OTHER INFORMATION: synthetic

<400> SEQUENCE: 37
ggatccggat ttcgaggatc aagct                                        25

<210> SEQ ID NO 38
<211> LENGTH: 25
<212> TYPE: DNA
<213> ORGANISM: Artificial Sequence
<220> FEATURE:
<223> OTHER INFORMATION: synthetic

<400> SEQUENCE: 38
gtcgactttc gccgggcaaa ttcgc                                        25

<210> SEQ ID NO 39
<211> LENGTH: 27
<212> TYPE: DNA
<213> ORGANISM: Artificial Sequence
<220> FEATURE:
<223> OTHER INFORMATION: synthetic

<400> SEQUENCE: 39
gtttaaacgg atttcgagga tcaagct                                      27

<210> SEQ ID NO 40
<211> LENGTH: 25
<212> TYPE: DNA
<213> ORGANISM: Artificial Sequence
<220> FEATURE:
<223> OTHER INFORMATION: synthetic

<400> SEQUENCE: 40
ggatccaccc tgcatttttt atgcc                                        25

<210> SEQ ID NO 41
<211> LENGTH: 16
<212> TYPE: DNA
<213> ORGANISM: Artificial Sequence
<220> FEATURE:
<223> OTHER INFORMATION: synthetic

<400> SEQUENCE: 41
gcgtcgccga caaccc                                                  16

<210> SEQ ID NO 42
<211> LENGTH: 17
<212> TYPE: DNA
<213> ORGANISM: Artificial Sequence
<220> FEATURE:
<223> OTHER INFORMATION: synthetic

<400> SEQUENCE: 42
```

```
tggagaaggc ccgcgac                                             17
```

<210> SEQ ID NO 43
<211> LENGTH: 1767
<212> TYPE: DNA
<213> ORGANISM: Artificial Sequence
<220> FEATURE:
<223> OTHER INFORMATION: Synthetic: HHZ_ OsNP1 CDs secquence

<400> SEQUENCE: 43

```
atggcagcac ttggccgcgc gagctcgtcg gcgccggtgc ttgccgccgc cgccgccgcc    60
gccgtgctcc tctcgctctg cctcgccgcg ctctcggaag agcaagagca actggagaac   120
ctgcggttcg tgcggcacgc gcaggacgcg ccgctggtgt cgagctacaa ctacatcgtc   180
atcggcggcg gcacggcggg gtgcccgctg gcggcgacgc tgtcggagca ctcgcgcgtg   240
ctgctgctgg agcgcggcgg cctgccgtac gccaacatgt cgagcgagca gcacttcacg   300
gacgcgctgg ccgacacgtc gccggcgtcg ccggcgcagc ggttcatctc ggaggacggc   360
gtggtgaacg cccgggcgcg ggtgctcggc ggcgggagct gcctcaacgc cgggttctac   420
acgcgggcga gcaacgagta cgtgcgcgcc gccgggtggg acgcgcggct ggtgaactcg   480
tcgtaccggt gggtggagcg ctcgctggtg ttccgccccg acgtgccgcc gtggcaggcg   540
gcgctccgcg acgcgctgct cgaggtcggc gtcacgcccg acaacggctt caccttcgac   600
cacgtcaccg gcaccaagat cggcggcacc atcttcgaca actccggcca gcgccacacc   660
gccgccgact cctccgcca cgcccgcccc cgcggcctca ccgtcctcct ctacgccacc   720
gtctcccgta tcctcttcaa aagccaagac ggggtgccgt acccggtggc gtacggggtg   780
gtgttctcgg acccgctggg ggtgcagcac cgggtgtacc tccgcgacgg cgacaagaac   840
gaggtgatcg tgtcggcggg gacgctgggg agcccgcagc tgctgatgct gagcggcgtc   900
gggccgcagg cgcacctgga ggcgcacggc atcgaggtga tcgtggacca acccatggtc   960
gggcagggcg tcgccgacaa cccgatgaac tcggtgttca tcccgtcgcc ggtgccggtg  1020
gagctctccc tggtgcaggt cgtcggcatc acccgctccg gcagcttcat cgaggggggtg  1080
agcgggtcga agttcggcat gccggtgtcg gacggcgcgc tccggtgggc gcgcagcttc  1140
gggatgctgt cgccgcagac ggggcagctc ggcacgctgc cgccgaagca gaggacgccg  1200
gaggcgctgc agcgggcggc ggaggcgatg atgcggctgg acaggagggc gttccgggga  1260
ggcttcatcc tggagaagat cctcgggccg gtgtcctccg gccacgtcga gctgcgaacc  1320
accgacccga gggcgaaccc gtcggtgacg ttcaactact ccgcgaggc ggaggatctg   1380
gagcggtgcg tccatggcat cgagacgatc gagcgggtga tccagtcgcg ggccttctcc  1440
aacttcacct acgccaacgc ctccgtcgag tccatcttca ccgattccgc caacttcccc  1500
gtcaacctgc tgccgcgcca tgtcaacgac tcgcgctcgc cggagcagta ctgcatggac  1560
accgtcatga ccatctggca ctaccacggc ggctgccatg tcggcgccgt cgtcgacgac  1620
gattaccggg tgttcggggt gcagggggctc agggtgatcg acagctccac cttcaagtac  1680
tcccccggca ccaaccctca ggccaccgtc atgatgctcg gcaggtatat gggtgtgaag  1740
attcagtccg agagatggaa gaaatga                                      1767
```

FERTILITY GENE AND USE THEREOF

FIELD

The present disclosure relates to the field of biotechnology, in particular to plant hybrid methods, including the preparation of a sterile line and the production of hybrid seeds, more particularly to a fertility gene FL2, and its mutant and use in hybrid breeding.

BACKGROUND

Hybrid breeding is an effective way of improving the production of crops. Compared to conventional plants, hybrids often exhibit heterosis, and usually have a significantly increased yield, better resistance, and wider adaptability. In addition, hybrid breeding is less time-consuming and has a shorter breeding cycle than conventional breeding. Therefore, hybrid breeding has become a major approach in the breeding of many crops.

An efficient male sterile line is the key factor in hybrid breeding. The male sterile line, which cannot produce effective male gametes is used as a maternal line to be pollinated by a paternal line. The following factors should be considered during the selection and generation of male sterile lines:

1. Hybrid vigor with other lines: the male sterile line can be crossed with other male-fertile lines to produce hybrids with a better combination of traits;

2. The reproduction of the male sterile line: the sterile line can restore fertility to self-maintain under certain conditions;

3. The efficiency of the reproduction and hybrid seed production using the male sterile line: a good sterile line should be easy to cross and lead to efficient hybrid seed production.

Male sterility can be either cytoplasmic or nuclear. Current hybrid rice breeding utilizes the combination of both types of male sterility. Cytoplasmic male sterility (CMS) is caused by mutations in extranuclear genes and shows maternal inheritance. Manifestation of male sterility in CMS lines may be controlled through the interaction between cytoplasmic and nuclear factors. The widely used three-line method in hybrid rice breeding involves a male sterile line, a restorer line and a maintainer line. The three-line method requires specific restorer lines, which are generated through a complex process and greatly limits the utilization of heterosis between different varieties. By contrast, two-line method utilizes a male sterile line, in which the sterility is controlled by a nuclear gene and the fertility can be restored in under specific growing conditions, and therefore combines the restorer line and the maintainer line into one line. Compared with three-line method, two-line method has greatly simplified the hybrid seed production process by eliminating the demand of maintainer lines and significantly expanded the usage of male sterility in hybrid breeding. However, there also are constraints in the utilization of two-line hybrid breeding method. The male sterile line need to switch fertility between ON and OFF under different conditions. It has to remain male sterile for hybrid seed production but be fertile to self-propagate. The widely used male sterile lines in two-line method are mostly photo-thermo-sensitive sterile (PTGMS), and their fertility is influenced by temperature and light. Therefore, the instability of the environment may result in the instability of the fertility of sterile lines, leading to either self-breeding and reduced purity of the hybrid seed, thereby increasing the risk of seed production. Furthermore, the methodology used for selection and generation of sterile lines for two-line method is very limited. For example, there are hardly any male sterile lines suitable for two-line method in *Oryza japonica* rice, restricting wide use of rice variety resources.

In order to bypass the problems existing in the current methods of hybrid rice breeding, such as the stability of the sterile line, the limitation of hybrid variety resources, the complexity in seed production, the high cost of seed production, etc., a new hybrid breeding technique is described. The present technique can fully utilize male sterility controlled by recessive nuclear genes to construct stable sterile lines that are not affected by environmental changes, in order to eliminate the potential risk in seed production. Meanwhile, the recessive nuclear sterility gene is suitable for vast majority of crop varieties to improve heterosis utilization. Embodiments of the present disclosure provide a gene regulating plant fertility, the mutation of which results in male sterility and the sterility is stable and not influenced by environment and may be reversed through introduction of the wild-type gene into plants. The gene and the sterile line generated by the gene mutation provide necessary components for a new hybrid breeding system.

SUMMARY

The present disclosure provides a DNA sequence, which has a function of regulating plant fertility, and the DNA sequence is at least one selected from a group consisting of:
 a) nucleotide sequences of SEQ ID NO: 1, 5 or 27,
 b) nucleotide sequences of SEQ ID NO: 10 or 11,
 c) nucleotide sequences of SEQ ID NO: 13 or 14,
 d) nucleotide sequences of SEQ ID NO: 16 or 17,
 e) nucleotide sequences of SEQ ID NO: 19,
 f) nucleotide sequences of SEQ ID NO: 21 or 22,
 g) nucleotide sequences hybridizable with any one of the nucleotide sequences of (a)-(f) under a stringent condition, or
 h) nucleotide sequences complementary to any one of the nucleotide sequences of (a)-(g).

The above-mentioned DNA sequence may encode an amino acid sequence of SEQ ID NO: 2, 6, 8, 12, 15, 18, 20 or 23.

The present disclosure also provides an expression cassette comprising the above-mentioned DNA sequence.

The present disclosure also provides an expression vector comprising the above-mentioned expression cassette.

The present disclosure also provides an engineered bacterium comprising the above-mentioned expression vector.

The present disclosure also provides use of a gene in regulation of plant fertility, and the gene regulating plant fertility comprises a nucleotide sequence selected from a group consisting of:
 a) nucleotide sequences of SEQ ID NO: 1, 5 or 27,
 b) nucleotide sequences of SEQ ID NO: 10 or 11,
 c) nucleotide sequences of SEQ ID NO: 13 or 14,
 d) nucleotide sequences of SEQ ID NO: 16 or 17,
 e) nucleotide sequences of SEQ ID NO: 19,
 f) nucleotide sequences of SEQ ID NO: 21 or 22,
 g) nucleotide sequences hybridizable with any one of the nucleotide sequences of (a)-(f) under a stringent condition, or
 h) nucleotide sequences complementary to any one of the nucleotide sequences of (a)-(g).

Embodiments of the present disclosure also include a method to obtain a male sterile material through mutating the gene regulating plant fertility of SEQ ID NO: 1, 5, 10, 11, 13, 14, 16, 17, 19, 21, 22 or 27.

The term "mutation" used herein comprises substitution, deletion or addition of one or more nucleotide in the DNA sequence of the gene regulating plant fertility.

The present disclosure also provides a method for fertility recovery in the male sterile material by introducing the above-mentioned DNA sequence, with the male sterile material being obtained by a gene mutation of SEQ ID NO: 1, 5, 10, 11, 13, 14, 16, 17, 19, 21, 22 or 27 correspondingly.

The present disclosure also provides use of a mutant material obtained by a mutation of a nucleotide sequence comprising SEQ ID NO: 1, 5, 10, 11, 13, 14, 16, 17, 19, 21, 22 or 27.

The above-mentioned "mutation" may be point mutation, DNA deletion, insertion mutation or gene silence by means of RNAi or site-directed mutagenesis.

Embodiments of the present disclosure provide a method to utilize the above-mentioned material and DNA sequences in breeding, particularly comprising crossing a male sterile plant as a female parent to be crossed with a restorer line to produce a hybrid seed.

The present disclosure also provides a promoter having a characteristic of anther specific expression, comprising a nucleotide sequence of SEQ ID NO: 3 or 9. The present disclosure also includes an expression cassette containing the described promoter, an expression vector containing the described expression cassette, and/or an engineered bacterium that containing the described expression vector.

The present disclosure also provides a method of expressing a target polynucleotide sequence in a plant, comprising:
  introducing a DNA construct into the plant, and
  the DNA construct comprises:
  a promoter comprising a nucleotide sequence of SEQ ID NO: 3 or 9; and
  the target nucleotide sequence operably linked to the promoter.

The expression of "target nucleotide sequence" used herein may be a structural gene, a regulator gene, an antisense sequence of the structural gene, an antisense sequence of the regulator gene or microRNA interfering with the expression of an endogenous gene, which is specifically expressed late in pollen development and regulates pollen fertility and pollen germination.

The present disclosure also provides use of the above-described DNA sequence or the promoter in any one of (a) to (d):
  (a) breeding of plant varieties or strains;
  (b) breeding of plant varieties or strains for enhanced fertility;
  (c) breeding of plant varieties or strains for reduced fertility;
  (d) breeding of male sterile plant varieties or strains.

The present disclosure also provides a method of maintaining a male sterile plant at a homozygous recessive state, comprising:
  (a) providing the first plant being male sterile and being homozygous for the recessive allele of FL2 gene;
  (b) generating the second plant being homozygous for the recessive allele of FL2 gene and being hemizygous for a construct by introducing to the first plant the construct, and the construct comprising:
  i) the first nucleotide sequence having FL2 nucleotide sequence to recover male fertility of the first plant when expressed in the first plant;
  ii) the second nucleotide sequence to inhibit the formation or function of a gamete of male fertility when expressed in the second plant, with the second nucleotide sequence being a pollen inactivation gene ZM-PA; and
  (c) fertilizing the first plant with the male gamete of the second plant to maintain an offspring of the first plant in a homozygous state.

BRIEF DESCRIPTION OF THE DRAWINGS

FIG. 6A-C—Alignment of OsFL2 cDNA related sequences, including Huanghuazhan wild-type OsFL2, cDNA of Huanghuazhan mutant OsFL2 and cDNA of Nipponbare wild-type OsFL2. HHZ represents the sequence of Huanghuazhan wild-type OsFL2 (SEQ ID NO:1), Mutant represents the sequence of Huanghuazhan mutant OsFL2 (SEQ ID NO:7), Nip represents the sequence of Nipponbare wild-type OsFL2 (SEQ ID NO:5). The bottom sequence (SEQ ID NO: 43) is a consensus sequence based on the three sequences above it.

FIG. 7—Alignment of OsFL2 related protein sequences, including Huanghuazhan wild-type OsFL2, Huanghuazhan mutant OsFL2 and Nipponbare wild-type OsFL2. HHZ represents the protein sequence of Huanghuazhan wild-type OsFL2 (SEQ ID NO: 2), Mutant represents the protein sequence of Huanghuazhan mutant OsFL2 (SEQ ID NO: 8), Nip represents the protein sequence of Nipponbare wild-type OsFL2 (SEQ ID NO: 6).

FIG. 14—Alignment of protein sequences encoded by rice OsFL2 gene (SEQ ID NO: 8) and its homologous genes of barley (SEQ ID NO: 12), sorghum (SEQ ID NO: 15), millet (SEQ ID NO: 20), *brachypodium distachyon* (SEQ ID NO: 23) and maize (SEQ ID NO: 18), respectively.

DETAILED DESCRIPTION

Figure 1:
FIG. 1—The floret morphology of Huanghuazhan with mutant OsFL2 or wild-type OsFL2.

All references mentioned herein are incorporated herein by reference.

Unless specifically defined otherwise, all technical and scientific terms used herein have the same meaning as commonly understood by one of ordinary skill in the art to which this invention belongs. Unless defined otherwise, the technologies used or cited in the present disclosure are standard technologies well known by one of ordinary skill in the art to which this invention belongs.

The materials, methods and embodiments described herein are explanatory, illustrative only, which shall not be construed to limit the scope of the present disclosure.

The present disclosure provides a fertility gene, a nucleotide sequence, a protein sequence thereof, and use of the fertility gene in regulation of plant male fertility. By way of non-limiting examples, any method described below may be used together with the corresponding nucleotide sequence of the present disclosure, for example, any method selected from the following may be used: introducing the mutant sequence of the fertility gene into a plant to obtain plant male sterility, mutating a plant endogenous sequence, introducing an antisense sequence of the fertility gene into the plant, utilizing a form of hairpin, ligating the corresponding nucleotide sequence with other nucleotide sequence to regulate a plant phenotype, or any method for influencing the plant male fertility known to persons skilled in the art.

The fertility gene FL2 provided herein is a gene involved in pollen development. The fertility gene FL2 locates in chromosome 10 of the rice plant. The fertility gene FL2 has a nucleotide sequence of SEQ ID NO:1, 4 or 27 in *Oryza Sativa* ssp. *indica*, and the corresponding amino acid sequence is SEQ ID NO:2. The fertility gene FL2 has a nucleotide sequence of SEQ ID NO:5 in *Oryza japonica*, and the corresponding amino acid sequence is SEQ ID NO:6. The fertility gene FL2 has a nucleotide sequence of SEQ ID NO:10 or 11 in barley, and the corresponding amino acid sequence is SEQ ID NO:12. The fertility gene FL2 has a nucleotide sequence of SEQ ID NO:13 or 14 in sorghum, and the corresponding amino acid sequence is SEQ ID NO:15. The fertility gene ZmFL2 has a nucleotide sequence of SEQ ID NO:13 or 14 in maize, and the corresponding amino acid sequence is SEQ ID SEQ ID NO:15. The fertility gene ZmFL2 has a nucleotide sequence of SEQ ID NO:16 or 17 in maize, and the corresponding amino acid sequence is SEQ ID SEQ ID NO:18. The fertility gene FL2 has a nucleotide sequence of SEQ ID NO:19 in millet, and the corresponding amino acid sequence is SEQ ID NO:20. The fertility gene FL2 has a nucleotide sequence of SEQ ID NO:21 or 22 in *Brachypodium distachyon*, and the corresponding amino acid sequence is SEQ ID NO:23.

The present disclosure also provides one of the following sequences: a) a DNA sequence with at least 90% (preferably at least 95%) sequence similarity of FL2 gene described above and a homologous function, b) an DNA sequence hybridizable with the DNA sequence of a) under a stringent condition; c) an DNA sequence complementary to any one of the DNA sequence described above in a)-b).

The fertility gene described above may be isolated from various plants. As by one skilled in the art, the fertility gene of the present disclosure comprises functionally equivalent sequences which are highly homologous to FL2 gene and regulate fertility likewise, highly homologous and functionally equivalent sequences include DNA sequences hybridizable with FL2 gene of the present disclosure under a stringent condition. "A stringent condition" used the present disclosure is commonly understood by one of ordinary skill in the art and may comprise: hybridizing in a hybridization solution consisting of 400 mM NaCl, 40 mM PIPES ( ) and 1 mM EDTA at 60° C. for 12-16 h, then washed with the wash solution consisting of 0.1% and 0.1×SSC at 65° C. for 15-60 min.

The functionally equivalent sequence also includes a DNA sequence regulating plant fertility with at least 90%, at least 95%, at least 96%, at least 97%, at least 98%, or at least 99% sequence similarity of FL2 gene in the present disclosure, which may be isolated from any plant. A percentage of sequence similarity may be obtained by bioinformatic algorithms commonly known by a person skilled in the art, including Myers and Miller algorithm (Bioinformatics, 4(1): 11-17, 1988), Needleman-Wunsch global alignment method (J. Mol. Biol., 48(3): 443-53, 1970), Smith-Waterman local alignment method (J. Mol. Biol., 147: 195-197, 1981), Pearson and Lipman similarity search method (PNAS, 85(8): 2444-2448, 1988), Karlin and Altschul algorithm (Altschul et al, J. Mol. Biol., 215(3): 403-410, 1990; PNAS, 90: 5873-5877, 1993), which are well known to those skilled in the art. 100551 The nucleotide sequence of the fertility gene of present disclosure may be isolated from any plant, including but not limited to, *Brassica*, maize, wheat, sorghum, *Crambe* linn, *Sinapis alba*, castor bean, sesame, cottonseed, linseed, soybean, *Arabidopsis, Phaseolus*, peanut, alfalfa, oat, rapeseed, barley, oat, rye, millet, dhurra, riticale, einkorn, Spelt, emmer, flax, Gramma grass, *Tripsacum, euchlaena Mexicana, Festuca ovina*, Perennial wheatgrass, sugarcane, *Vaccinium oxycoccos, papaya*, banana, Safflower, oil palm, muskmelon, apple, cucumber, dendrobe, *gladiolus, chrysanthemum*, Liliaceae, cotton, *eucalyptus*, sunflower, *Brassica rapa*, beet, coffee, ornamental plant, conifer and so on. Preferably, the plant includes maize, soybean, Safflower, mustard, wheat, barley, rye, rice, cotton, and sorghum.

Also provided in the present disclosure is a method of influencing plant fertility by influencing a nucleotide sequence of FL2 or by regulating the transcription and expression of FL2 gene. The expression of "influencing plant fertility" means changing the fertility of a plant, for example obtaining male sterility, by regulating the expression of FL2 gene. Particularly, depending on the specific application, the FL2 gene expression in plant may be influenced by many methods to regulate the plant male fertility. More particularly, the expression of FL2 gene may be manipulated by all kinds of tools available to one of ordinary skill in the art. For example, mutation, mutagenesis, introduction of an antisense gene, co-suppression, introduction of hairpin, and alike can be used to interfere the normal expression of FL2 gene, and to obtain the male sterile plant. In other embodiments, the present disclosure also includes the way of recovering the male fertility to the plant with disturbed FL2 expression by introducing the wild-type nucleotide sequence of FL2 to the plant.

Further provided in the present disclosure are the mutant nucleotide sequence of FL2 gene that leads to male sterility and a male sterile mutant material. More particularly, the male sterile mutant material is obtained by a process of mutating endogenous FL2 gene of rice, or mutating of the nucleotide sequence of a gene highly homologous to FL2 gene, leading to loss of male fertility. The term of "mutating" includes, but is not limited to the following methods, for example gene mutation induced by physical or chemical method. The chemical method includes mutagenesis induced by mutagen such as EMS etc. The mutation may be point mutation, nucleotide deletion, or nucleotide insertion, or gene silencing by means of RNAi, site-directed mutagenesis and so on.

Particularly, also provided in the present disclosure is a male sterile mutant of rice, containing the mutant FL2 gene. The nucleotide sequence of the mutant male sterility gene is shown as SEQ ID NO:7 and the amino acid sequence thereof is SEQ ID NO:8. Compared with wild-type, in the male-sterile mutant, G is mutated into A at the 1688.sup.th nucleotide of the coding sequence of the mutant male sterility gene (FIG. 6A-C), which leads to a glycine (G) to Aspartic Acid (D) change at the 563.sup.rd amino acid in the corresponding encoded protein sequence. As known by the person skilled in the art, the nucleotide sequence of SEQ ID NO:7 can be constructed into a plant expression vector to transform a plant and obtain a new transgenic male sterile mutant material.

Further provided in the present disclosure is the promoter of FL2 gene with a function of specific expression in anther, and the corresponding nucleotide sequence of the promoter is a nucleotide sequence 700 bp to 2500 bp upstream of ATG of the FL2 gene. More particularly, in rice, the nucleotide sequence of the promoter of OsFL gene is SEQ ID NO:3 or SEQ ID NO:9. The nucleotide sequence shown as SEQ ID NO:3 and SEQ ID NO:9 were ligated with the reporter gene GUS and transformed into plants respectively. The resulting transgenic plants were analyzed. Specifically, the roots, stems, leaves, and flowers were stained for GUS activity. It was found that the GUS gene driven by the promoter of OsFL2 gene is mostly expressed in rice anthers, particularly expressed highly specifically at the P7 stage of anther development. Therefore, the promoter of SEQ ID NO:3 or SEQ ID NO:9 provided in the present disclosure is be an anther-specific promoter.

The anther-specific promoter provided in the present disclosure includes the nucleotide sequence of SEQ ID NO:3 or SEQ ID NO:9, a nucleotide sequence with at least 90% sequence similarity to the nucleotide sequence of SEQ ID NO:3 or SEQ ID NO:9, or a sequential nucleotide fragment of at least 100 bp from the nucleotide sequence of SEQ ID NO:3 or SEQ ID NO:9, which may activate the expression of nucleotide sequences operably linked to the promoter in plant anther. An expression vector, a transgenic cell line, a host bacterium, and so on the nucleotide sequence described above also fall in the protection scope of the present A primer pair for amplifying any one of the nucleotide sequences of the promoter of SEQ ID and SEQ ID NO:9 also fall in the protection scope of the present disclosure.

The nucleotide sequence of the promoter provided in the present disclosure may be used to isolate corresponding nucleotide sequences from plants other than rice, particularly, by homology-based cloning from other monocotyledons. These corresponding nucleotide sequences may be isolated and identified by means of PCR, hybridization etc. based on the homology between these corresponding nucleotide sequences and the promoter of the present disclosure or the promoter. Therefore, the embodiments of present disclosure also comprise the corresponding fragments, which have sequence similarities to the promoter sequence of SEQ ID NO:3 or SEQ ID NO:9 (or fragments thereof) and may be isolated based on the similarities.

The term "promoter" used herein means a regulatory DNA region, commonly including TATA box guiding RNA polymerase II to initiate RNA synthesis at a proper transcriptional start site of a specific coding sequence. The promoter may also include other recognition sequences commonly located upstream of the TATA box, named as an upstream promoter element with a function of regulating transcriptional efficiency. As known to those skilled in the art, although the nucleotide sequence of the promoter region of the present has been identified, the isolation and identification of other regulatory element in upstream region of the TATA box of a specific promoter region identified in the present disclosure also falls in the scope of the present disclosure. Therefore, the promoter of the present disclosure may be further defined to include the upstream regulatory elements that regulate spatial and temporal expression patterns of the coding sequence. The promoter elements expressed in a target tissue (such as male reproductive organs) may be identified and isolated in the same way, and these promoter elements may be used together with a core promoter to examine the preferential expression in male-specific tissues. The core promoter means a minimal sequence for transcriptional onset, for example, a sequence known as the TATA box, which commonly exists the promoter of gene encoding a protein. Therefore, alternatively, the upstream promoter of FL2 gene may be used in association with the core promoter of the FL2 gene or core promoters from other sources.

The core promoter may be one of the known core promoters, such as 35S or 19S promoter of Cauliflower Mosaic Virus (U.S. Pat. No. 5,352,605), Ubiquitin promoter (U.S. Pat. No. 5,510,474), IN2 core promoter (U.S. Pat. No. 5,364,780), or figwort mosaic virus promoter.

The function of the gene promoter may be analyzed by the following methods: the nucleotide sequence of the promoter is operably linked to reporter gene to form a transformable construct, then the construct is transformed into plants to obtain transgenic progeny, and the expression of reporter gene in the transgenic progeny is examined for the expression pattern of the promoter. Alternatively, the promoter sequence linked to a reporter gene is subcloned into an expression vector, and the function of the promoter or other regulatory regions thereof is detected through the transient expression experiment.

The selection of suitable expression vectors for testing the function of the promoter or regulatory regions thereof depends on the host and the method of introducing the expression vector into the host, and the method is well known to one of ordinary skill in the art. For a eukaryotic gene, the sequence that should be subcloned into the expression vector comprises a region controlling transcription initiation and regulation. These regions are operably linked to a reporter gene including GFP, UidA, GUS gene or luciferase. The expression vector with a putative regulatory region located in the genome may be transformed into a whole organ, such as pollen at specific stages, or callus to examine its functions.

Furthermore, the promoter of the present disclosure may be linked to heterogenous nucleotide sequences other than the FL2 gene for to drive their expression. The nucleotide sequence of the promoter of the present disclosure and fragment and variant thereof and the heterogenous nucleotide sequence may be assembled into an expression cassette for expressing in target plants, more particularly in male organs of the plant. The expression cassette has a proper restriction site for inserting the promoter and the heterogenous nucleotide sequence. The expression cassettes may be used to genetically manipulate any plant to obtain desired corresponding phenotype.

The FL2 gene promoter of the present disclosure, more particularly the FL2 promoter of rice, may be used to activate the expression of several heterogenous nucleotide sequences to make the transformed plant male sterile. Specifically, the heterogenous nucleotide sequence may encode enzymes accelerating carbohydrate degradation, carbohydrate modification enzyme, amylase, debranching enzyme, or pectinase, such as the α-amylase gene, auxin, rot B, cytotoxin gene, diphtheria toxin, DAM methylase, avidin, or heterogenous nucleotide sequences selected from a prokaryotic regulation control system. The heterogenous nucleotide sequence can also be dominant male sterility gene.

In some embodiments, the nucleic acid operably linked to the downstream of the promoter in the present disclosure may be operably linked to a structural gene, a regulatory gene, an antisense sequence of the structural gene, an antisense sequence of the regulator gene or micro RNA interfering with the expression of a particular endogenous gene.

More explicitly, the gene of SEQ ID NO:1 and SEQ ID NO:5 regulating plant fertility provided in the present disclosure may be constructed into the downstream of the promoter of SEQ ID NO:3 and SEQ ID NO:9 to drive the specific expression of the gene in anther, or may be used to construct an RNAi vector targeting the gene of SEQ ID NO:1 driven by the promoter of SEQ ID NO:3 or SEQ ID NO:9 to silence the FL2 gene expression and to obtain the male sterile mutant of SEQ ID NO:1 gene.

The nucleotide sequence of the promoter of the present disclosure may be isolated from any plant, including but not limited to, *Brassica*, maize, wheat, sorghum, *Crambe* Linn, *Sinapis alba*, castor bean, sesame, cottonseed, linseed, soybean, *Arabidopsis, Phaseolus*, peanut, alfalfa, oat, rapeseed, barley, oat, rye, millet, dhurra, riticale, einkorn, Spelt, emmer, flax, Gramma grass, *Tripsacum*, euchlaena *Mexicana, Festuca ovina*, Perennial wheatgrass, sugarcane, *Vaccinium oxycoccos, papaya*, banana, Safflower, oil palm, muskmelon, apple, cucumber, dendrobe, *gladiolus, chrysanthemum*, Liliaceae, cotton, *eucalyptus*, sunflower, *Brassica rapa*, beet, coffee, ornamental plant, conifer and so on. Preferably, the plant includes maize, soybean, Safflower, mustard leaf, wheat, mustard leaf, barley, rye, rice, cotton and sorghum.

The present disclosure also provides a construct comprising FL2 gene and/or the promoter of FL2 gene, which includes a so-called vector or an expression cassette. The promoter of the construct driving the linked nucleotide sequence to express in the plant may be a natural promoter or a substituted promoter. The promoter of the construct may be an inducible promoter. The nucleotide sequence of FL2 gene may be linked to an anther-specific promoter, preferably, which may drive the nucleotide sequence of FL2 gene to fully express in the early development of anther, for example specifically in P7 of anther development. Particularly, the useful promoter types include a constitutive viral promoter, such as 35S promoter of Cauliflower Mosaic Virus (CaMV), 19s promoter of Cauliflower Mosaic Virus (CaMV), 35S promoter of figwort mosaic virus, and ubiquitin promoter.

A tissue-specific promoter may be used to enhance the transcription and/or expression targeted a specific plant tissue. The promoter may express in both the target tissue and other plant tissues, or express mainly in the target tissue, or express lower in the target tissue than the other plant tissues, or express highly preferably in the target tissue. In one embodiment, the promoter prefers to express particularly in plant male tissues or plant female tissues. For the method of present disclosure, the promoter may not be limited to any specific promoter with male tissue preference, and many promoters of such type known by the person skilled in the art may be used.

The natural FL2 promoter described herein is an example of the useful Another type of such promoters comprise 5126 promoter, MS45 promoter, MS26 promoter, BS92-7 promoter, SGB6 regulatory element and TA29 promoter and so on, which drive the linked gene to express in plant male tissues. The construct also comprises the promoter with gamete expression specificity. The promoters with gamete tissue expression specificity includes PG47 promoter and ZM13 promoter.

The construct described above may also comprise other components depending on the purpose and use of the vector construct. For example the construct may further comprise a selection marker gene, a targeting or regulatory sequence, a stabling sequence, a guiding sequence, or an intron. The expression cassette includes a target heterogenous nucleotide sequence with a transcriptional terminator and a translational terminator functioning in a plant at the 3' end thereof. The terminator may be the terminator of the gene of the present disclosure, or an exogenous terminator. More particularly, the above-mentioned terminator may be a termination region of nopaline synthase or octopine synthase.

If it is desired to target the expression product of the heterogenous nucleotide sequence to a specific organelle, such as plastid, amyloplast, endoplasmic reticulum or cell surface or extracellular secretion, the expression cassette may also comprise a nucleotide sequence that encodes a transit peptide. The transit peptide is known by the person skilled in the art and can be but not limited to a small subunit of Rubisco, a plant EPSP synthase, a maize Brittle-1 chloroplast transit peptide etc.

In the process of preparing the expression cassette, multiple DNA fragments may be manipulated to provide a DNA sequence in a proper direction or in a correct reading frame. In order to reach this aim, DNA fragments may be linked together via an adapter or a linker, or other convenient multiple cloning sites through other operations etc.

Further, the construct provided in the present disclosure also includes a marker gene for selecting transformed cells or transformed tissues. The selection marker gene includes an antibiotic-resistance gene or an herbicide-resistance gene. The proper selection gene includes, but is not limited to a chloramphenicol resistant gene, a hygromycin resistant gene, streptomycin resistant gene, a miramycin resistant gene, a sulfonamides resistant gene, a glyphosate resistant gene, a phosphinothricin resistant gene. The selection marker gene may be a red fluorescent protein gene, a cyan fluorescent protein gene, a yellow fluorescent protein gene, luciferase gene, a green fluorescent protein gene, and an anthocyanin biosynthetic gene etc.

The expression cassette or the vector provided in the present disclosure may be inserted into a plasmid, a cosmid, a yeast artificial chromosome, a bacteria artificial chromosome or any other vector suitable to be transformed into a host cell. Preferably the host cell is a bacteria cell especially the cell used to clone polynucleotide, maintain polynucleotide, or transform a plant cell, such as *Escherichia Coli, Agrobacterium tumefaciens* and Hair root soil bacteria. In the case of the host cell being a plant cell, the expression cassette or the vector may be inserted into a genome of the transformed plant cell, and the insertion may be either site-specific or random. Preferably, the insertion may be realized through homologous recombination. In addition, the expression cassette or the vector may be free from any chromosome. The expression cassette or the vector of the present disclosure can be in the nucleus, chloroplast, mitochondria and/or plastid of a plant cell. Preferably, the expression cassette or the vector may be inserted into a chromosome DNA in the plant cell nucleus.

The present disclosure also comprises the use of the FL2 gene disclosed in the present disclosure and the promoter thereof. In some embodiments of applications, the FL2 gene or the promoter thereof may be used to propagate and maintain the male sterile line obtained by mutating the FL2 gene or other genes related to fertility.

In details, the propagation and maintenance of the above-mentioned male sterile line involves using a male sterile mutant with a homozygous recessive nuclear gene as a transgenic acceptor and transformation of three tightly linked target genes into the male sterile mutant. The three tightly linked genes comprise a fertility restoration gene, a pollen inactivation gene, and a color/fluorescence-label screening gene. The fertility restoration gene may recover the fertility of the sterile transgenic acceptor. The pollen inactivation gene may inactivate any pollen containing the transformed exogenous gene. And the color/fluorescence-label screening gene may be used to sort the transgenic seeds from the non-transgenic seeds, and the sorted non-transgenic seeds may be used as a sterile line to produce hybrid seeds, while the sorted transgenic seeds may be used as a maintainer line to produce a sterile line continuously and steadily.

More explicitly, according to one embodiment of the present disclosure, rice recessive nuclear sterile fl2/fl2 mutant may be used as a receptor, and 3 tightly linked genes are transformed into the sterile line, wherein a fertility restoration gene OsFL2 may recover fertility of the transformed acceptor, a pollen inactivation gene Zm-PA may inactivate pollen, and a fluorescence screening (color sorting) gene RFP(r) is used to sort transgenic seeds from non-transgenic seeds, and the sorted non-transgenic seeds may be used as a sterile line to produce hybrid seeds, and the sorted transgenic seeds may be used as a maintainer line to produce a sterile line continuously and steadily. This technology produces non-transgenic product and bypasses the bottleneck problem in the process of rice hybrid seed preparation that low resource utilization in the three-line method and unstable fertility of the sterile line in the two-line method.

An anther-specific promoter provided in the present disclosure may be used to drive the specific expression of an exogenous gene in anther to avoid the continuous expression the exogenous gene in other tissues of the plant and any adverse effects caused by that. The anther-specific promoter may also be used in the functional analysis and identification of genes related to the plant pollen development, the establishment of the male sterile line and the restorer line, and pollen abortion experiment, and the biosafety problem caused by a plant transgene flow pollen escape may be avoided, which is important to establish the male sterile line and the line.

The present invention also provides a method of producing a plant, comprising:

(1) constructing an expression cassette provided herein,
(2) introducing the resulting expression cassette of step (1) into plant cells,
(3) regenerating transgenic plants from transformed plant cells, and
(4) screening through the transgenic plants, and
(5) optionally, propagating the plant of step (4) to obtain progenies.

The transgenic plant of the present disclosure is prepared by transformation methods known to those skilled in the art of a plant biotechnology. Any method may be used to transform a recombinant expression vector into the plant cell to generate the transgenic plant of the present disclosure. The transformation methods include a direct transformation method and an indirect transformation method. The proper direct transformation method includes DNA intake induced by polyethylene glycol, lipidosome-mediated transformation, introduction by particle gun, electroporation and microinjection and so on. In some embodiments of the present disclosure, the present disclosure uses transformation technology based on agrobacteria (referring to Horsch R B et al (1985) Science 225: 1229; White F F, Vectors for Gene Transfer in Higher Plants, Transgenic plants, Volume 1, Engineering and Utilization, Academic Press, 1993, pp. 15-38; Jenes B et al. Techniques for Gene Transfer, Transgenic plants, Volume 1, Engineering and Utilization, Academic Press, 1993, pp. 128-143, etc). *Agrobacterium* strains (such as *Agrobacterium tumefaciens* or *Agrobacterium rhizogenes*) contain a plasmid (Ti plasmid or Ri plasmid) with a T-DNA element. The plasmid with the T-DNA is transferred into plant after *Agrobacterium* transfection, with the T-DNA eventually integrated into the plant cell genome. T-DNA is located in the Ri-plasmid or the Ti-plasmid, or contained in a binary vector. An *Agrobacterium*-mediated transformation method is described in the examples. The *Agrobacterium*-mediated transformation method is most suitable for dicotyledons, but also suitable for monocotyledons. The way of transforming *Agrobacterium* into plants is described in the examples. Transformation may lead to both transient transformation and expression, and stable transformation and expression. Although the nucleotide sequence of the present disclosure may be inserted into various plants and various plant cell types, it is especially suitable for crop cells.

Compared with the prior art, the present disclosure has the following benefits: a rice anther development gene and the male sterile line generated by the mutation of the rice anther development gene are provided in the present disclosure. The male sterility is not influenced by environment and may be recovered by wild-type transgene. The rice anther development gene and the male sterile line generated by the mutation of the rice pollen development gene provide necessary components for constructing the third generation hybrid breeding system. The male sterile line generated by the mutation of the rice pollen development gene can be used to produce hybrid seeds, and is vital to improve the existing three-line and two-line methods.

EXAMPLES

The invention is now described with reference to the following Examples. The Examples are provided for the purpose of illustration only, and the invention is not limited to these Examples, but rather encompasses all variations which are evident as a result of the teachings herein.

Example 1: Screening for a Rice Male Sterile Mutant (Osfl2)

The seeds of the rice variety (*Oryza sativa* L. spp. *Indica*) Huanghuazhan (M0) were mutagenized by EMS (0.7%) for 12 hours to obtain the mutagenized population (M1). The seeds generated by the mutagenized plants from the M1 seeds were harvested and mixed to obtain a mutant library (M2). The plants from the M2 generation seed were screened to obtain male sterile plants at the seed maturation stage. The sterile plant was reproduced by cutting off rice stubbles, and pollen development in the reproduced plant was tested by I2-KI staining in reproductive period. A male sterile mutant showed no pollen and was named as Osfl2.

Example 2: Genetic Analysis of the Rice Male Sterile Mutant (Osfl2)

The sterile plant of the Osfl2 mutant was crossed with wild-type Huanghuazhan, and 80 F1 generation plants were all fertile. The F1 generation plants were self-fertilized to obtain 300 F2 plants, of which 78 plants manifested no pollen sterility and 222 plants showed complete fertility. The segregation ratio between the sterile plants and the fertile plants is very close to 1:3, which revealed the phenotype to be controlled by a recessive nuclear gene.

Example 3: Stability Analysis of the Rice Male Sterile Mutant (Osfl2)

To confirm whether the sterility of the osfl2 mutant was influenced by environmental conditions such as light or temperature etc, the F2 generation plants obtained through crossing the sterile plant with wild-type Huanghuazhan were grown in Shenzhen, Sanya, Hunan, Beijing to further observe the sterility and the segregation ratio. In all areas, the ratio between the sterile plants and the fertile plants is 1:3 (FIG. 1, and the reproduced plants from the sterile rice stub still manifested sterility, thus the sterility of the mutant was not influenced by environmental factors.

TABLE 1

The segregation ratio in the F2 generation plant obtained by self-fertilization of the F1 plants (the progeny of Osfl2 mutants and the wild type Huanghuazhan)

|  | Number of fertile plants | Number of sterile plants | $\chi^2$ (3:1) |
|---|---|---|---|
| Shenzhen | 88 | 31 | 0.034 |
| Sanya | 104 | 29 | 0.150 |
| Hunan | 65 | 21 | 0.000 |
| Beijing | 61 | 19 | 0.033 |

Example 4: Phenotypic Analysis of the Reproductive Organ of the Rice Male Sterile Mutant (osfl2)

Figure 2:
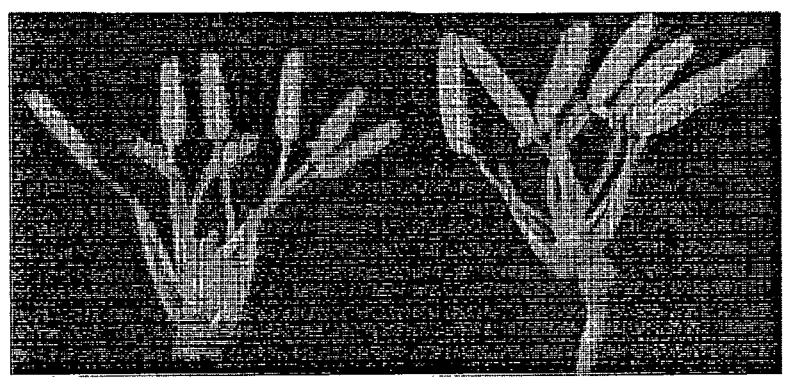
FIG. 2—depicts anther morphology of Huanghuazhan with mutant OsFL2 or wild-type OsFL2.
Figure 3:
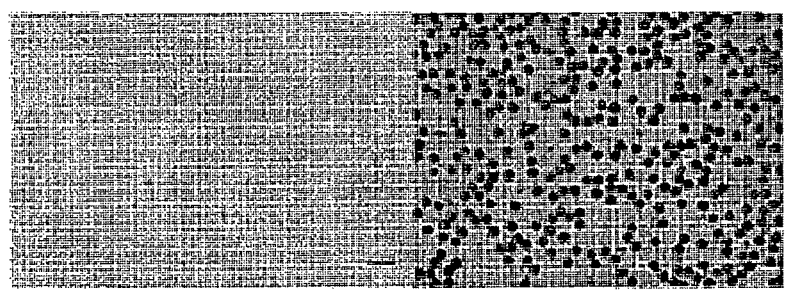
FIG. 3—depicts pollen dye-staining analysis of Huanghuazhan with mutant OsFL2 or wild-type OsFL2.
Figure 4:
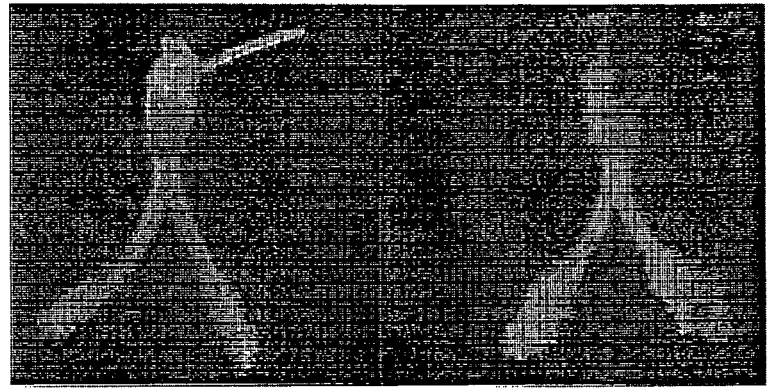
FIG. 4—depicts morphological comparison of female organs of Huanghuazhan with mutant OsFL2 and wild-type OsFL2.
Figure 5:
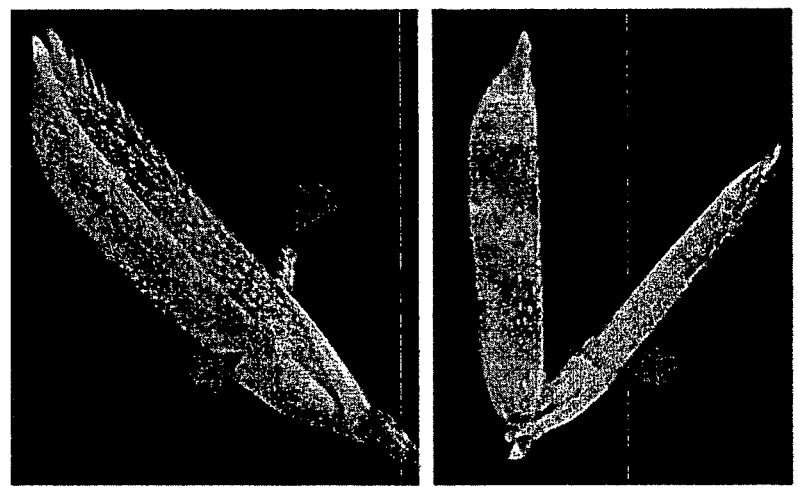
FIG. 5—depicts the exposed stigma of mutant plant, and an arrow indicates the exposed stigma.

Compared with the wild-type plant, the mutant plant grew and developed normally, blooming at the same stage. The size, morphology, opening size and opening time of lemma and glum of the mutant plant were not different from the wild-type plant (FIG. 1). But the anther of the mutant plant was white, thin, small, and indehiscent (FIG. 2), with no pollen. Further I2-KI staining was performed to detect if there is any pollen in the mutant plant, and it showed the wild-type pollen stained normally while the mutant plant did not have pollen (see FIG. 3). The female organs of the mutant plant (including ovary, style, stigma) were all slightly bigger than the counterparts from the wild-type plant (FIG. 4). Exposure rate of stigma of the mutant plant was at least 89% (FIG. 5), while the stigmas of wild-type Huanghuazhan are rarely exposed, sterile plants were mixed with the fertile plant and sowed under a natural condition, so that the sterile mutant plant may be cross-pollinated by the fertile plant to recover fruiting ability. The statistical analysis of 100 mutant plants showed that by this means and the seed setting rate was increased at least 40%. By contrast, under an artificial condition, the sterile mutant plant may be cross-pollinated from the fertile plant, and seed setting rate was increase to 70%-80%. Further seed of the mutant plant developed normally without any defects.

Example 5: Gene Cloning of the Rice Male Sterile Mutant

Figure 7:
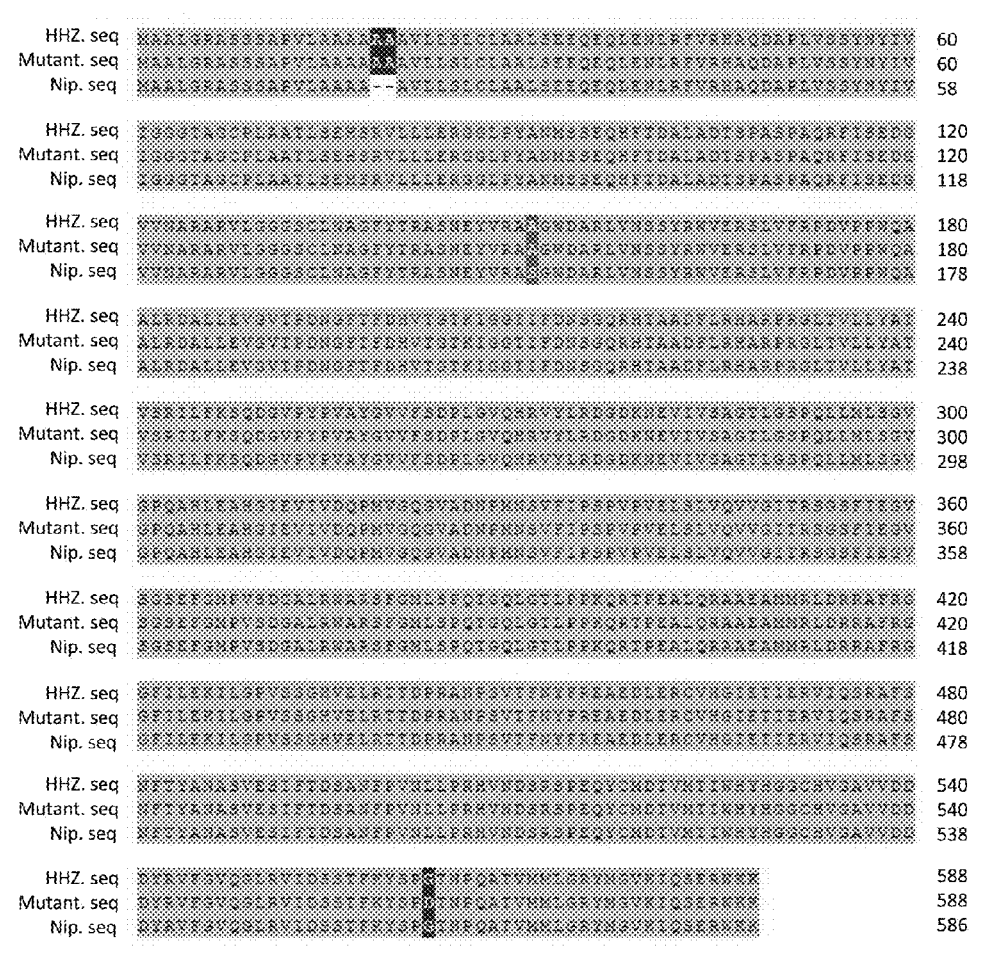

Cloning of the mutant gene was based on the Mutmap method, which involves constructing F2 progenies by crossing the mutant with the wild-type parent, and mapping the by re-sequencing. The sterile plant was crossed with wild-type Huanghuazhan, then 30 sterile plants of F2 generation were selected for extraction of genomic DNA, and the genomic DNA mixed equally for high-throughput genome sequencing to get 20 Gb sequence data amounting to x rice genome. The mutant gene may be Os10g38050 allele located on the 10.sup.th chromosome compared with the genomic sequence of wild-type Huanghuazhan. The full-length coding sequence of the gene of wild-type Huanghuazhan is 1767 bp, and the nucleotide sequence of the gene was shown a SEQ ID NO:1. The protein encoded by SEQ ID NO:1 contains 588 amino and the sequence of amino acids was shown as SEQ ID NO:2. In the sterile mutant, G was into A at the 1688.sup.th nucleotide of the coding sequence of the gene (FIG. 6A-C), and as a result, (G) was changed into Aspartic acid (D) at the 563.sup.th amino acid of the corresponding protein sequence encoded by the gene (FIG. 7). The latest SNP (Single Nucleotide Polymorphism) tool HRM (High Resolution Melt) analysis was performed to further confirm that all non-pollen plants carried the homozygous mutation while the fertile plant carried a homozygous wild-type or a heterozygous site. The offspring from self-pollination of the homozygous wild-type plant all fertile, and the offspring from self-pollination of the heterozygous plant shows a segregation ratio at 1:3 between the sterile offspring and the fertile offspring. The cDNA coding sequence of the gene contains several sequence polymorphisms between *Japonica* rice Nipponbare and wild-type Huanghuazhan (FIG. 6A-C). Compared with Huanghuazhan OsFL2, Nipponbare OsFL2 contains a 6-bp nucleotide deletion from the 59.sup.th to the 64.sup.th of the coding sequence, a G-to-T nucleotide substitution at the position 451, and a G-to-A nucleotide substitution at position 1371 the coding sequence. As a result, two protein polymorphism were detected, a deletion containing the 20.sup.th and the 21.sup.th amino acids of the protein sequence, and a Alanine (A) to Serine (S) substitution at position 151 of the protein (FIG. 7). The nucleotide sequence of the Nipponbare was shown as SEQ ID NO:5, and the coding amino acid sequence thereof was SEQ ID NO:6. Further analysis showed that the gene does not show any polymorphism between *indica* rice 9311 and wild-type Huanghuazhan.

Figure 8:
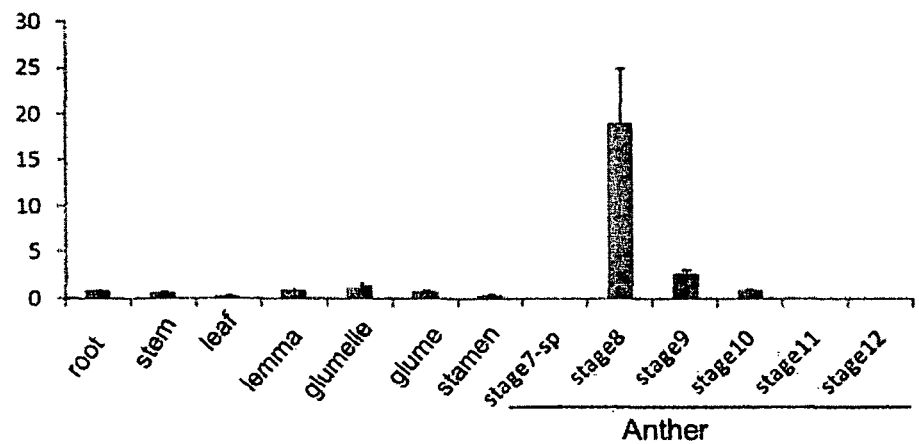
FIG. 8—Analysis of expression level of OsFL2 in different tissues and organs of rice.

Example 6: Expression Pattern Analysis of OsFL2 Gene in Different Organs of the Rice A pair of primers were designed based on the cDNA sequence of OsFL2, with the forward primer F1 5' GCCT-CACCGTCCTCCTCTAC 3' (SEQ ID NO:33) and the reverse primer R1 5' CGGGTCCGAGAACACCAC 3' (SEQ ID NO:34). Meanwhile, primers for internal controls were designed against a rice gene Actin, with a forward primer 5' GCTATGTACGTCGCCATCCA 3' (SEQ ID NO:35) and a reverse primer 5' GGACAGTGTGGCTGACACCAT 3' (SEQ ID NO:36). Total RNA was extracted from Huanghuazhan rice and used as the template for the synthesis of the $1^{st}$ strand cDNA. Real-time quantitative PCR was used to analyze OsFL2 gene expression profile in the root, stem, leaf, lemma, palea, glume, pistil and young anther at primordium differentiation stage (stage6), young anther at early pollen mother cell meiotic stage (stage7), tetrad formation stage (stage8), early microspore stage (stage9), middle and late microspore stage (stage10), pollen maturing stage (stage12), and the result as depicted in FIG. 8 showed that the OsFL2 gene had specific and high expression in young anther at pollen mother cell meiosis stage (stage7). The expression of the OsFL2 gene began to decrease at tetrad formation stage (stage8), while the expression of the OsFL2 gene was very low in the root, stem, leaf, seed and other anther developmental stage.

Figure 9:
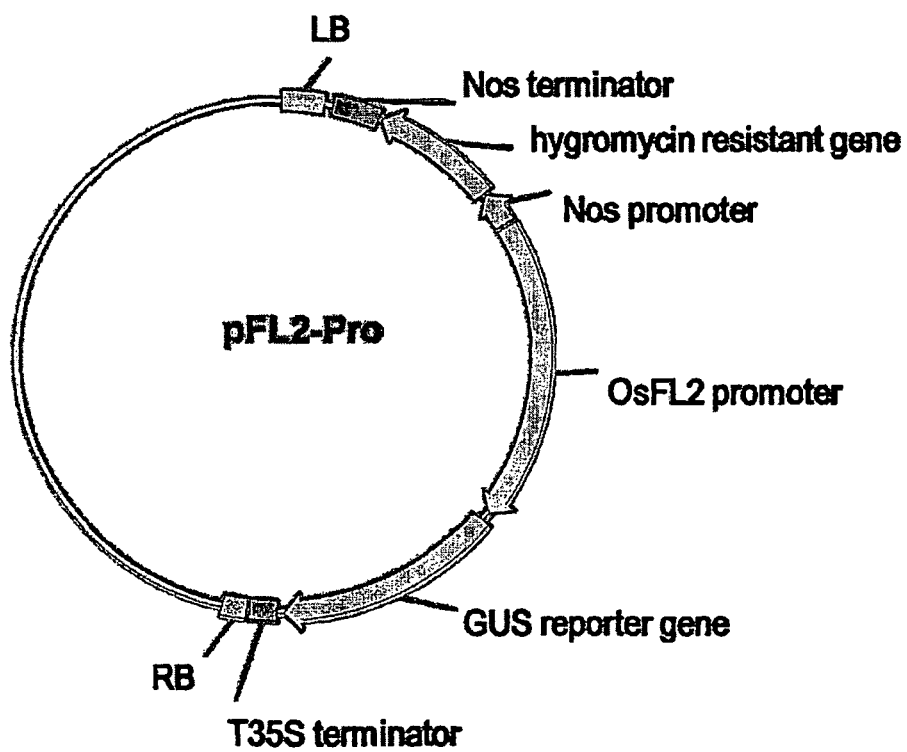
FIG. 9—Expression vector of the promoter of OsFL2 gene.
Figure 10:
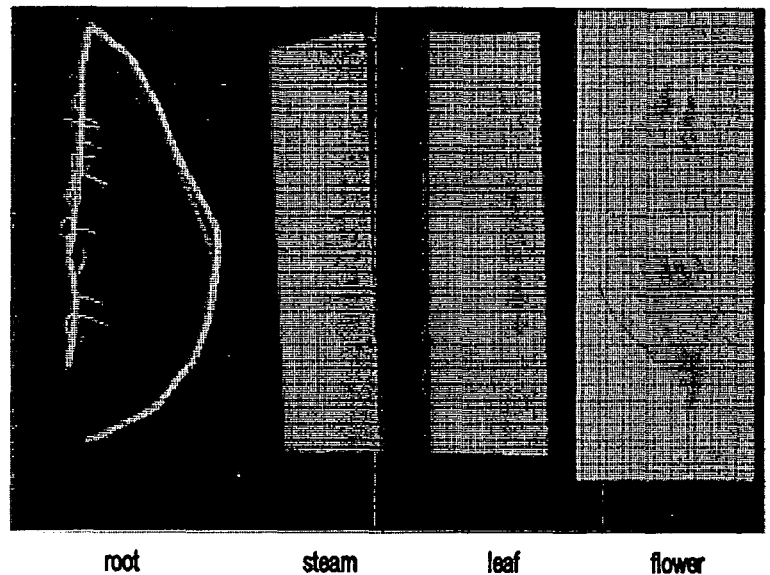
FIG. 10—depicts the promoter of OsFL2 gene activates GUS gene to express specifically in rice anther.
Figure 11:
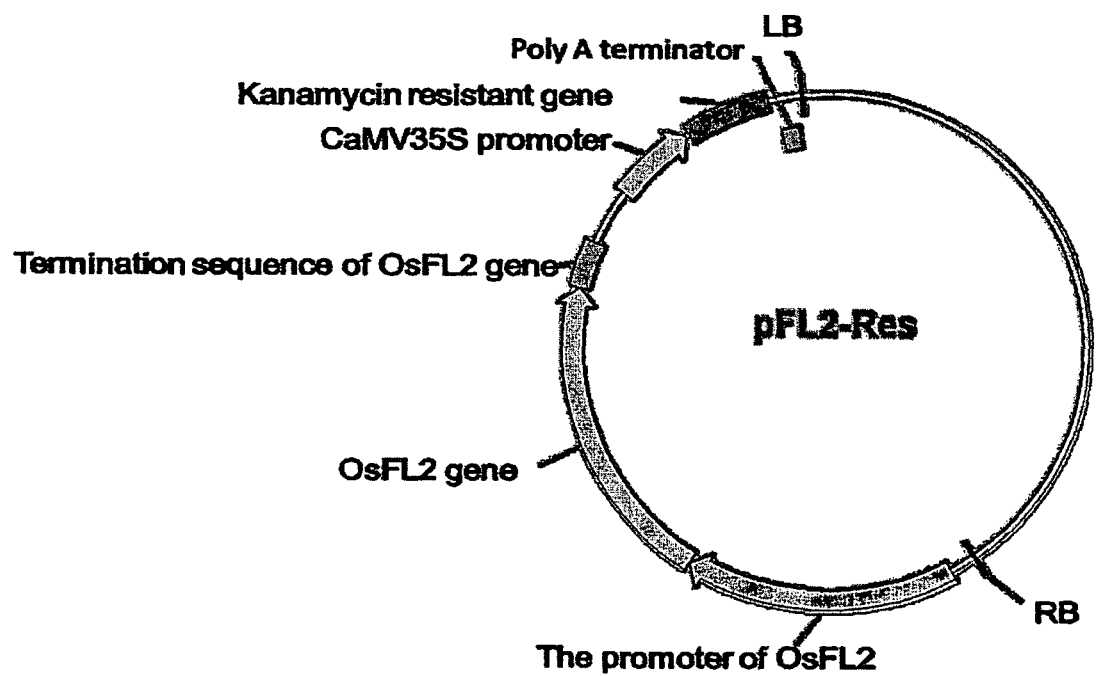
FIG. 11—depicts transgene complementation vector of the rice male sterile mutant (OsFL2).
Figure 12:
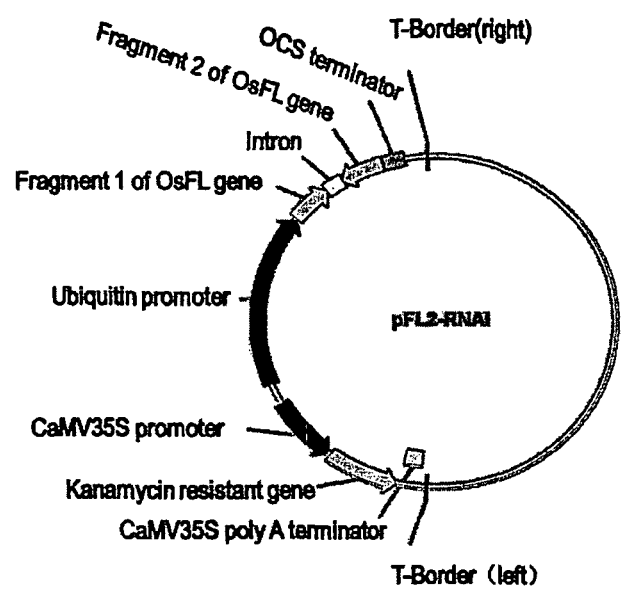
FIG. 12—depicts RNA interference vector of OsFL2 gene.

Example 7: Construction of OsFL2 Gene Expression Vector and Functional Analysis of the Gene Promoter The OsFL2 gene expression vector (FIG. 9) was constructed for the functional analysis of the gene promoter. First, the primer OsFL2-Pro-F (ggatccGGATTTCGAG-GATCAAGCT, SEQ ID NO:37) and the primer OsFL2-Pro-R (gtcgacTTTCGCCGGGCAAATTCGC, SEQ ID NO:38) were used to amplify the 2520 bp promoter region upstream of OsFL2 gene (SEQ ID NO:3) from the wild type Huanghuazhan genomic DNA. The amplified product was digested by SalI and BamHI and ligated into a detecting vector to obtain pOsFL2-pro vector (plasmid). The obtained pOsFL2-pro vector was transformed into wild-type rice callus by the *agrobacterium*-mediated transformation method, and 12 transgenic rice plants were selected and regenerated. Expression pattern of OsFL2 promoter analyzed by detecting the activity of β-galactosidase. GUS Staining in the root, stem, leaf and flower of the transgenic plants demonstrated that GUS gene driven by the promoter of OsFL2 was mostly expressed in anther of the rice (shown in FIG. 10). In addition, functional analysis of promoter shown as SEQ ID NO:9 linked to GUS showed that the staining result of SEQ ID NO:9 was consistent with the staining result of SEQ ID NO:3, and they were both another-specific promoters.

Example 8: Complementation Test of the Rice Male Sterile Mutant (Osfl2)

To confirm that the OsFL2 mutation was responsible for the male sterile phenotype in the mutant, a complementation vector containing the full-length wild type OsFL2 gene was constructed and transformed into plants to complement the Osfl2 phenotype. Specifically, the full-length genomic fragment from 2500 bp bases upstream of OsFL2 initiation codon ATG to approximate 497 bp bases downstream of OsFL2 termination codon TGA (SEQ ID NO: 4), was amplified using the primer OsFL2-Res-F (gtttaaacG-GATTTCGAGGATCAAGCT, SEQ ID NO:39) and the primer OsFL2-Res-R (ggatccACCCTGCATTTTTTAT-GCC, SEQ NO:40). The fragment was digested by PmeI and BamHI and ligated into a complementation vector to obtain pOsFL2-Res vector (plasmid). The obtained pOsFL2-Res vector was into the callus induced from Huanghuazhan osfl2 mutant seeds by the *agrobacterium*-mediated transformation method, and the transgenic plants were selected and regenerated. 8 positive transgenic plants were obtained and all of them showed restored fertility. This analysis further demonstrated OsFL2 gene was involved in pollen development regulation and the mutation in OsFL2 gene led to the non-pollen phenotype.

Example 9: Acquisition and Phenotypic Analysis of OsFL2 Gene RNAi Line

Figure 13:
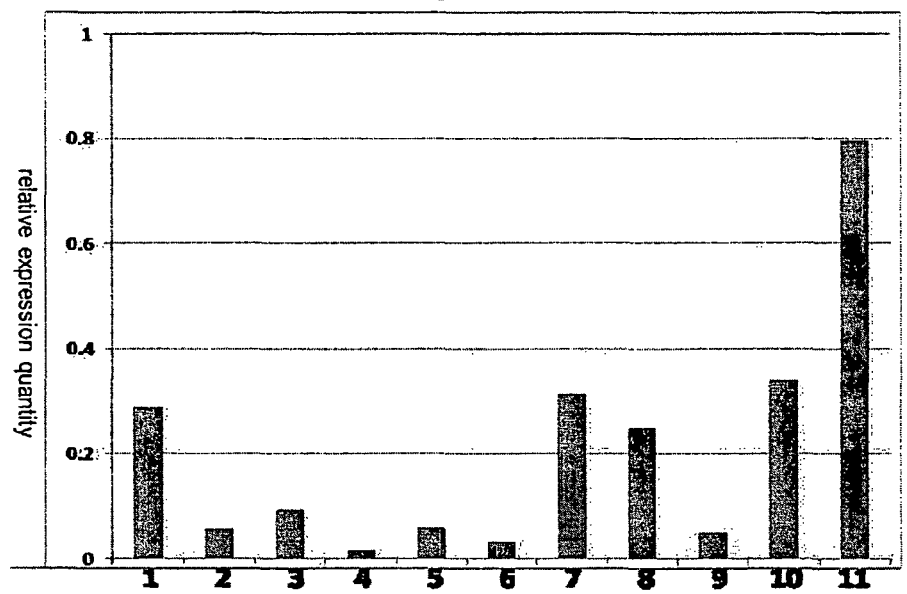
FIG. 13—depicts expression of OsFL2 gene in young panicle anther of transgenic plants with RNA interference vector, and 1-10 represent transgenic plants, 11 represents a wild-type plant.

To further confirm that disturbed expression of OsFL2 gene results in male sterility, an RNAi line to specifically knockout OsFL2 was constructed. Specifically, a 474 bp OsFL2 cDNA fragment was amplified using the primer OsFL2-Flag-F (GCGTCGCCGACAACCC, SEQ ID NO:41) and the primer OsFL2-Flag-R (TGGAGAAGGC-CCGCGAC, SEQ ID NO:42). The amplified product was further amplified with two pairs of amplification primers to obtain a forward OsFL2 gene fragment 1 with a KpnI site and a reverse OsFL2 gene fragment 2 with a BamHI site. The two fragments were digested, ligated, and incorporated into a pRNAi vector to obtain pOsFL2-RNAi. The obtained pOsFL2-RNAi was transformed into Nipponbare callus by the *Agrobacterium*-mediated transformation method, and 10 transgenic plants were selected and regenerated and the male fertility in 7 of the transgenic plants reduced significantly. Real-time quantitative PCR using the prime pair of example 6 based on OsFL2 and Actin cDNA was conducted to analyze expression level of OsFL2 gene in young anther at pollen mother cell meiosis stage and tetrad formation stage (P7) of the RNAi plants, and the result showed RNA expression level of OsFL2 gene of the transgenic sterile plants reduced significantly (FIG. 13). This analysis further demonstrated OsFL2 gene was involved in pollen development regulation and the mutation of OsFL2 gene led to non-pollen phenotype.

Example 10: Cross-Pollination Analysis of the OsFL2 Mutant Plant with the Restorer Line Huanghuazhan OsFL2 mutant plant may be cross-pollinated by several frequently-used restorer lines for the production of hybrid seeds. Hybrid seeds from some combinations showing obvious heterosis, demonstrating Huanghuazhan mutant is valuable in hybrid-breeding and can be used as a candidate material for the sterile line. Huanghuazhan OsFL2 mutant plant was crossed to several restorer lines, and that stigmas of the F2 generation sterile plant were still highly exposed (exposure rate of stigma was up to 60-88%) demonstrated a linkage inheritance existing in the mutant gene and a stigma exposure trait. High exposure of stigma was beneficial to cross-pollination and improved efficiency of hybrid seed production.

Figure 14:
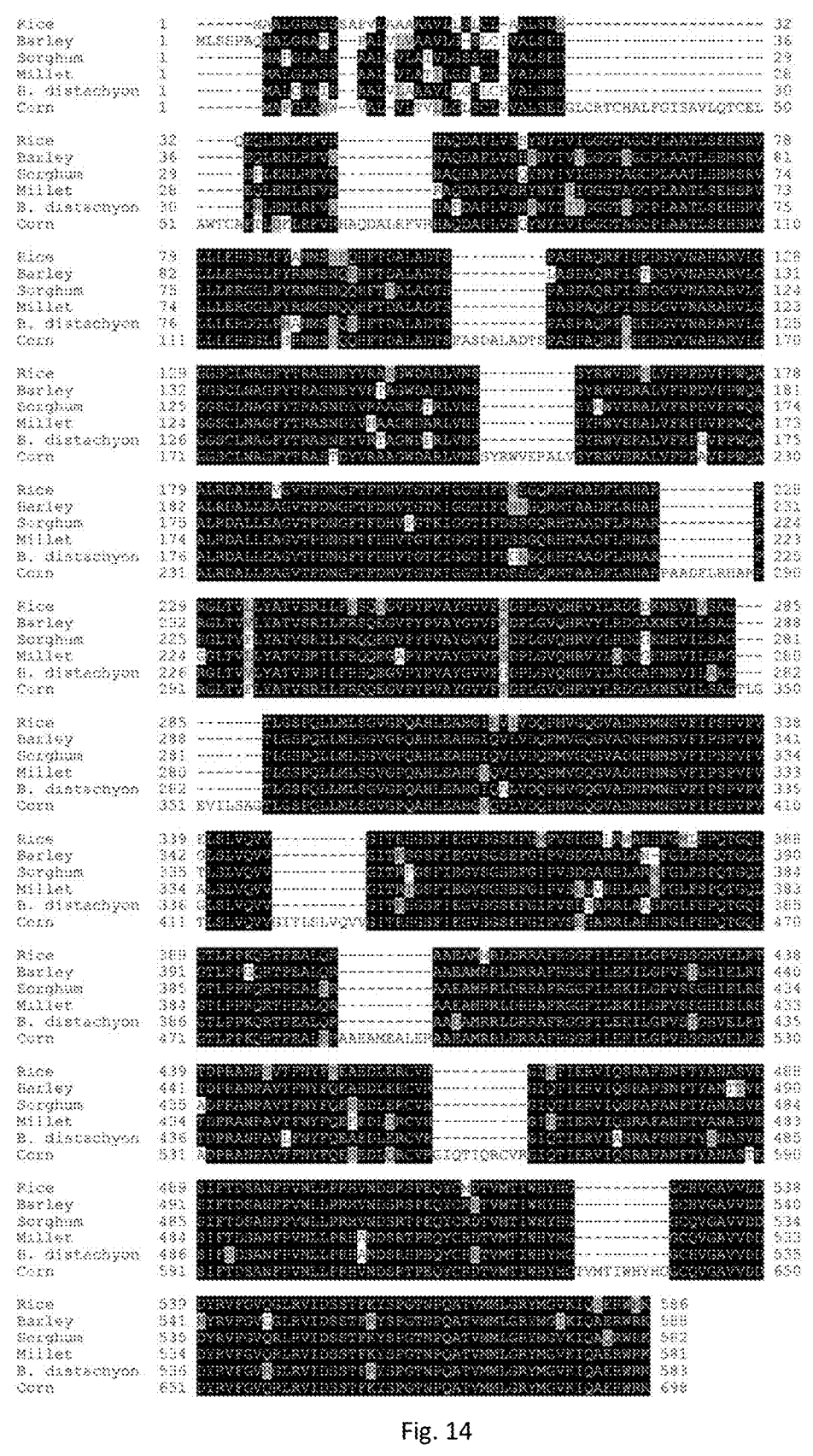

Example 11: Alignment of the OsFL2 Protein with the Predicted Protein Homologues from Barley, Sorghum and Maize In NCBI database, using protein blast, the complete rice OsFL2 protein sequence was used as the query to search in the protein database for its protein homologues in the genomes of barley, sorghum, maize, millet and *Brachypodium distachyon*. The obtained protein sequences were aligned, and the result showed that they were highly homologous with each other (FIG. 14), indicating that the homologous protein has a conserved biological function and plays an important role in the development of male fertility of the plant.

Herein, the nucleotide sequence of the fertility gene of barley was shown as SEQ ID NO:10 or 11, and the amino acid sequence of the fertility gene of barley was shown as SEQ ID NO:12, the nucleotide sequence of the fertility gene of sorghum was shown as SEQ ID NO:13 or 14, and the amino acid sequence of the fertility gene of sorghum was shown as SEQ ID NO:15, the nucleotide sequence of the fertility gene ZmFL2 of maize was shown as SEQ ID NO:16 or 17, and the amino acid sequence of the fertility gene ZmFL2 of maize was shown as SEQ ID NO:18, the nucleotide sequence of the fertility gene of millet was shown as SEQ ID NO:19, and the amino acid sequence of the fertility gene of millet was shown as SEQ ID NO:20, the nucleotide sequence of the fertility gene of *Brachypodium distachyon* was shown as SEQ ID NO:21 or 22, and the amino acid sequence of the fertility gene of *Brachypodium distachyon* was shown as SEQ ID NO:23.

Example 12: The Application of OsFL2 Gene in the Innovation of a New Hybrid Breeding Technique OsFL2 gene may be applied in new generation of hybrid breeding technique, and the core idea of the technique was: the recessive rice nuclear male sterile mutant was used as the transformation acceptor material, and three closely-linked genes were transformed into the sterile mutant. Thereinto, a fertility-recovering gene can recover the fertility of the transformation acceptor, an pollen-inactivation gene can inactivate pollen containing the transgene, a color-label gene can be used for sorting of a transgenic seed from a non-transgenic seed, and the sorted non-transgenic seed was used as the sterile line, while the transgenic seed was used as the maintainer line. The maintainer line may pollinate the sterile line to propagate the sterile line, while the maintainer line can self-pollinate. As the technique utilizes biotechnology to produce a non-transgenic product, the bottleneck problem in the rice hybrid seed production is solved, especially the low resource utilization of three-line method and the instability of the sterile line of two-line method.

Based on the above-mentioned principle, the inventors used the OsFL2 gene of the rice plant to construct the expression vector pZN3. Before constructing the rice plant expression vector, the inventors firstly transformed each of the three expression cassettes, Zm-PA, OsFL2 and RFP, into the rice plant respectively and further verified the function of each expression cassette. The result indicated that each expression cassette can work well as initially designed when transformed into the rice plant alone.

Figure 15:
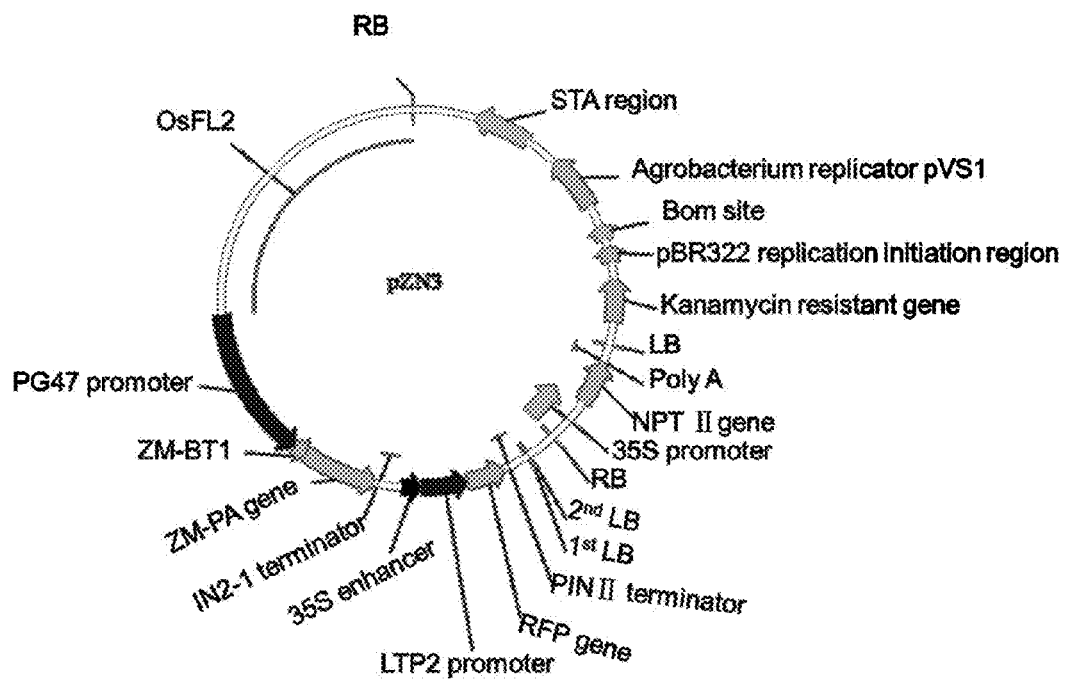
FIG. 15 depicts pZN3 vector.

Further, the inventor constructed pZN3 vector depicted in FIG. 15 by assembling the following DNA elements:
1) pCAMBIA2300 vector as the backbone;
2) expression cassette LTP2: RFP(r)-PINII, an open reading frame of RFP(r) gene (SEQ ID NO: 24) were linked between the promoter of LTP2 (SEQ ID NO: 25) and the terminator of PINII (SEQ ID NO: 26) to recombine the expression cassette of RFP(r) (LTP2:RFP(r):PINII),
3) OsFL2 expression cassette that comprises the full length of OsFL2 from the gene promoter to the gene terminator as SEQ ID NO:27. The complete nucleotide sequence between the promoter and the terminator of marker gene of OsFL2 gene was SEQ ID NO: 4, and the promoter of OsFL2 gene was SEQ ID NO: 3, the terminator of OsFL2 gene was SEQ ID NO: 28, the genomic DNA sequence of OsFL2 gene was SEQ ID NO: 27, the amino acid sequence of the protein encoded by the nucleotide sequence was SEQ ID NO: 2,
4) expression cassette of PG47: ZM-BT1: ZM-PA: IN2-1, the open reading frame of the pollen-inactivation gene ZM-PA (the nucleotide sequence was SEQ ID NO: 29) was linked to the promoter of PG47 (the nucleotide sequence was SEQ ID NO: 30), the downstream region of a transit peptide of ZM-BT1 (the nucleotide sequence was SEQ ID NO: 31), the upstream region of the terminator of IN2-1 (the nucleotide sequence was SEQ ID NO: 32).

Rice transformation: plasmid pZN3 was transformed into Ag10 strain of *Agrobacterium* by electroporation, and the genetic transformation was carried out on the rice callus of Huanghuazhan homozygous for the recessive male sterile OsFL2 mutation through *Agrobacterium*-mediated transformation. 26 independent single-copy transgenic plants were obtained. The specific transformation acceptor material was obtained through the following process: Huanghuazhan seed homozygous for the OsFL2 recessive mutation was distinguished from the heterozygous seed by HRM (high resolution melting), and the callus of the homozygous Osfl2 mutant seed was induced and transformed.

Figure 16:
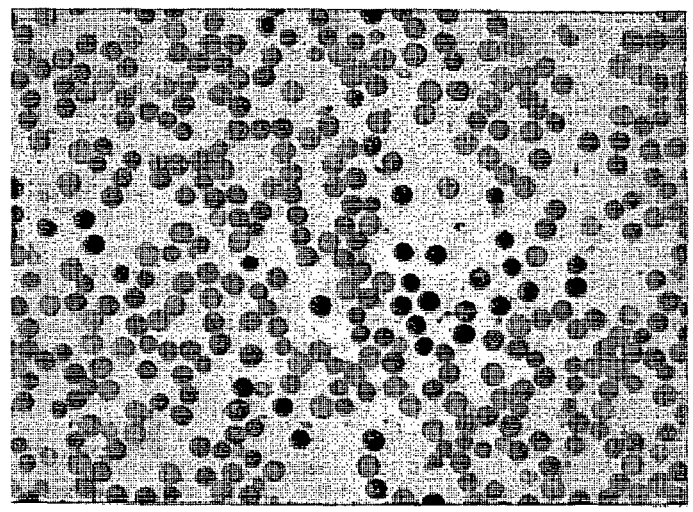
FIG. 16 shows fertile pollen grains and sterile pollen grains after dye-staining.

To examine the pollen fertility of the transgenic rice, 26 obtained single-copy transgenic rice (with the homozygous OsFL2 recessive sterile site) were analyzed. It was found that there was no significant morphological difference between the transgenic plant and the non-transgenic plant, while the fertility was significantly different. Analysis of pollen stainability was carried out on the transgenic plant described above, using the wild-type rice as the control (FIG. 16). The adopted method included: drawing a single plant randomly from the transgenic rice and the wild-type rice as a control plant respectively in a flowering period, picking a flower respectively from either of the obtained single plant and getting an anther respectively from the obtained flowers, then placing the obtained anther respectively in the centre of a glass slide and adding a drop of 1% I2-KI solution, using a tweezer and a dissecting needle to release pollen, then the glass slide was covered with a cover slip. The sample was observed under a microscope to count the stained pollen number and the total pollen number. The pollen stained blue-black represented the fertile pollen while the pollen stained lightly represented aborted pollen (FIG. 16 depicts the fertile pollen grains and the sterile pollen grains after staining). Pollen stainability of the transgenic rice was analyzed, and the result showed that the stainable pollen of the control plant is about 98%~100% while the ratio between the normal pollen (stainable) and the aborted pollen (non-stainable) was approximate 1:1 in transgenic plants. The result indicated that the constructed maintainer line can produce equal amount of pollen grains with the exogenous gene and without the exogenous gene, i.e. the pZN3 construct made 50% of the pollen of the transgenic plant inactive. The result indicated that the vector provided in the present disclosure is able to inactivate the pollen as expected.

Figure 17:
FIG. 17 depicts fluorescence segregation ratio analysis of seeds harvested from transgenic plants, and the segregation ratio of the seeds is 1:1.

Segregation analysis of fluorescent seeds and non-fluorescent seeds of the transgenic rice: the ratio of fluorescent segregation of the T1 generation seeds from 26 obtained single copy-transgenic rice (with the homozygous OsFL2 recessive sterile site) described above was analyzed, and the result indicated the segregation ratio of these seeds was 1:1 (FIG. 17), i.e. the segregation ratio between the fluorescent seed with the transgene and the non-fluorescent seed without the transgene was 1:1. The result also indicated the elements in the vector as a combination provided in the present disclosure expressed well and can be used toward creating and breeding the sterile line as well as the maintainer line. Then, OsFL2 gene can recover the fertility of the male sterile mutant acceptor, and the expression of Zm-PA gene and RFP gene can be used to inactivate pollen and for seed selection, respectively.

What is claimed is:

1. A method for producing a male sterile *Oryza sativa* plant, comprising the step of:

inactivating the FL2 gene in an *Oryza sativa* plant, wherein the FL2 gene encodes the cDNA sequence of SEQ ID NO:1, or inhibiting the expression of the FL2 gene in the *Oryza sativa* plant, thereby producing a male sterile *Oryza sativa* plant.

2. The method of claim 1, further comprising:

restoring male sterility in the plant by breeding.

3. The method of claim 2, wherein the breeding comprises:
hybridizing the plant as a female parent sterile line with a restorer line to produce a hybrid seed.

4. The method of claim 1, wherein the step of inactivating the FL2 gene in an *Oryza sativa* plant comprises introducing a G→A mutation at position 1688 of SEQ ID NO:1.

* * * * *